(12) United States Patent
Jeong et al.

(10) Patent No.: US 7,390,485 B2
(45) Date of Patent: Jun. 24, 2008

(54) DESIGN AND THERAPEUTIC USE OF ADPASE ENHANCED APYRASES

(75) Inventors: Soon S. Jeong, St. Louis, MO (US); Ridong Chen, Naperville, IL (US); Timothy A. Mitsky, Maryland Heights, MO (US)

(73) Assignee: APT Therapeutics, Inc., St. Louis, MO (US)

( * ) Notice: Subject to any disclaimer, the term of this patent is extended or adjusted under 35 U.S.C. 154(b) by 494 days.

(21) Appl. No.: 11/069,543

(22) Filed: Feb. 28, 2005

(65) Prior Publication Data

US 2005/0215505 A1    Sep. 29, 2005

Related U.S. Application Data

(60) Provisional application No. 60/548,344, filed on Feb. 27, 2004.

(51) Int. Cl.
*A61K 38/44*    (2006.01)
*A61K 39/00*    (2006.01)
*C12N 9/02*    (2006.01)

(52) U.S. Cl. .................... 424/94.6; 424/192.1; 435/189; 435/325; 536/23.2

(58) Field of Classification Search .................. 435/195, 435/189; 424/192.1, 94.6; 536/23.2
See application file for complete search history.

(56) References Cited

U.S. PATENT DOCUMENTS 6,335,013 B1   1/2002  Ford et al.
6,350,447 B1 *  2/2002  Chadwick et al. .......... 424/94.6

FOREIGN PATENT DOCUMENTS

WO    WO-00/23459    4/2000
WO    WO-01/11949    2/2001

OTHER PUBLICATIONS

Sequence search alignment between Accession O75355 (Nov. 1, 1998) and Seq ID No. 56.*
Sequence search alignment between Accession No. AAE19882 (native Human CD39L3 protein) (Feb. 2002) and Applicants Seq ID No. 56.*
International Search Report for PCT/US05/06568, mailed on Aug. 18, 2005, 3 pages.
Yang et al., Biochemistry (2001) 40:3943-3950.
Chiu et al., Stroke (1998) 29:18-22.
Gayle et al., J. Clin. Invest. (1998) 101:1851-1859.
Kaczmarek et al., J. Biol. Chem. (1996) 271:33116-33122.
Marcus and Safier, Faseb J. (1993) 7:516-522.
Marcus et al., J. Clin. Invest. (1997) 99:1351-1360.
Wardlaw et al., Lancet (1997) 350:607-614.

* cited by examiner

*Primary Examiner*—Tekchand Saidha
(74) *Attorney, Agent, or Firm*—Morrison & Foerster LLP

(57) ABSTRACT

The present invention provides for design and therapeutic use of ADPase enhanced polypeptides, pharmaceutical compositions, and methods useful for preventing and reversing platelet aggregation and recruitment for the treatment and prevention of vascular disorders in mammals.

28 Claims, 10 Drawing Sheets

Figure 1.

```
CD39       ---------------------------------MKGTKDLTSQQKESNVKTFCSK  22
CD39L1     ----------------------------------------MAGKVRSLLPP  11
CD39L2     MKKGIRYETSRKTSYIFQQPQHGPWQTRMRKISNHGSLRVAKVAYPLGLCVGVFIYVAYI  60
CD39L3     -----------------------------------MFTVLTRQPCEQAGLKALYRTPT  23
CD39L4     ------MATSWGTV--F----------F----------------M--LVVSCVCSAVS  22
NTPDase4   ----IGISCLFPASWHFSISPVGCPRILNTNLRQIMVISVLAAAVSLLYFSVVIIRNKYG  56
                                                         ACR I
CD39       NILAILGFSSIIAVI--------ALLAVGLTQNKALPENVKYGIVLDAGSSHTSLYIYKW  74
CD39L1     LLLLAAAGLAGL-----------LLLCVPTRDVREPPALKYGIVLDAGSSHTSMFIYKW  58
CD39L2     KWHRATATQAFFSITRAAPGARWGQQAHSPLGTAADGHEVFYGIMFDAGSTGTRVHVFQF 120
CD39L3     IIALVVLLVSIVVLV--------SITVIQIHKQEVLPPGLKYGIVLDAGSSRITVYVYQW  75
CD39L4     HRNQQTWFEGIF-----------LSSMCPINVSAS---TLYGIMFDAGSTGTRIHVYTF  67
NTPDase4   RLTRDKKFQRYL-----------ARVTDIEATDTNNPNVNYGIVVDCGSSGSRVFVYCW 104

CD39       PAEKENDTGVVHQVEECRVKG--------PGISKFVQKVNEIGIYLTDCMERAREVIPRS 126
CD39L1     PADKENDTGIVGQHSSCDVPG--------GGISSYADNPSGASQSLVGCLEQALQDVPKE 110
CD39L2     TRP-PRETPTLTHETFKAVK---------PGLSAYADDVEKSAQGIRELLDVAKQDIPFD 170
CD39L3     PAEKENNTGVVSQTFKCSVKG--------SGISSYGNNPQDVPRAFEECMQKVKGQVPSH 127
CD39L4     VQKMPGQLPILEGEVFDSVK---------PGLSAFVDQPKQGAETVQGLLEVAKDSIPRS 118
NTPDase4   PRHNGNPHDLLDIRQMRDKNRKPVVMKIKPGISEFATSPEKVSDYISPLLNFAAEHVPRA 164
                ACR II                                 ACR III
CD39       QHQETPVYLGATAGMRLLRMESEELADRVLDVVERSLSNYPFDF--QGARIITGQEEGAY 184
CD39L1     RHAGTPLYLGATAGMRLLNLTNPEASTSVLMAVTHTLTQYPFDF--RGARILSGQEEGVF 168
CD39L2     FWKATPLVLKATAGIRLI---PGEKAQKLLQKVKEVFKASPFLVGDDCVSIMNGTDEGVS 227
CD39L3     LHGSTPIHLGATAGMRLLRLQNETAANEVLESIQSYFKSQPFDF--RGAQIISGQEEGVY 185
CD39L4     HWKKTPVVLKATAGLRLL---PEHKAKALLFEVKEIFRKSPFLVPKGSVSIMDGSDEGIL 175
NTPDase4   KHKETPLYILCTAGMRIL--PESQQKAILEDLLTDIPVHFDFLFSDSHAEVISGKQEGVY 222
                                                     ACR IV
CD39       GWITINYLLGKFSQKTRW----------FSIVPYETNNQETFGALDLGGASTQVTFVPQN 234
CD39L1     GWVTANYLLENF---IKY----------GWVGRWFRPRKGTLGAMDLGGASTQITFETTS 215
CD39L2     AWITINFLTGSL----K----------------TPGGSSVGMLDLGGGSTQIAFLPRV 265
CD39L3     GWITANYLMGNF--LEKN---------LWHMWVHPHGVETTGALDLGGASTQISFVAGE 233
CD39L4     AWVTVNFLTGQL----H------------------GHRQETVGTLDLGGASTQITFLPQF 213
NTPDase4   AWIGINFVLGRFEHIEDDDEAVVEVNIPGSESSEAIVRKRTAGILDMGGVSTQIAYEVPK 282

CD39       QTI---ESPDNALQ-----------FRLYGKDYNVYTHSFLCYGKDQALWQKLAKDIQVA 280
CD39L1     PA----EDRASEVQ-----------LHLYGQHYRVYTHSFLCYGRDQVLQRLLASALQTH 260
CD39L2     EGTLQASPPGYLTA-----------LRMFNRTYKLYSYSYLGLGLMSARLAILGGVEGQP 314
CD39L3     KMD---LNTSDIMQ-----------VSLYGYVYTLYTHSFQCYGRNEAEKKFLAMLLQNS 279
CD39L4     EKTLEQTPRGYLTS-----------FEMFNSTYKLYTHSYLGFGLKAARLATLGALETE- 261
NTPDase4   TVSFASSQQEEVAKNLLAEFNLGCDVHQTEHVYRVYVATFLGFGGNAARQRYEDRIFANT 342

CD39       SNE-ILRDPCFHPGYKKVVNVSDLYKTPCT---KRFEMTLPFQQFEIQGIGNYQQCHQSI 336
CD39L1     GF-----HPCWPRGFSTQVLLGDVYQSPCTM-AQRPQNFNSSARVSLSGSSDPHLCRDLV 314
CD39L2     AK--------------D---GKELVSPCL--------SPSFKGEWEHAEVTYRVSGQK 347
CD39L3     PTKNHLTNPCYPRDYSISFTMGHVFDSLCTV-DQRPESYNPNDVITFEGTGDPSLCKEKV 338
CD39L4     GT--------------D---GHTFRSACL---------PRWLEAEWIFGGVKYQYGGNQ 294
NTPDase4   IQK----NR--LLGKQTGLTPDMPYLDPCLPLDIKDEIQQNGQTIYLRGTGDFDLCRETI 396

CD39       LELFNTSYC-PYSQCAFNGIFLPPLQGDFGAFSAFYFVMKFL---NLTSEKVSQEKVTEM 392
CD39L1     SGLFSFSSC-PFSRCSFNGVFQPPVAGNFVAFSAFFYTVDFLR-TSMGLPVATLQQLEAA 372
CD39L2     AAASLHELCAARVSEVLQNRVHRTEEVKHVDFYAFSYYYDLA----AGVGLIDAEKGGSL 403
CD39L3     ASIFDFKACHDQETCSFDGVYQPKIKGPFVAFAGFYYTASAL----NLSGSFSLDTFNSS 394
CD39L4     EGEVGFEPCYAEVLRVVRGKLHQPEEVQRGSFYAFSYYYDRA----VDTDMIDYEKGGIL 350
NTPDase4   QPFMNKTNE---TQTSLNGVYQPPIHFQNSEFYGFSEFYYCTEDVLRMGGDYNAAKFTKA 453
```

Figure 1. (cont)

```
CD39      MKKFCAQPWEEIKTSYAGVKEKY------LSEYCFSGTYILSLLLQGYHFTADSWEHIHF 446
CD39L1    AVNVCNQTWAQLQARVPGQRAR-------LADYCAGAMFVQQLLSRGYGFDERAFGGVIF 425
CD39L2    VVGDFEIAAKYVCRTLETQPQS-------SPFSCMDLTYVSLLLQE-FGFPRSKV--LKL 453
CD39L3    TWNFCSQNWSQLPLLLPKFDEVY------ARSYCFSANYIYHLFVNGYKFTEETWPQIHF 448
CD39L4    KVEDFERKAREVCDNLENFTSG-------SPFLCMDLSYITALLKDGFGFADSTV--LQL 401
NTPDase4  AKDYCATKWSILRERFDRGLYASHADLHRLKYQCFKSAWMFEVFHRGFSFPVNYKS-LKT 512

ACR V
CD39      IGKIQGSDAGWTLGYMLNLTNMIPAEQP-------LSTPLSHSTYVFLMVLFSLVLFTVA 499
CD39L1    QKKAADTAVGWALGYMLNLTNLIPADPPG------LRKGTDFSSWVVLLLLFASALLAAL 479
CD39L2    TRKIDNVETSWALGAIFHYIDSLNRQKSP------AS----------------------- 484
CD39L3    EKEVGNSSIAWSLGYMLSLTNQIPAESPL------IRLPIEPPVFVGTLAFFTVAALLCL 502
CD39L4    TKKVNNIETGWALGATFHLLQSLGISH--------------------------------- 428
NTPDase4  ALQVYDKEVQWTLGAILYRTRFLPLRDIQQEAFRASHTHWRGVSFVYNHYLFSGCFLVVL 572

CD39      IIGLLIFHKPSYFWKDMV------------------------ 517
CD39L1    VLLLRQVHSAKLPSTI-------------------------- 495
CD39L2    ------------------------------------------
CD39L3    AFLAYLCSATRRKRHSEHAFDHAVDSD-------------- 529
CD39L4    ------------------------------------------
NTPDase4  LAILLYLLRLRRIHRRTPRSSSAAALWMEEGLPAQNAPGTL 613
```

Figure 2.

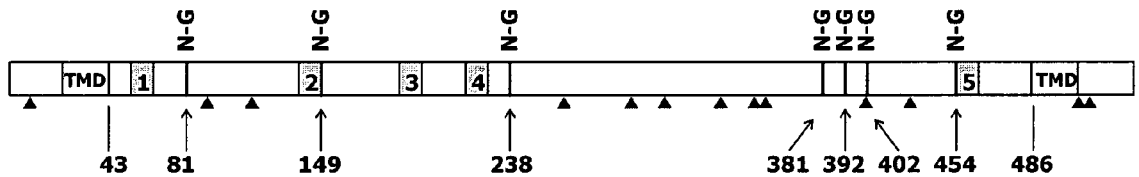

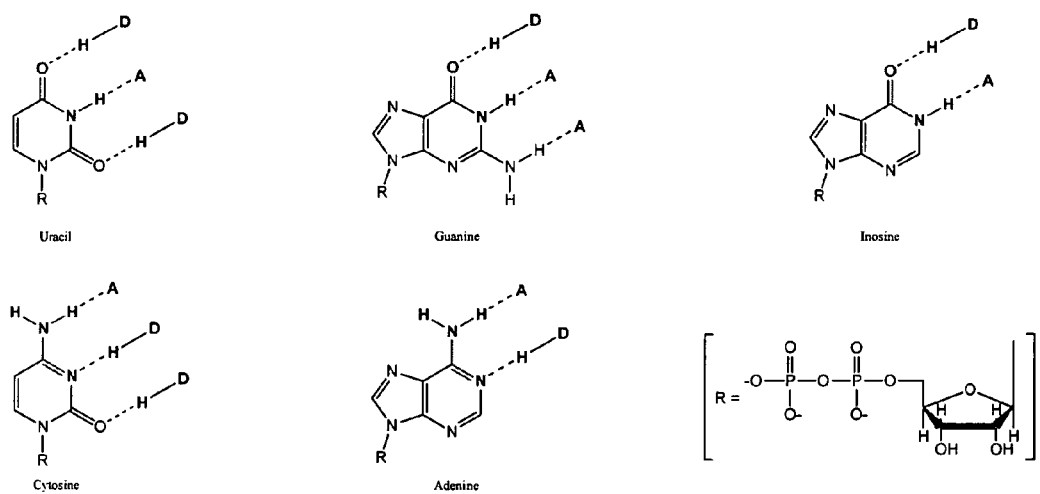

Uracil    Guanine    Inosine

Cytosine    Adenine

```
                                                                Signal
                                                               cleavage
              Igκ leader sequence                                  ↓
ATG GAG ACA GAC ACA CTC CTG CTA TGG GTA CTG CTG CTC TGG GTT CCA GGT TCC ACT GGT / GAC
Met Glu Thr Asp Thr Leu Leu Leu Trp Val Leu Leu Leu Trp Val Pro Gly Ser Thr Gly / Asp Srf I
GCG CCC / GGG CCG ...
Ala Pro   Gly
```

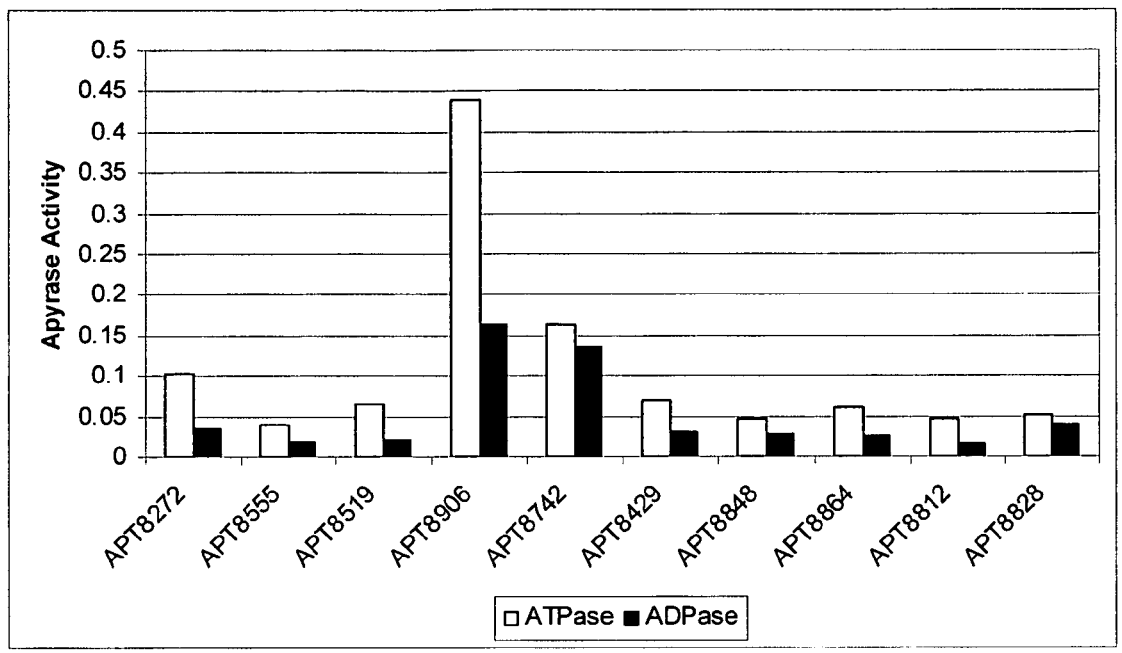
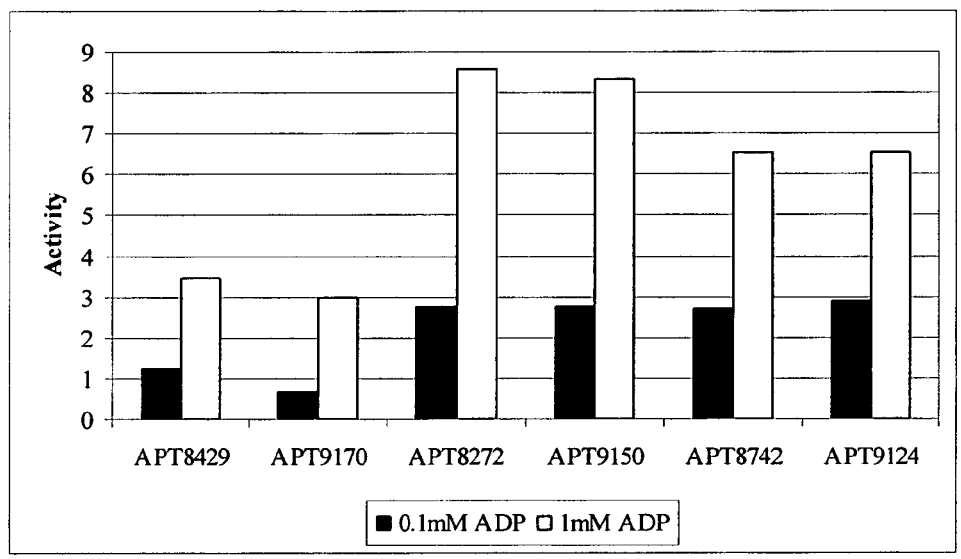

(A) Human Ras/p21 protein (1LF0)

(B) Rat GTP binding protein (1GIL)

(C) Horseshoe Arginine Kinase (1BG0)

(D) Yeast motor ATPase (1F9T)

Figure 15.

```
gi|10443907|Phlebotomus   ------------------------------------------MFLKFC   6
gi|4185746|Cimex          ------------------------------MRSSYRVGNPIRFQPTNV  18
gi|22218108|Human         --------------------------MTKAADPRFRPRWKVILTFF  20
gi|21262131|Rat           MPIQPFDQREWNEPMHSLRISVGGLPVLASMTKATDPRFRPRWRVILTSF  50 gi|10443907|Phlebotomus   IVAFAICLSINLS-----------------------------EG  21
gi|4185746|Cimex          VGLLLLSLVLSFM-----------LVQSYELGHASGETNANSKYPLTTPV  57
gi|22218108|Human         VGAAILWLLCSHR-PAPGRPPTHNAHNWRLGQAP--ANWYNDTYPLSPPQ  67
gi|21262131|Rat           VGAALLWLLYSHHQTPVSGRPPIHNAHNWRLRQER-ISQYNDTYPLSPPQ  99 gi|10443907|Phlebotomus   APRSGTIYNFAITADLDKKSISPKNDNNYKSIVKV--ELIEVGDKYSVK   69
gi|4185746|Cimex          EENLKVRFKIGVISDDDKNAVSKDESNTWVSTYLTGTLEWEKSTDKITVQ  107
gi|22218108|Human         RTPAGIRYRIAVIADLDTESRAQEE-NTWFSYLKKCYLTLSDSGDKVAVE  116
gi|21262131|Rat           RTPGGIRYRIAVIADLDTGSKAQEE-NTWFSYLKKCYLTLSDSGDRVSVE  148 gi|10443907|Phlebotomus   MKK-EDHEIFTKYAYKGRGAELSEFLIYKWKLYTFDDKSGIVFRLKTNAD  118
gi|4185746|Cimex          WDKGNEKKVKSKYSYGGRGMELSELVTFNGNLLTFDDRTGLVYILK-DDK  156
gi|22218108|Human         WDK-DHGVLESHLAEKGRGMELSDLIVFNGKLYSVDDRTGVVYQIE-GSK  164
gi|21262131|Rat           WDK-DRGVLESHLAEKGRGMELSDLIVFNGKLYSVDDRTGVIYQIE-GTK  196 gi|10443907|Phlebotomus   LIPWVTLANGNGDQTDGFKAEWATTKGDKMYVGSTGISFTDKTGKL-NSN  167
gi|4185746|Cimex          VYPWVVLADGDGKNSKGFKSEWATEKAGNLYVGSSGKEWTTKEGTIENYN  206
gi|22218108|Human         AVPWVILSDGDGTVEKGFKAEWLAVKDERLYVGGLGKEWTTTTGDVVNEN  214
gi|21262131|Rat           AVPWVILSDGDCAVEKGFKAEWLAVKDEHLYVGGLGKEWTTTTGEVVNEN  246 gi|10443907|Phlebotomus   SLWIKEIDQDGKVQSLDWKEQYDKIKSAMKI-PNGFIWHEAVNWSKLKNQ  216
gi|4185746|Cimex          PMWVKMINKNGEVTSLNWQTNYEKIRSSMNITFPGYMWHEAACWSDKYNK  256
gi|22218108|Human         PEWVKVVGYKGSVDHENWVSNYNALRAAAGIQPPCYLIHESACWSDTLQR  264
gi|21262131|Rat           PEWVKVVGHRGSVEHENWVSSYNALRAAAGIQPPCYLIHESACWSDTLQR  296 gi|10443907|Phlebotomus   WVFLPRKCSERPFDTKTEETIGCNKIIIASENEEIIKSIQIKGKSINRAA  266
gi|4185746|Cimex          WFFLPRALSQEAYDSKKFETQGANVIISCDDKEEKCEPTQIQ-GKTEDKR  305
gi|22218108|Human         WFFLPRRASQERYSEKDDERKGANLLLSASPDEGDIAVSHV--GAVVPTH  312
gi|21262131|Rat           WFFLPRRASHERYSEREDERKGSNLLLSAAQDERDISVRQV--GALVPTH  344 gi|10443907|Phlebotomus   GFSFKFLPDSDDQILLALKTIEKDDKTATYITVIDITGRVLMPEMQINS  316
gi|4185746|Cimex          GFSNFKFVPTSEDKIIVGLKTVEADDTTETYFTAFDLEGKVLLEETKIDD  355
gi|22218108|Human         GFSSFKFIPNTDDQIIVALKSEEDSGRVASYIMAFTLDGRFLLPETKIGS  362
gi|21262131|Rat           GFSSFKFIPNTDDQIIVALKSEEDNGRIATYVMAFTLDGRFLLPETKIGS  394 gi|10443907|Phlebotomus   DKYEGIVLLKSTEGFLKRSQ  336
gi|4185746|Cimex          HKYEGVDFV----------  364
gi|22218108|Human         VKYEGIEFI----------  371
gi|21262131|Rat           VKYEGIEFI----------  403
```

Figure 16

```
gi|4185746|Cimex     --MRSSYRVGNPIRFQPTNVVGLLLLSLVLSFMLVQSYELGHAS-----GETNAN---SK  50
gi|22218108|Human    MTKAADPRFRPRWKVILTFFVGAAILWLLCSHRPAPGRPPTHNAHNWRLGQAPANWYNDT  60 gi|4185746|Cimex     YPLTTPVEENLKVRFKIGVISDDDKNAVSKDESNTWVSTYLTGTLEWEKSTDKITVQWDK 110
gi|22218108|Human    YPLSPPQRTPAGIRYRIAVIADLDTESRAQEE-NTWFSYLKKGYLTLSDSGDKVAVEWDK 119 gi|4185746|Cimex     GNEKKVKSKYSYGGRGMELSELVTFNGNLLTFDDRTGLVYILKDDKVYPWVVLADGDGKN 170
gi|22218108|Human    -DHGVLESHLAEKGRGMELSDLIVFNGKLYSVDDRTGVVYQIEGSKAVPWVILSDGDGTV 178 gi|4185746|Cimex     SKGFKSEWATEKAGNLYVGSSGKEWTTKEGTIENYNPMWVKMINKNGEVTSLNWQTNYEK 230
gi|22218108|Human    EKGFKAEWLAVKDERLYVGGLGKEWTTTTGDVVNENPEWVKVVGYKGSVDHENWVSNYNA 238 gi|4185746|Cimex     IRSSMNITFPGYMWHEAACWSDKYNKWFFLPRALSQEAYDSKKFETQGANVIISCDDKFE 290
gi|22218108|Human    LRAAAGIQPPGYLIHESACWSDTLQRWFFLPRRASQERYSEKDDERKGANLLLSASPDEG 298 gi|4185746|Cimex     KCEPTQIQGKTEDKRGFSNFKFVPTSEDKIIVGLKTVEADDTTETYFTAFDLEGKVLLEE 350
gi|22218108|Human    DIAVSHV-GAVVPTHGFSSFKFIPNTDDQIIVALKSEEDSGRVASYIMAFTLDGRFLLPE 357 gi|4185746|Cimex     TKIDDHKYEGVDFV 364
gi|22218108|Human    TKIGSVKYEGIEFI 371
```

DESIGN AND THERAPEUTIC USE OF ADPASE ENHANCED APYRASES

CROSS-REFERENCE TO RELATED APPLICATION

This application claims benefit under 35 U.S.C. § 119(e) of provisional application 60/548,344 filed 27 Feb. 2004. The contents of this document are incorporated herein by reference.

The content of the following submission on compact discs is incorporated herein by reference in its entirety: A computer readable form of the Sequence Listing (CRF) (file name: 532602000600, date recorded: Apr. 20, 2005. size: 210,944 bytes); a duplicate compact disc copy of the Sequence Listing (COPY 1) (file name: 53260200060, date recorded: Apr. 20, 2005, size: 210,944 bytes); and a duplicate compact disc copy of the Sequence Listiun (COPY 2) (file name: 532602000600, date recorded: Apr. 20, 2005, size: 210,944 bytes).

TECHNICAL FIELD

The invention relates to the design and use of certain ADPase enhanced apyrases for the prevention and or treatment of thrombotic or ischemic disorders.

BACKGROUND ART

Thrombosis is the formation, development, or existence of a blood clot or thrombus within the vascular system. This is a life saving event when occurs during hemorrhage and a life threatening event when it occurs at any other time. Occlusion of a blood vessel, caused by excessive platelet activation (by the stimulation of an agonist) and recruitment (leading to platelet aggregation and vessel occlusion), are the major contributing factors in clinical disorders such as stroke, myocardial infarction, unstable angina, and restenosis. Therefore, there is a great need to identify therapeutic strategies and compositions for the pharmacological neutralization of platelet reactivity (activation, recruitment, and aggregation).

Currently, several treatment strategies are available to deal with a thrombus formation and fall into two classes, pharmacological (protein based and small molecule bases) and mechanical (for example, percutaneous coronary intervention (PCI), bypass surgery, sonication). The pharmacological classes of treatments cover several therapeutic approaches such as: acting as anti-coagulants (for example, heparin and hirudin), thrombolytic agents (for example, tPA, pro-urokinase, and Streptokinase) or antiplatelet agents (for example, aspirin, ticlopidine, and clopidogel). However, their therapeutic utility is limited due to a significant risk of bleeding complications (Wardlaw, J. M., et al., *Lancet* (1997) 350:607-614). For example, in the United States, less than 2% of the patients with acute ischemic stroke can receive rtPA due to high intracranial hemorrhage risks (Chiu, D., et al., *Stroke* (1998) 29:18-22). Glycoprotein IIb/IIIa antagonists such as ReoPro® (monoclonal antibody) have been used for PCI and are currently under clinical investigation for the treatment of patients with acute coronary syndromes and acute ischemic stroke. However, the inhibition of the glycoprotein IIb/IIIa receptors will interfere with platelet adhesion and clot retraction resulting in bleeding complications. Therefore, it is important to identify novel strategies for inhibition of platelet activation and aggregation that will cause minimal risks of bleeding.

During early stages of platelet activation, several agonist including ADP, Thromboxane $A_2$ and serotonin are released. Among these, ADP is the single most important platelet agonist and recruiting agent that is present in the thrombus microenvironment (Marcus, A. J. and Safier, L. B., *FASEB J.* (1993) 7:516-522). Part of the normal function of endothelial cells ability to maintain blood fluidity is the local generation of an enzyme with ectoapyrase (apyrase, ATP diphosphohydrolase, ATP-diphosphatase, Adenosine diphosphatase, ADPase, E-NTPDase, EC 3.6.1.5) activity such as CD39. CD39 is a constitutively expressed enzyme having apyrase activity that strongly inhibits platelet aggregation by rapidly metabolizing ADP released from activated platelets, thus terminating further platelet recruitment and aggregation. (Marcus, A. J., et al., *J. Clin. Invest.* (1997) 99:1351-1360; Gayle, R., et al., *J. Clin. Invest* (1998) 101:1851-1859). Several research studies have now established CD39 as the prime thromboregulator (Marcus, A. J., et al., supra; Kaczmarek, E., et al., *J. Biol. Chem.* (1996) 271:33116-33122). In addition, animal model studies indicate that administration of a soluble form of CD39 for treatment has significant clinical advantages over existing treatment regimes without the life threatening bleeding complications often associated with the current treatment strategies (PCT WO 01/11949; PCT WO 00/23459).

This invention is directed to the use of ADPase enhanced apyrases, useful for the inhibition of platelet activation and as a general thromboregulator useful for the treatment and prevention of stroke and other diseases involving thrombosis.

DISCLOSURE OF THE INVENTION

The invention is directed to methods to ameliorate or protect against thrombotic disorders by administering ADPase enhanced apyrases or soluble forms thereof. Also provided in the invention are methods of inhibition platelet aggregation by administration of a pharmaceutical composition of ADPase enhanced apyrases. ADPase enhanced apyrases are derived from, for example, CD39, CD39L1, CD39L2, CD39L3, CD39L4, and SCAN-1, that have, increased ADPase and ATPase activity that is increased, decreased or essentially constant or have decreased ATPase activity with no or minor change of ADPase activity. The ADPase enhanced apyrase may be in soluble form and may be supplied as a fusion protein. In one embodiment, the fused sequence targets the soluble ADPase enhanced apyrases to a thrombus.

Similarly, the nucleotide sequences encoding the above mentioned proteins are within the scope of the invention; in some instances, treatment can be effected by administering expression systems for these proteins.

BRIEF DESCRIPTION OF THE DRAWINGS

FIG. 1. (SEQ ID NOS:171-176). Multiple sequence alignment of known human CD39 family using ClustalW (which can be found on the web at: decypher.stanford.edu/index_by_algo.shtml). Apyrase conserved regions (ACR's) are highlighted.

FIG. 2. Scheme for some key structural features of CD39L3. The two transmembrane domains are labeled as TMD located at both the N- and C-termini. The five ACR's are labeled as 1 to 5. The putative N-glycosylation sites are marked with the corresponding residue numbers as set forth in SEQ ID NO: 56) and labeled as N-G. Cysteines are also marked as triangles.

FIG. 3. Structure of the bases in nucleoside diphosphates. Possible hydrogen bond formation is illustrated with hydrogens involved in the binding from the base and the enzyme. A is for enzyme residual side chain of acceptor, D of donor.

FIGS. 8A and 8B show ADPase activity of clot enhanced apyrases derived from CD39 or CD39L3: APT8429, APT9170, APT8272, APT9150, APT8742 and APT9124 (FIG. 8B) and the relative ADPase and ATPase activity of these and additional forms (FIG. 8A).

FIG. 15. (SEQ ID NOS:179-182). Multiple sequence alignment of human SCAN-1 with known apyrases of blood sucking insects (*Phiebotomus* and *Cimex*) and related rat enzyme using ClustalW.

FIG. 16. (SEQ ID NOS:183-184). Paired sequence alignment of human SCAN-1 and *Cimex* apyrase using ClustalW.

MODES OF CARRYING OUT THE INVENTION

Hemostasis and Thromboregulation

Figure 4:
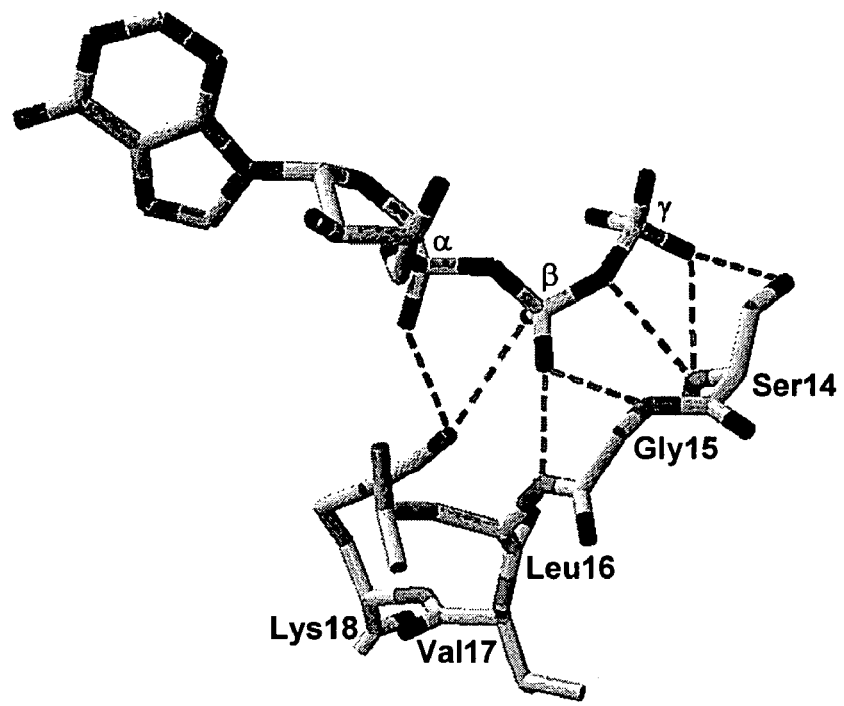
FIG. 4. Structural interaction of rabbit actin with phosphates of ATP.

The hemostatic process represents a series of physiological and biological processes that culminate in the arrest of hemorrhage from blood vessels that have been severed or mechanically traumatized. Hemostasis is accomplished by the action of multiple systems including endothelial cells, blood platelets, and plasma proteins of the intrinsic and extrinsic coagulation systems. Disorders in any or all of the systems can result in defective hemostasis or coagulation resulting in mild to severe hemorrhagic diathesis (Marcus, A. J. (1996) in: Ratnoff, O. D. and Forbes, C. D., eds., *Disorders of Hemostasis*, 3$^{rd}$ ed. Philadelphia: W B Saunders, 79-137). The efficiency of the hemostatic process serves as an agonist for unwanted activation of hemostasis and promotion of blood coagulation. This action results in the misdirected culmination of arterial or venous thrombosis at critical circulation sites such as the coronary or cerebral circulation systems.

Primary hemostatic events occur during interruption of blood vessel continuity by exposure of the subendothelial matrix and more specifically exposed collagen. The exposed collagen is an immediate attractor and agonist of circulating platelet cells (the keystone of the hemostatic arch) and von Willebrand's factor (vWF). During high sheer stress, occurring in small blood vessels or larger vessels with a partial occlusion, vWF plays an important role in generation of the platelet plug. Platelet recruitment is the critical step in the formation of a thrombus and ultimately results in the total occlusion of the vessel by the platelet thrombus. This recruitment is possible by the release of several factors by the platelet including ADP, thromboxane $A_2$, serotonin (5-HT), lysosomal enzymes and growth factors including platelet factor 4. Of these factors ADP has been established as the primary agonist for further platelet recruitment.

Excessive platelet activation and recruitment at site of vascular injury in the coronary, carotid, and peripheral arteries represents a major therapeutic challenge in cardiovascular medicine and results in various occlusive vascular diseases. These ischemic or thrombotic disorders encompass but are not limited to myocardial ischemia, stroke, lung embolism, unstable angina, peripheral vascular disorder, post-angioplasty stenosis and ischemia of other organs. Thromboregulation is defined as a group of processes by which circulating blood cells and cells of the blood vessel wall interact to regulate the formation and development of a thrombus. Thromboregulators are mainly responsible for maintaining blood fluidity and can be classified according to their chronological mode of action in relation to thrombin formation. They can prevent or reverse platelet accumulation, activate coagulation factors, and induce fibrin formation as a result of a hemostatic process. Early thromboregulators such as nitric oxide (NO), eicosanoids (prostacyclin, $PGD_2$) and ecto-ADPase (CD39) inhibit events preceding thrombus formation. Late thromboregulators such as antithrombin III, heparin proteoglycans, tissue factor pathway inhibitor (TFPI), thrombomodulin-protein-C-protein S pathway, and fibrinolytic proteins exhibit effects after thrombin formation. Many of these defense systems can be overwhelmed by the agonistic activities resulting from vascular injury.

CD39 is a Key Thromboregulator in Humans

ADP is the most critical agonist of platelet aggregation present in the activated platelet releasates. Hydrolysis (metabolism or catabolism) of ADP to AMP by the action of the thromboregulatory ecto-ADPase (such as CD39) blocks further recruitment and activation of additional platelets to the thrombus site and effectively reverses the aggregation response and blocks further thrombus formation. CD39 (cluster of differentiation 39) is a cell surface molecule that is recognized by a cluster of monoclonal antibodies that are useful in distinguishing one class of lymphocytes from another. CD39 is a 510 amino acid peptide (also reported as a 517 amino acid peptide Genbank: gi: 21361569)) with a predicted mass of 57 kDa. However, CD39 displays a molecular mass of approximately 100 kDa due to extensive N-glycosylation (Maliszewski, C. R., et al., *J. Immunol.* (1994) 153:3574). CD39 contains two hydrophobic transmembrane domains located at the N-terminus and C-terminus. Recently, a truncated form of CD39 resulting in a soluble peptide retaining the same nucleotidase activity as the wild type was produced by removing the hydrophobic transmembrane domains at both the N-terminus and C-terminus (Gayle, R. B., et al., *J. Clin Invest.* (1998) 191:1851). It has also been demonstrated that the soluble form of CD39 is capable of blocking ADP induced platelet aggregation and inhibit collagen-induced platelet reactivity in vitro. (Gayle, R. B., et al., *J. Clin. Invest.* (1998) 101:1851-1859). Animal model studies with CD39 null (CD39–/–) mice (prothrombotic phenotype) have also indicated that administration of the soluble form of CD39 is an effective therapeutic agent for thrombotic stroke. (Marcus, A. J., et al., *Ital. Heart J.* (2001) 2:824-830.) Hence, CD39 or CD39-like enzymes can be used to prevent or treat platelet-driven occlusive vascular diseases.

Human CD39 Apyrase Family

CD39 is a member of the E-NTPase protein family that hydrolyse either nucleoside 5'-triphosphates or both nucleoside 5'-tri- and diphosphates. Currently there are several vertebrate members of the E-NTPase gene family that are grouped according to their phylogenetic relationships. These include but are not limited to NTPDase1 (CD39) (Christoforidis, S., et al., *Eur J Biochem* (1995) 234:66-74; Kaczmarek, E., et al., *J Biol Chem* (1996) 271:33116-33122; Maliszewski, C. R., et al., *J Immunol* (1994) 153:3574-3583; Marcus, A. J., et al., *J Clin Invest* (1997) 99:1351-1360; Matsumoto, M., et al., *FEBS Lett* (1999) 453:335-340; Sévigny, J., et al., *Biochim Biophys Acta* (1997) 1334:73-88; Wang, T. F. and Guidotti, G., *J Biol Chem* (1996) 271:9898-9901), NTPDase2 (CD39L1) (Chadwick, B. P., and Frischauf, A. M., *Mamm Genome* (1997) 8:668-672; Kegel, B., et al., *Neuropharmacology* (1997) 36:1189-1200; Kirley, T. L., *J Biol Chem* (1997) 272:1076-1081), NTPDase3 (CD39L3) (Chadwick, B. P., and Frischauf, A. M., *Genomics* (1998) 50:357-367; Smith, T. M., and Kirley, T. L., *Biochim Biophys Acta* (1998) 1386:65-78), NTPDase (UDPase) (Wang, T. F., and Guidotti, G., *J Biol Chem* (1998) 273:11392-11399), NTPDase (CD39L4) (Chadwick, B. P., and Frischauf, A. M., *Mamm Genome* (1997) 8:668-672; Chadwick, B. P., and Frischauf, A. M., *Genomics* (1998) 50:357-367; Chadwick, B. P., et al., *Mamm Genome* (1998) 9:162-164; Mulero, J. J., et al., *J Biol Chem* (1999) 274:20064-20067), and NTPDase6 (CD39L2) (Chadwick, B. P., and Frischauf, A. M., *Mamm Genome* (1997)8: 668-672; Chadwick, B. P., and Frischauf, A. M., *Genomics* (1998) 50:357-367; Chadwick, B. P., et al., *Mamm Genome* (1998) 9:162-164). For example, CD39 hydrolyzes ATP and ADP at a molecular ratio of about 1:0.5. In contrast, CD39L1 has a strong preference for ATP with molecular ratio of ATP:ADP of 1:0.03. CD39L3 is a functional intermediate and reveals a molecular ratio of ATP:ADP of approximately 1:0.3. CD39L4 reveals highest activity with GDP as a substrate. CD39L2 and CD39L5 have the highest activity with UDP.

In addition the membrane topography of the currently known mammalian members of the E-NTPase family have been characterized. (Zimmermann, H., *Tips* (1999) 20:231-236). All members share five highly conserved sequence domains (apyrase conserved region, ACR) that presumably are relevant for their binding and catalytic activity (FIG. 1).

CD39L3 is an Isozyme of CD39

Among the known human CD39 family, CD39L3 is known as an ecto-apyrase (ecto-ATPDase) with biochemical activity between CD39 (ecto-ATDPase) and CD39L1 (ecto-ATPase). Smith and Kirley (*Biochemica et Biophysica Acta* (1998) 1386:65-78) determined CD39L3 is found primarily in human brain tissue.

Specifically CD39L3 is a 529 amino acid protein with a predicted molecular weight of 59132.42 Daltons. The isoelectric point of CD39L3 is 6.233. There are seven putative glycosylation sites and 13 cysteine residues. Based on SEQ. ID. NO: 56, the N-terminal 43 residues and C-terminal 44 residues are considered to be part of a transmembrane domain. The catalytic core of the enzyme roughly resides between amino acid 44 through amino acid 238 (FIG. 2).

ProtParam analysis shows that both CD39L3 and CD39 are composed of about 520 amino acids with the pI of about 6.0. CD39L3 and CD39 also share similar amino acid compositions to each other and common structural motifs including about 440 amino acid residues of the extracellular ATP/Dase portion that resides between the N- and C-terminal transmembrane regions. Although CD39L3 is found in chromosome 3 and CD39 in chromosome 10, their overall intron and exon structures are identical with 10 exons each.

Pairwise sequence alignment of CD39L3 and CD39 shows about 35% sequence identity. Although the overall sequence identity is low the key amino acid residues involved in catalysis, substrate binding and structural motifs are highly conserved. For example, the majority of the sequence identity between CD39L3 and CD39 can be accounted for conservation in the apyrase conserved regions (ACR's). ACR's determine the number of phosphates hydrolyzed from the phosphate binding site of the nucleotide substrates. In addition, key residues between ACR4 and ACR5 that specify base binding (for example, adenine) are conserved and residues for structure formation (such as Cys, Pro, and Gly) are also absolutely conserved.

Bioinformatics analysis suggests that CD39L3 is a brain specific isozyme or isoenzyme of CD39. Isozymes or isoenzymes may not have the same regulatory properties of their respective counterpart, but rather have adjusted their enzymatic properties to be optimal for the precise environment to which they are subjected. Northern blot studies showed CD39L3 is highly expressed in brain and kidney, while CD39 is expressed in placenta and spleen. The analysis suggests that expression of the isoenzyme CD39L3 in human brain complements the activity of CD39 as the key thromboregulator.

Additional Enzymes Useful in the Present Invention

CD39 family members represent some of the best characterized apyrases. However, there are also other apyrase like families which are not homologous to the CD39 family with respect to their amino acid sequences, and it appears that these families are also evolutionarily unrelated to each other.

An apyrase (EC 3.6.1.5) catalyzes the hydrolysis of phosphoanhydride bonds of adenosine triphosphate (ATP) to adenosine monophosphate (AMP) using two molecules of water (Reaction 1) and adenosine diphosphate (ADP) to AMP using one molecule of water (Reaction 2). There is no reported evidence for the further hydrolysis of AMP by apyrase enzymes. Certain apyrase enzymes also can hydrolyze other nucleoside triphosphate including but not limited to GTP, CTP, UTP, and other nucleoside diphosphates including but not limited to GDP, CDP, UDP with different degrees of the substrate preference. For all the hydrolysis reactions the apyrase enzyme requires either calcium or magnesium as co-substrate (Zimmerman, H., *TIPS* (1999) 20: 231-236).

| Apyrase (EC 3.6.1.5) | |
|---|---|
| (Reaction 1) | ATP + 2.H$_2$O → AMP + 2 phosphate |
| (Reaction 2) | ADP + H$_2$O → AMP + phosphate |

In the human genome sequence, several putative apyrases have been reported based on protein sequence homology with known apyrases found in non-human species such as blood-sucking insects. For example, human soluble calcium-activated nucleotidase (SCAN gi: 20270339; SCAN-1 gi: 22218108; EC 3.6.1.6) (Smith, et al., *Arch. Biochem. Biophys.* (2002) 406:105-115) has sequence homology with the bed bug *Cimex lectularius* apyrase (gi: 4185746) (Valenzuela, et al., *J. Biol. Chem.* (1998) 273:30583-30590). Also the human 5'-nucleotidase (gi: 33520072; EC 3.1.3.5) has sequence homology with the mosquito *Aedes aegypti* apyrase (gi: 1703351) (Champagne, et al., *Proc. Natl. Acad. Sci. USA* (1995) 92:694-698). Still further, the human inositol polyphosphate 5'-phosphatase (gi: 346209; EC 3.1.3.56) has homology to the *Rhodnius prolixus* apyrase (gi: 1546841) (Sarkis, et al. *Biochem. J.* (1986) 233:885-891). Although they were annotated as apyrases based merely on the sequence alignment, many of the enzymes listed supra have insufficient activity for ATP and/or ADP hydrolysis. Therefore to fully utilize those human and non-human enzymes in the present invention as apyrases, protein engineering may be required to re-design their substrate specificity from other nucleotide (for example CTP, UTP, GTP, CDP, UDP, and GDP) to ADP and/or ATP and ADP.

Therefore we envision that following enzymes have potential activities of apyrases and are useful in the present invention.

Nucleoside-diphosphatase (EC 3.6.1.6) (Reaction 3) NTP+H$_2$O→NDP+phosphate

5'-Nucleotidase (EC 3.1.3.5)

(Reaction 4) 5'-Ribonucleotide+H$_2$O→Ribonucleoside+phosphate

Inositol-polyphosphate 5-phosphatase (EC 3.1.3.56)

(Reaction 5) D-Myo-inositol 1,4,5-triphosphate+H$_2$O→Myo-inositol 1,4-bisphosphate+phosphate For example, for human SCAN-1 (gi: 22218108; EC 3.6.1.6) the enzymatic activity of UDPase, GDPase and IDPase was 20 to 30 fold higher than the ADPase activity (Km of 0.46 mM for GDP and 5.4 mM for ADP) (Smith, et al., *Arch. Biochem. Biophys.* (2002) 406:105-115). Therefore it is unlikely that wild type human SCAN-1 can efficiently catalyze the conversion of micromolar range of ADP released from activated platelets under physiological conditions. Therefore one skilled in the art can effectively engineer, for example, an ADPase enhanced SCAN-1 apyrase by changing the substrate specificity of NDPases, more specifically, the base specificity of the nucleotides such as ADP. As illustrated in FIG. 3, for example, a common feature of the natural substrates of NDPases (for example UDP, GDP and IDP), is the cis peptide bond in their pyrimidine or purine ring and that is not present in poor substrates (for example ADP and CDP). Therefore one skilled in the art can identify the discrepancy in hydrogen bond formation between the bases of the nucleotides and the residues in enzyme active sites and can alter the identified enzyme residues to those favorable to forming hydrogen bonds with ADP. In another way the base specificity may also be altered by one skilled in the art by introducing different hydrophilic, hydrophobic or aromatic residues in the nucleotide binding pocket of the enzyme. Alternatively substrate specificity for ADP can be achieved by fusing or swapping certain domains or regions of human SCAN-1 with the appropriate counterpart of apyrase enzymes that naturally have the preferred ADPase activity (for example, *Cimex lectularius* apyrase (gi: 4185746)).

Besides altering base specificity, in the example of human SCAN-1, there are other intrinsic features (for example, pH optimum, protein half life, kinetic parameters) that may be necessary to gain full therapeutic effect under physiological conditions (for example in the human blood stream). In the kinetic study of human SCAN-1 (Murphy, et al., *Biochemistry* (2003) 42:2412-2421), the optimum pH for enzymatic activity was determined to be between pH 6 and pH 7 with an absolute requirement of calcium for activity. The enzyme kinetic behavior also represents a sigmoid curve indicating allosterism instead of a hyperbolic curve representing independent substrate binding. Therefore one skilled in the art can engineer enzymes, for example SCAN-1, with a preferred pH optimum such as pH 7.4 and without allosterism by rationally or randomly changing amino acid residues having different charge, polarity, hydrophilicity, hydrophobicity, aromaticity or size. One can also envision adding or removing ligands or polypeptides to change the optimum pH and allosterism. One can further envision that poor activity under physiological condition can be overcome by improve kinetic parameters such as $k_{cat}$/Km by altering catalytic residues within the enzymes active site.

Other enzymes potentially useful in the present invention include wild type and engineered forms of enzymes catalyzing the hydrolysis of inorganic phosphate in phosphorous-containing anhydrides under group EC 3.6.1.-. More specifically, the following enzymes, as examples, can catalyze ATP and/or ADP hydrolysis to various degrees.

Adenosinetriphosphatase (aka ATPase; EC 3.6.1.3)

(Reaction 6) ATP+H$_2$O→ADP+phosphate

Nucleoside-diphosphatase (EC 3.6.1.6)

(Reaction 7) NDP+H$_2$O→NMP+phosphate

ATP diphosphatase (EC 3.6.1.8)

(Reaction 8) ATP+H$_2$O→AMP+diphosphate

Nucleotide diphosphatase (EC 3.6.1.9)

(Reaction 9) Dinucleotide+H$_2$O→2 Mononucleotide

Nucleoside-triphosphatase (EC 3.6.1.15)

(See Reaction 3)

Nucleotide-triphosphate diphosphatase (EC 3.6.1.19)

(Reaction 10) NTP+H$_2$O→NMP+diphosphate

Guanosine-diphosphatase (EC 3.6.1.42)

(Reaction 11) GDP+H2O→GMP+phosphate

ADPase Enhanced Apyrases

The ADPase enhanced apyrases of the invention are modified forms of apyrases that occur in nature. The modifications are typically focused on positions in the native forms which are particularly critical for the catalytic activity. For illustrative purposes, an individual native apyrase may be modified by, for example, an amino acid substitution or deletion at a particular position in the amino acid sequence. Corresponding modifications can be made in the isoenzymes of the same family where the corresponding position is similarly modified. By "corresponding position" is meant the position which aligns with the reference position when the overall amino acid sequences are appropriately aligned to assure homology of at least consensus sequences. For example, as shown in FIG. 1, the sequences of the members of the CD39 family as well as NTDase-4 are aligned and consensus sequences of the apyrase conserved regions (ACR's) are highlighted. As seen in FIG. 1, for example, position 184 of CD39 corresponds to position 168 of CD39L1, position 227 of CD39L2, position 185 of CD39L3, and so forth. Thus, successful modifications in an illustrative member of an isoenzyme family informs the design of corresponding modifications in other members of the same family or, as shown, other apyrases which can be aligned with the reference protein.

As used herein "isoenzyme" refers to an enzyme with similar activity to a reference enzyme which is sufficiently homologous in sequence that consensus sequences can be matched, in a manner similar to that shown in FIG. 1.

Animal studies clearly demonstrated the promising therapeutic utility of intravenously injected solCD39 in acute ischemic stroke (AIS) by reducing thrombosis, neurological deficit and mortality (Pinsky, et al., *J. Clin Invest.* (2002) 109:1031-1040; Belayev, L., et al., *Stroke* (2003) 34:758-763). However, these particular studies only demonstrated that statistically significant benefits can be were observed with a dosage of 4 to 8 mg/kg. This dosage may create commercial barriers in terms of manufacturing cost, administration and safety. Effective strategies to overcome these commercial barriers may be to improve the catalytic efficiency of the enzyme or to improve the therapeutically effective activity (ADPase activity) of the enzyme. Effectively, ADPase enhanced apyrases are apyrases that have, increased ADPase wherein the ATPase activity is increased, decreased or essentially constant as compared to the native apyrase, or may have decreased ATPase activity with minor change of ADPase activity.

While all four types of ADPase enhanced apyrases may effectively overcome key commercial barriers in terms of dosage, embodiments with decreased ATPase activity may also have the added benefit of minimizing potential side effects due to systemic removal of ATP in, for example, circulating plasma. Several methods are available to alter the biochemical properties of proteins including, site directed mutagenesis (for example, domain swapping, amino acid deletion(s), amino acid insertion(s), or amino acid substitution(s)) and random mutagenesis (for example, error prone PCR, DNA shuffling, in vivo mutagenesis). Alterations to produce ADPase-enhanced apyrases typically involve the catalytically active region which, in the case of CD39L3 is between residues 44 and 238, and will reside in corresponding regions in other members of the C39 isoenzyme (or ecto—NTPase) family. The apyrase conserved regions (ACR's) (1-5) of these enzymes can be modified, in particular ACR1 and/or ACR4 as well as the region between ACR4 and ACR5. As noted in FIG. 1, these ACR's show enhanced homology among the members of the family and occur at what is defined as "corresponding" positions in each protein. Particular amino acids within these regions have also been identified as suitable candidates for substitution.

ADPases with Increased ADPase Activity

Figure 5:
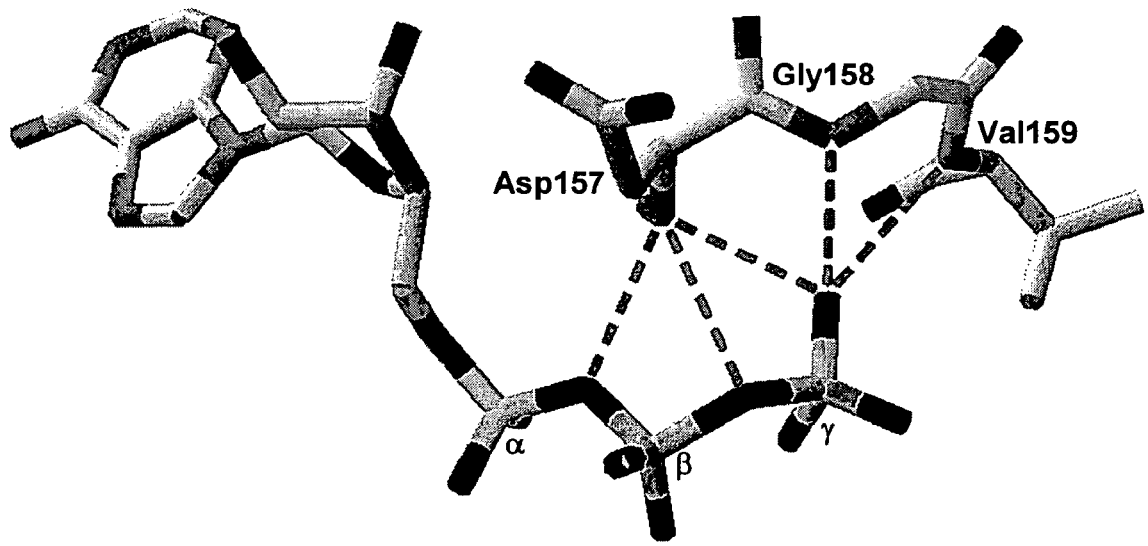
FIG. 5. Structural interaction of rabbit actin with phosphates of ATP.
Figures 6, 7:
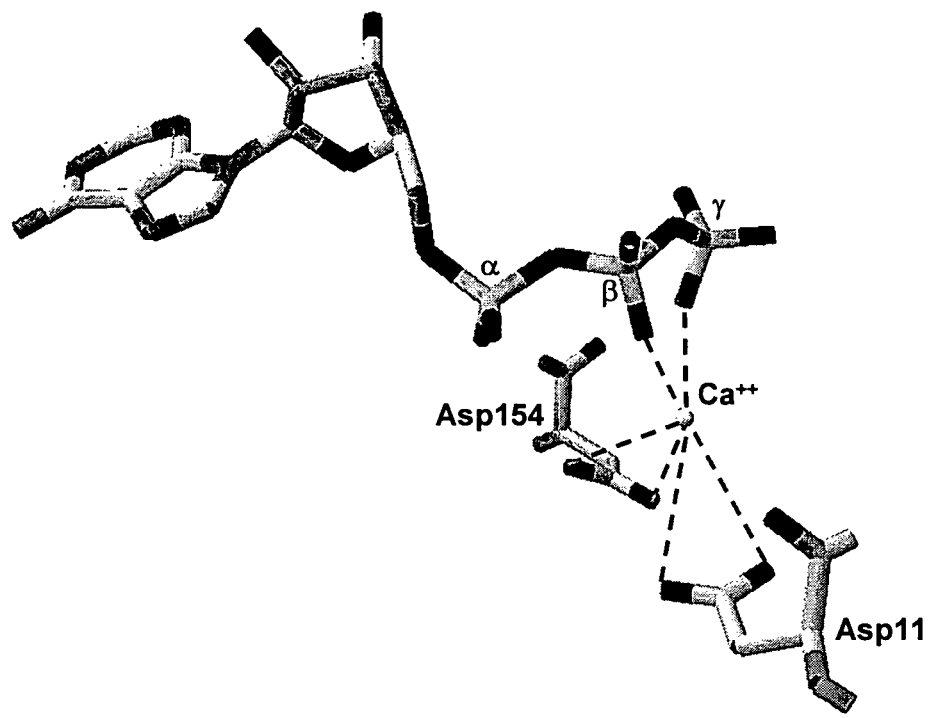
FIG. 6. Structural interaction among rabbit actin, ATP and calcium ($Ca^{++}$).
FIG. 7. (SEQ ID NOS:177-178). A graphic representation of the Igκleader sequence with the introduced SrfI restriction enzyme used to translationally fuse the SmaI fragments comprising the respective apyrase genes. Proper post-translational processing of the signal peptide will introduce Asp-Ala-Pro-Gly to the N-terminus of the respective apyrase genes.

PSI-BLAST search suggests the E-NTPDases (for example CD39, CD39L1, CD39L2, CD39L3, CD39L4, and NTPDase4) are distantly related to a number of other ATP hydrolyzing proteins such as actin, HSP-70 and hexokinase. Both classes of enzyme hydrolyze nucleotide phosphates (for example (ATP and ADP) and require calcium as a cosubstrate. A large number of crystal structures have been solved for the ATP hydrolyzing class of enzymes but no crystal structures are currently available for the E-NTPDase family. For example, the crystal structure of rabbit actin shows that ADP and ATP is located in the cleft between two domains with a calcium ion bound to the $\beta$- or $\beta$- and $\gamma$-phosphates, respectively (Kabsch, W., et al., *Nature* (1990) 347:37-44). Based on the crystal structure information, the phosphate groups of ADP and ATP are involved in a large number of interactions (FIGS. 4, 5 and 6). For example, in the case of ATP binding, the $\epsilon$-amino group of Lys18 of actin forms bifurcated hydrogen bonds with the O2-atom of the $\alpha$-phosphate and the O1-atom of the $\beta$-phosphate. Additionally, the $\beta$- and $\gamma$-phosphates are involved in hydrogen bonds with amides of residues Ser14, Gly15, and Leu16 (FIG. 4) and residues Asp157, Gly158, Val159, (FIG. 5) respectively.

Although there is no overall sequence identity between actin and E-NTPases, it is possible to map the ACR I and ACR IV motifs onto the three-dimensional structure of rabbit actin (Table 1). Table 1 shows that those motifs (ACR I and ACR 4) correspond to highly conserved structural elements involved in $\beta$- and $\gamma$-nucleotide phosphate binding. The key binding residues Ser14 (candidate catalytic residue) and Asp11 and Asp154 (key residue involved in calcium binding (FIG. 6)) are highly conserved (underlined residues Table 1) throughout the entire class of enzymes indicating that the alignments can be confidently assigned to the known crystal structure for rabbit actin. Therefore one skilled in the art can identify key residues involved in ATP and ADP binding by sequence comparison among the super family members. Specifically residues indicated in Table 1 (bold residues) are key residues most likely involved in binding of ATP and ADP and amino acid substitutions at these positions are likely to result in improved affinity for ATP and ADP.

TABLE 1

Structure based sequence alignment of the actin/HSP70 superfamily

| Enzyme | Specificity | ACR I | SEQ ID NO: | ACR IV | SEQ ID NO: |
|---|---|---|---|---|---|
| Rabbit Actin | ATP | LVCDNGSGLVKAGFA | 143 | GIVLDSGDGVTHNVP | 144 |
| Human Actin | ATP | LVCDNGSGLVKAGFA | 145 | GIVLDSGDGVTHNVP | 146 |
| Human HSP70 | ATP | VGIDLGTTYSCVGVF | 147 | VLIFDLGGGTFDVSI | 148 |
| NTPDase1 (CD39) | ATP/ADP | IVLDAGSSHTSLYIY | 149 | FGALDLGGASTQVTF | 150 |
| NTPDase2 (CD39L1) | ATP | IVLDAGSSHTSMFIY | 151 | LGAMDLGGASTQITF | 152 |
| NTPDase3 (CD39L3) | ATP/ADP | IVLDAGSSRTTVYVY | 153 | TGALDLGGASTQISF | 154 |

TABLE 1-continued

Structure based sequence alignment of the actin/HSP70 superfamily

| Enzyme | Specificity | ACR I | SEQ ID NO: | ACR IV | SEQ ID NO: |
|---|---|---|---|---|---|
| NTPDase4 (UDPase) | UDP | IVVDCGSSGSRVFVY | 155 | AGILDMGGVSTQIAY | 156 |
| NTPDase5 (CD39L4) | UDP | IMFDAGSTGTRIHVY | 157 | VGTLDLGGASTQITF | 158 |
| NTPDase6 (CD39L2) | UDP | IMFDAGSTGTRVHVF | 159 | VGMLDLGGGSTQIAF | 160 |

ADPase with Reduced ATPase Activity

Enzymatic studies show that solCD39 hydrolyzes ATP two-fold more efficiently than ADP and the in vivo rates of ATP and ADP hydrolysis will be a function of their respective concentrations. Thus, when the concentration of ATP is high compared with ADP, net ADP formation occurs. This raises the possibility that intermediate ADP may further promote platelet aggregation (Birk, et al., *J. Lab. Clin. Med.* (2002) 140:166-175). Hence, reducing ATPase activity of apyrases and retaining or enhancing the therapeutically beneficial ADPase activity may have greater potential for reversing platelet reactivity in prothrombotic states resulting in an improved safety profile.

Residues determining specificity of ATP and ADP can be identified by sequence comparison among apyrase family members. For example, two studies were conducted, both concluding the specificity determinants for nucleotide binding specificity are localized to the C-terminus of the protein and lie outside of ACR 4 and 5. The first study was conducted using rat NTPDase 1 and NTPDase 2 (Heine, P., et al., *Eur J Biochem* (2001) 268:364-373) and the second study was conducted using *Toxoplasma* nucleoside triphosphate hydrolases NTPase 1 and NTPase 3 (Nakaar, V., et al., *Mol. Biochem. Parasito.* (1998) 97:209-220). Therefore, domain swapping of the region between ACR 4 and ACR 5 remains a viable strategy to alter nucleotide phosphate binding specificity. Alternatively one could envision modifications such as insertions, substitutions, or deletions that could further alter the binding of the nucleotide tri-phosphate such as increasing the bulk of the pocket or introduce negative charged amino acids to repel the binding of the nucleotide triphosphate, for example ATP.

Utility of ADPase Enhanced Apyrases

Agents that regulate the process of thrombosis, especially platelet aggregation have potential utility in treating occlusive vascular diseases. Because ADP is the most important agonist of platelet aggregation, and is present in activated platelet releasate, an agent that metabolizes ADP is useful for treating disease involving inappropriate activation and aggregation of platelets. The present invention refers to the use of ADPase enhanced apyrases, more preferably the use of a biologically active soluble form of ADPase enhanced apyrases for the treatment and prevention of thrombotic disorders.

Examples of therapeutic uses of ADPase enhanced apyrases and biologically active derivatives include but are not limited to, for example, treatment of individuals who suffer from stroke, coronary artery disease or injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders including lung ischemia, coronary ischemia and cerebral ischemia, thrombotic disorders including, coronary artery thrombosis, cerebral artery thrombosis, intracardiac thrombosis, peripheral artery thrombosis, and venous thrombosis.

Other examples in which it would be useful to inhibit ADP induced platelet stimulation would be in individuals at high risk for thrombus formation or reformation including those at risk for advanced coronary artery diseases, and patients undergoing angioplasty procedures (including, for example, balloon, laser, or similar techniques), Inhibition of ADP induced platelet aggregation would be beneficial in patients undergoing surgery with high risks of thrombus formation, including, for example, organ transplantation, coronary bypass surgery, prosthetic valves or vessel transplantation. In addition, the ability of ADPase enhanced apyrases to inhibit platelet activation and recruitment is useful for treatment and or prevention of deep vein thrombosis (DVT), pulmonary embolism (PE), transient ischemic attacks (TIA's) and strokes due to vascular occlusion.

Antiplatelets are currently used for prevention of acute cardiac ischemic complications in angioplasty patients. Currently there are three marketed injectable antiplatelet drugs (GPIIb/IIIa receptor inhibitors): Centocor and Lilly's Reopro® (abciximab), Merck's Aggrastat® (tirofiban) and Schering-Plough and Millenium's Integrilin® (eptifibatide). It has been demonstrated that the use of GP IIb/IIIa inhibitors leads to substantial reductions in rates of urgent target vessel revascularization (Eisenberg, M. J., and Jamal, S., *J Am Coll Cardiol* (2003) 42:1-6). Alternatively, immunosuppressant can be coated on stent to provide antiproliferative benefits. Due to its potent antiplatelet effect and potential anti-inflammatory properties, the adjunction of apyrases to PCI may represent a highly competitive alternative to adjunctive use of antiplatelet agents or coated stents.

ADPase enhanced apyrases may be used to screen for inhibitors of the enzyme activity. Such inhibition may be competitive, uncompetitive, or noncompetitive inhibitions in the presence of the substrates ATP and ADP. Alternatively an inhibitor can inhibit ADPase enhanced apyrases by binding to allosteric sites. All these inhibitors can be analyzed with soluble ADPase enhanced apyrases or biologically active derivatives in the presence of substrate.

ADPase enhanced apyrases and biologically active derivatives may be used in clinical situations where the hydrolysis of ATP and/or ADP to AMP is clinically beneficent including disease states where ATP and/or ADP concentrations are abnormally high.

In addition, ADPase enhanced apyrases and biologically active derivatives may be administrated in combination with currently available antithrombotic or thrombolytic agents, such as heparin, aspirin, glycoprotein IIb/IIIa antagonist, and recombinant tissue type plasminogen activator (t-PA).

ADPase Enhanced Apyrase Polypeptides

As used herein, the term "ADPase enhanced polypeptides" includes, homologs of, variants of, fragments of, and derivatives of ADPase enhanced apyrases, fusion polypeptides comprising ADPase enhanced apyrases, and soluble forms of ADPase enhanced apyrase polypeptides. For example ADPase enhanced apyrases listed in Table 3 (Example 6).

The term "biological activity," as used in herein, includes ADPase enhanced apyrase enzymatic activity as well as the ex vivo and in vivo activities of ADPase enhanced apyrases. Apyrases catalyze the hydrolysis of nucleoside tri- and/or di-phosphates, but a given apyrase may display different relative specificities for either nucleoside triphosphates or nucleoside diphosphates. Biological activity of soluble forms of ADPase enhanced apyrases may be determined, for example, in an ecto-nucleotidase or apyrase assay (e.g., ATPase or ADPase assays), or in an assay that measures inhibition of platelet aggregation. Exemplary assays are disclosed herein; those skilled in the art will appreciate that other, similar types of assays can be used to measure biological activity or enzymatic activity.

The key enzymatic activity of ADPase enhanced apyrases resides in the extracellular region; therefore one skilled in the art can effectively engineer a soluble form of ADPase enhanced apyrases by removing, for example, the transmembrane domains. The N-terminal and C-terminal regions of the CD39 family of isoenzymes constitute the transmembrane regions and deletion or alteration of one or both of these sequences results in soluble forms of the catalytically active protein. In CD39, the 37 amino acids at the N-terminus and 33 amino acids at the C-terminus are typically those representing transmembrane regions which should be removed or otherwise altered; for CD39L3 the N-terminal 43 amino acids and C-terminal 44 amino acids correspond to the transmembrane regions. The corresponding positions in the remaining members of the CD39 isoenzyme family are similarly deleted or otherwise altered to result in the soluble form of the protein. In CD39L4, the corresponding region at the N-terminus is the N-terminal 19 amino acids. One or both of the N-terminal or C-terminal regions are deleted to obtain the desired form.

Rather than deletion, one skilled in the art can effectively replace the amino acid residues comprising the hydrophobic transmembrane domains with amino acid residues such as, for example, serine, glutamic acid, aspartic acid, lysine, arginine, histidine, asparagines, and glutamine that may effectively generate a soluble polypeptide. It is also envisioned that one skilled in the art will be able to generate permutations and combinations of ADPase enhanced apyrases that will effectively render the protein soluble and include but are not limit to deletions of transmembrane domains, substitutions of transmembrane domains, partial deletions or substitutions of transmembrane domains, or polypeptide fusions with proteins or amino acid sequence known in the art to be soluble. Soluble polypeptides are polypeptides being able to be secreted from the host cells in which they are expressed. A secreted soluble polypeptide can be identified (and distinguished from its non-soluble membrane-bound counterparts) by separating intact cells that expressed desired polypeptide from the culture medium, e.g., by centrifugation or filtration, and assaying the medium (supernatant or filtrate) for the presence of the desired polypeptide. The presence of the desired polypeptide in the medium indicates that the polypeptide was secreted from the host cells and therefore is a soluble form of the polypeptide. The use of soluble forms of ADPase enhanced apyrases is advantageous for many applications including but not limited to protein purification, biological reactions, therapeutics, and enzymatic reactions.

Also included within the scope of the invention are fusion polypeptides of ADPase enhanced apyrases and soluble biologically active derivatives that occur at the N-terminal domain, C-terminal domain, or both N-terminal and C-terminal domains. One normally skilled in the art can design fusion polypeptides with ADPase enhanced apyrases and soluble biologically active derivatives of ADPase enhanced apyrases to, for example, simplify protein purification, provide immunological tag, stabilize protein, increase translational efficiency, direct synthesized protein to a particular compartment in the cell, secrete the synthesized protein outside the cell, target the protein to a particular location or cell type, or region of the human or mammalian body, or alter tertiary and quaternary structure of the enzyme.

For example, several strategies are known in the art for generating fusion polypeptide to the N-terminal or C-terminal domains of ADPase enhanced apyrases to aid in the purification of CD39L3 peptides. Such peptides include, for example, poly-His (6XHIS), Glutathione S-transferase (GST), maltose binding protein (MBP), and FLAG® peptide. Such sequences may also be used for identification of expressed recombinant protein using antibodies or can be removed from the recombinant protein using specific protease cleavage sites.

As another example, a fusion polypeptide comprising ADPase enhanced apyrases and biologically active derivatives may contain a signal peptide (which is also variously referred to as a signal sequence, signal, leader peptide, leader sequence, or leader) which co-translationally or post-translationally directs transfer of the polypeptide from its site of synthesis to a site inside or outside of the cell membrane or cell wall. It is particularly advantageous to fuse a signal peptide that promotes extracellular secretion to the N-terminus of a soluble ADPase enhanced apyrase polypeptide. In this case, the signal peptide is typically cleaved upon secretion of the soluble ADPase enhanced apyrase from the cell.

In another embodiment, one or more amino acids are added to the N-terminus of a soluble ADPase enhanced apyrase polypeptide in order to improve the expression levels and/or stability of the ADPase enhanced apyrase polypeptide.

In another embodiment, a soluble ADPase enhanced apyrase polypeptide is initially synthesized as a fusion polypeptide comprising: (a) a signal peptide that promotes extracellular secretion of the soluble ADPase enhanced apyrase from the cell, the signal peptide being cleaved upon secretion, (b) one or more amino acids added to the N-terminus of the soluble ADPase enhanced apyrase polypeptide in order to improve expression levels and/or stability, and (c) a fragment of ADPase enhanced apyrase that possesses biological activity. It should also be noted that different expression hosts can process signal peptides differently, thus resulting in alterations and variations of the N-terminal or C-terminal domains. Therefore the present invention also includes variations in the sequence of the N-terminal and C-terminal domains.

It is further envisioned in the present invention that an ideal anti-platelet agent comprising natural or engineered biologically active ADPase enhanced apyrase be capable of hydrolyzing ADP at thrombus while sparing ADP at other natural clot sites. Another particularly useful class of fusion polypeptides includes those that allow localization or concentration of ADPase enhanced apyrase at a site of platelet activation and recruitment. Example of fusion polypeptides useful in the present invention for targeting the thrombus include but are not limited to; kringle 1 domain of tissue-type plasminogen activator (Runge, M. S., et al., *Circulation* (1989) 79:217-224; Haber, E., et al., *Science* (1989) 243:51-56); fusion of thrombus specific antibody; or addition of protein domain interacting with receptors specific to thrombus; such fusion polypeptides comprise a moiety that specifically binds activated platelets and ADPase enhanced apyrase, and can be prepared using recombinant DNA technology, or by using standard techniques for conjugation of polypeptides. For example, recombinant ADPase enhanced apyrase may also be chemically modified by adding, for example, ligands that specifically bind the thrombus.

Clot-specific apyrases can be designed to maximize the hydrolysis of ADP in the thrombus microenvironment while reducing the systemic reduction of ADP in circulating plasma. Specifically, ADPase enhanced apyrases can be targeted to clots by acquiring, for example, kringle domains that have specific fibrin-binding activity. Kringles are modular units found in a number of proteins that participate in the blood coagulation and fibrinolytic pathways. These structural motifs contain approximately 80 amino acids with three intramolecular disulfide bonds. The numbers of kringles domains also vary in these proteins. For example, a single kringle domain is found in urokinase-type plasminogen activator; two kringle domains are present in tissue-type plasminogen activator and prothrombin; four kringle domains are contained in hepacyte growth factor-like protein; five kringle domains are included in plasminogen; and as many as 41 kringle domains exist in apolipoprotein (Nilsen, S. L., et al., *J Biol Chem* (1999) 274:22380-22386). Hence, the fibrin binding ability of ADPase enhanced apyrases may be conferred by acquiring the from about one kringle domains to about 40 kringle domains. Clot-specific apyrase may deliver therapeutic benefits in a timelier manner. Furthermore, the concentration of ADPase enhanced apyrase activity at the clot site may also effectively lower the therapeutic dosage thus further reducing any potential side effects.

As another example, modification can be made by one skilled in the art that will alter the protein properties. For example, the primary amino acid sequence of ADPase enhanced apyrase and biologically active derivatives can be modified to, for example, remove or introduce glycosylation sites, remove or add regulatory properties to the enzyme, change the substrate specificity, change the catalytic activity, increase or decrease the pI of the enzyme, improve or reduce the enzyme stability or half-life (both shelf life and biologically active half-life), reduce the immunogenicity of the protein, alter the charge distribution of the protein, and remove or introduce requirements for cations (such as $Ca^{2+}$) or metal ions. For example, stability of the enzymes can be improved by introducing di-sulfide bonds, pH optimum can be maximized for the enzymes target environment (for example physiological pH of human blood pH 7.4), still further the Km for calcium requirement of apyrase enzymes can also be optimized for the enzymes target environment.

For example, the present invention further includes soluble ADPase enhanced apyrase polypeptides with or without associated native-pattern glycosylation. ADPase enhanced apyrase expressed in yeast or mammalian expression systems (e.g., HEK293, CHO, COS-7 cells) may be similar to or significantly different from a native ADPase enhanced apyrase polypeptide in molecular weight and glycosylation pattern, depending upon the choice of expression system. Expression of ADPase enhanced apyrase polypeptides in bacterial expression systems, such as *E. coli*, provides non-glycosylated molecules.

All peptide modification to ADPase enhanced apyrase and biologically active derivatives can be combined with appropriate expression systems to generate optimal production and bioactivity of the ADPase enhanced apyrase polypeptide and its biologically active derivatives. Determination of kinetic parameters including ratio of ATPase/ADPase activity of soluble forms of ADPase enhanced apyrase or derivatives may be obtained. Additionally, antibodies specific to ADPase enhanced apyrase or derivatives may also be generated by one skilled in the art.

ADPase Enhanced Apyrase Nucleic Acids

The present invention relates the full length ADPase enhanced apyrase molecule as well as isolated fragments, oligonucleotides, and truncations maintaining biological activity, for example N-terminal deletions, C-terminal deletions, or deletions at both N and C-termini derived from, for example ADPase enhanced apyrases listed in Table 3 (Example 6). For example, a soluble form of CD39L3 comprising N-terminal and C-terminal deletions is represented in SEQ. ID. NO: 59 and the deduced amino acid sequences SEQ. ID. NO: 60. The present invention also related to allelic variants of ADPase enhanced apyrases as well as synthetic or mutated genes of ADPase enhanced apyrases that have been modified to change, for example, the expression or activity of the recombinant protein. It is also noted that degeneracy of the nucleic acid code can be considered variations in the nucleotide sequences that encode the same amino acid residues. Therefore, the embodiment of the present invention includes nucleic acid residues that are able to hybridize under moderately stringent conditions. One skilled in the art can determine effective combinations of salt and temperature to constitute a moderately stringent hybridization condition. The present invention also relates to recombinant vectors containing a nucleotide sequence encoding ADPase enhanced apyrase or fragments thereof. Recombinant vectors include but are not limited to vectors useful for the expression of the open reading frames (ORFs) in *E. coli*, yeast, viral, baculovirus, plants or plant cells, as well as mammalian cells. Suitable expression vectors for expression in a suitable host are known to one skilled in the art and appropriate expression vectors can be obtained from commercial sources or from ATCC. The recombinant vectors useful in the present invention include ORFs comprising ADPase enhanced apyrase or biological active derivatives inserted into vectors useful for the production of protein corresponding to ADPase enhanced apyrase. Useful embodiments include, for example, promoter sequences operably linked to the ORF, regulatory sequences, and transcription termination signals.

In addition, the present invention also comprises nucleic acid sequences that have been appropriately modified, for example, by site directed mutagenesis, to remove sequences responsible for N-glycosylation not needed for biological activity. N-glycosylation sites in eukaryotic peptides are characterized by the amino acid sequence Asn-X-Ser/Thr where X is any amino acid except Pro. Modification of glycosylation sites can improve expression in for example yeast or mammalian cell cultures.

The present invention also related to nucleic acid that have been modified to improve the production and solubility of recombinant protein in a suitable host which includes, but is not limited to removing cysteine residues unnecessary for intramolecular disulfide bond formation. Cysteine residues may be changed by mutagenesis to another amino acid, for example serine, or removed from the sequence without affecting the biological activity or tertiary structure of the recombinant polypeptide.

Other modifications of the nucleic acids may be necessary to improve the stability and accumulation of the recombinant production of protein include but are not limited to mutations altering protease cleavage sites recognized by a suitable expression host. Such modifications can be made that will not adversely affect the biological activity or tertiary structure of the recombinant protein.

Additional modifications can be made to the nucleic acids that result in alterations in enzyme activity, substrate specificity, and/or biological activity. Such modifications may be preconceived based on specific knowledge relating to the protein or may be introduced by a random mutagenesis approach, for example error prone PCR. Additionally, it is also envisioned that one skilled in the art could generate chimeric nucleotide sequence comprising specific domains that can functionally replace stretches of nucleotide sequences that may add new function or improve the specificity or activity of the produced recombinant protein. For example, the nucleotide sequence comprising the catalytic region of ADPase enhanced apyrase may be functionally replaced with a nucleotide sequence from an ortholog or homolog of ADPase enhanced apyrase thereby conferring improved or novel function. Modification resulting in changed biological activity of ADPase enhanced apyrases may be necessary to improve the therapeutic effectiveness of the protein or to minimize potential side effects. Modification of the nucleic acid sequences can also be made that alter potential immunogenic sites that may result in allergic reactions to patients' administered with recombinant ADPase enhanced apyrase protein.

Silent modifications can be made to the nucleic acids that do not alter, substitute or delete the respective amino acid in the recombinant protein. Such modification may be necessary to optimize, for example, the codon usage for a specific recombinant host. The nucleotide sequence of ADPase enhanced apyrase can be modified to replace codons that are considered rare or have a low frequency of appropriate t-RNA molecules to a more suitable codon appropriate for the expression host. Such codon tables are known to exist and are readily available to one skilled in the art. In addition, silent modification can be made to the nucleic acid that minimizes secondary structure loops at the level of mRNA that may be deleterious to recombinant protein expression.

Expression Systems Useful for Production of ADPase Enhanced Apyrases

The present invention also provides for recombinant cloning and expression vectors useful for the production of biologically active ADPase enhanced apyrases. Such expression plasmids may be used to prepare recombinant ADPase enhanced apyrases polypeptides encoded by the nucleic acids in a suitable host organism. Suitable host organisms for the production of ADPase enhanced apyrase and functional derivatives include but are not limited to bacteria, yeast, insect cells, mammalian cells, plants and plant cells. In addition, cell free systems may also be employed for the production of recombinant proteins. One skilled in the art can readily prepare plasmids suitable for the expression of recombinant ADPase enhanced apyrases in the suitable host organism. Appropriate cloning and expression vectors are readily available to one skilled in the art and can be obtained from commercial sources or from the ATCC.

The recombinant protein can be produced in the within the host cell or secreted into the culture medium depending on the nature of the vector system used for the production of the recombinant protein. Generally plasmids useful for the expression of the recombinant ADPase enhanced apyrases comprise necessary operable linked regulatory elements such as a promoter sequence (including operators, enhancers, silencers, ribosomal binding sites), transcriptional enhancing sequences, translational fusions to signal peptides (native or heterologous) or peptide sequences useful for the purification of recombinant protein (for example His Tag, FLAG, MBP, GST), transcription termination signals and poly adenylation signals (if necessary).

It may also be necessary for the recombinant plasmid to replicate in the host cell. This requires the use of an origin of replication suitable for the host organism. Alternatively, the recombinant expression plasmid may be stably integrated into the host's chromosome. This may require homologous recombination or random integration into the host chromosomes. Both instances require the use of an appropriate selection mechanism to distinguish transformed host cells from non-transformed host cells. Useful selection schemes include the use of, for example, antibiotics (for example, G418, Zeocin®, kanamycin, tetracycline, gentamicin, spectinomycin, ampicillin), complementation of an auxotroph (for example Trp-, DHFR-), and scorable markers (for example β-glucoronidase, β-galactosidase, Green Fluorescent Protein).

Expression systems useful in the present invention include yeast systems particularly suitable for expression of human secretory proteins. For example the yeast expression system based on *Kluyveromyces lactis* has been particularly successful for the recombinant production of human secretory proteins (Fleer, R., et al., *Gene* (1991) 107:285-295; Fleer, R., et al., *Biotechnology* (1991) 9:968-997). Plasmid vectors particularly useful for the transformation and expression of protein in recombinant *K lactis* have been descried (Chen, X-J., *Gene* (1996) 172:131-136). Other yeast expression systems based on *Saccharomyces cerevisiae* or *Pichia pastoris* or *Pichia methanolica* may also be useful for the recombinant production of ADPase enhanced apyrase. For example, *P. pastoris* modified for the production of human glycoprotein (Hamilton, S. R., et al., *Science* (2003) 301:1244-1246). Expression plasmids suitable for the expression of ADPase enhanced apyrases in *S. cerevisiae, P. pastoris,* or *P. methanolica* may be obtained from a commercial source or ATCC. Plasmids described above may also be modified by one skilled in the art to optimize, for example, promoter sequences and or secretion signals optimal for the host organism and recombinant production of ADPase enhanced apyrases. Established methods are also available to one skilled in the art for introducing recombinant plasmid into the yeast strains.

Expression of recombinant ADPase enhanced apyrases in mammalian cell culture is also a preferred embodiment of the present invention. There are a wide variety of mammalian cell lines available to one skilled in the art. The most widely used and most successful mammalian expression system is based on a dhfr- (dihydrofolate reductase) Chinese hamster ovary (CHO) cell line along with a suitable expression plasmid containing the dhfr gene and suitable promoter sequence. The cells may be transfected for transient expression or stable expression of the protein of interest. Other factors for the production of foreign protein in mammalian cells including regulatory considerations have been reviewed (Bendig, M., *Genetic Engineering* (1988) 7:91-127). A particularly useful mammalian expression system for production recombinant ADPase enhanced apyrase is based on the EF-1α promoter (Mizushima, S., and Nagata, *Nucleic Acids Res* (1990) 18:5322) and Human embryonic kidney (HEK) 293T cell line (Chen, P., et al., *Protein Expression and Purification* (2002) 24:481-488). Variants of the commercially available CHO and 293T cells lines and their suitable growth and expression media may be used to further improve protein production yields. Variants of commercially available expression vectors including different promoters, secretion signals, transcription enhancers, etc., may also be used to improve protein production yields.

Another expression system useful in the present invention includes expression in *E. coli*. *E. coli* expression of therapeutic proteins can represent significant commercial advantages based on manufacturing costs versus production in mammalian cells. There are several expression systems known to one skilled in the art for production of recombinant proteins in *E. coli*. Expression of mammalian protein in *E. coli* may not be particularly useful due to the fact that many mammalian proteins are post translationally modified by glycosylation or may contain intra or inter di-sulfide molecular bonds. However there are certain apyrase members (for example CD39L4, human Scan-1) that do not require post-translational glycosylation for enzymatic activity. Such apyrase enzymes are particularly suitable for expression in *E. coli*. Other advantages of *E. coli* expression may result from the expressed protein being deposited into inclusion bodies. Inclusion bodies would simplify the protein purification process if a suitable protein refolding method is developed to recover active enzyme from the inclusion body. Particular *E. coli* expression plasmid useful in the present invention may include, for example, fusions with signal peptides to target the protein to the periplasmic space. Additionally, *E. coli* host strains that contain mutations in both the thioredoxin reductase (trxB) and glutathione reductase (gor) genes greatly enhance disulfide bond formation in the cytoplasm (Prinz, W. A., et al., *J. Biol. Chem.* (1997) 272:15661-15667). The addition of thioredoxin fused to the N-terminus or C-terminus of ADPase enhanced apyrase may also aid in the production of soluble protein in *E. coli* cells. (LaVallie, E. R., et al., *Bio/Technology* (1993) 11:187-193).

Other expression systems known in the art may also be employed for the production of active ADPase enhanced apyrase and include but are not limited to baculovirus expression (Luckow, V., *Curr Opin Biotechnol* (1993) 5:564-572) or the production of recombinant ADPase enhanced apyrases in a plant leaf or seeds, for example corn seeds.

Purification of biologically active ADPase enhanced apyrases may be purified from the recombinant expression system using techniques known to one normally skilled in the art. Expression of the ADPase enhanced apyrases protein can either be intracellular, inclusion bodies, or secreted in the media fraction. Secretion of ADPase enhanced apyrases into the media (for example, protein free or chemically defined) simplifies protein purification and is the preferred embodiment in the present invention. Expression of intracellular ADPase enhanced apyrases requires disruption of the cell pellets by any convenient method including freeze-thaw, mechanical disruption, sonication, or use of detergents or cell lysing enzymes or agents. Following disruption or concentration of secreted protein, purification of ADPase enhanced apyrases can be accomplished by a number of methods known to one skilled in the art. For example, commercially available affinity chromatography may be used to purify recombinant ADPase enhanced apyrases fusions with affinity tags such as: 6XHIS, FLAG, GST, or MBP. In addition, antibodies specific to ADPase enhanced apyrases may be used for affinity purification. In addition, matrices chemically modified with a ligand having strong affinity to ADPase enhanced apyrases as a substrate mimic may also be used for affinity purification. ADPase enhanced apyrases may also be purified with the use of an affinity tag or antibodies following conventional protein purification methods know to one skilled in the art.

The desired degree of purity of ADPase enhanced apyrases must also be taken into consideration. For application involving administration of ADPase enhanced apyrases in vivo, highly purified ADPase enhanced apyrases are desirable. Most preferable purification of ADPase enhanced apyrases should result in no detectable band corresponding to other (non-ADPase enhanced apyrases) polypeptides on a silver stained SDS-Page gel. It should also be noted that depending on the recombinant expression system used other bands corresponding to ADPase enhanced apyrases may be visible. This may be due to alterations in protein glycosylation, internal ribosome initiation, post-translation modification and the like.

Methods for In Vitro and In Vivo Validation of ADPase Enhanced Apyrase Efficacy

Biochemical function of ADPase enhanced apyrases or derivatives may be assessed by numerous methods available to one skilled in the art. For example, ATPase and ADPase enzyme activities of purified soluble ADPase enhanced apyrases can be determined at 37° C. in a 1 ml solution containing 8 mM $CaCl_2$, 200 µM substrate (ATP for ATPase or ADP for ADPase), 50 mM imidazole, and 50 mM Tris, pH 7.5 (Picher, et al., *Biochem. Pharmacol.* (1988) 51:1453). The reaction can be stopped and inorganic phosphate released can be measured by addition of 0.25 ml of malachite green reagent (Baykov, et al., *Anal. Biochem.* (1988) 171:266). Based on the spectrophotometric analysis at 630 nm, one unit of ATPase (or ADPase) corresponds to release of 1µ mole of inorganic phosphate/min at 37° C. Key kinetic constants for the enzyme such as $K_m$ and $k_{cat}$ may be obtained by fitting data into, for example, a Michaelis-Menten equation. Other assays useful for monitoring biochemical function include, but are not limited to, a radiometric assay, a HPLC assay both described by Gayle III, et al. (*J. Clin Invest.* (1998) 101:1851-1859) or a radio-TLC assay described by Marcus, A. J., et al. (*J. Clin Invest.* (1991) 88:1690-1696).

Biological function of ADPase enhanced apyrases or derivatives may be assessed by ex vivo methods as well as in vivo methods. Ex vivo methods useful for monitoring the biological function of ADPase enhanced apyrases and derivatives include, for example, platelet aggregation assays (Pinsky, D. J., et al., *J. Clin Invest.* (2002) 109:1031-1040; Ozaki, Y, *Sysmex J. Int* (1998) 8:15-22).

In vivo methods useful for assessing the biological functions of ADPase enhanced apyrases and derivatives include, but are not limited to, murine stroke model measuring bleeding time, infarction volume, blood flow, neurological deficit, intracerebral hemorrhage, and mortality (Pinsky, D. J., et al., supra; Choudhri, T. F., et al., *J. Exp. Med.* (1999) 90:91-99), murine lung ischemia/reperfusion model (Fujita, T., et al., *Nature Med.* (2001) 7:598-604), baboon model of reperfused stroke (Huang, J., et al., *Stroke* (2000) 31:3054-3063), $cd39^{-/-}$ mice (Pinsky, D. J., et al., *J. Clin Invest.* (2002) 109: 1031-1040) and Yorkshire-Hampshire Pig model (Maliszewski, C. R., et al., PCT WO 00/23094 (2000)) and rabbit model (Herbertm, J-M., et. al., *Thromb Haemost* (1998) 80:512-518; Fishman, J. et. al., *Lab Invest* (1975) 32:339-351; Sarembock, et. al., *Circulation* (1989) 80: 1029-1040) of PCI. Other methods may be known to one skilled in the art for assessing the biological function of ADPase enhanced apyrases and derivatives as a thromboregulator.

Therapeutic Compositions of ADPase Enhanced Apyrases

The present invention provides compositions comprising a biologically effective amount of ADPase enhanced apyrase polypeptide or biologically active derivative in a pharmaceutically acceptable dosage. Therapeutic composition of ADPase enhanced apyrases or biologically active derivative may be administered clinically to a patient before symptoms, during symptoms, or after symptoms. After symptom administration of ADPase enhanced apyrases or biologically active derivates may occur, for example, between 0 and 48 hours after the onset of stroke. Administration of ADPase enhanced apyrases or biologically active derivatives to achieve therapeutic effect may be given by, for example, bolus injection, continuous infusion, sustained release, or other pharmaceutically acceptable techniques. Certain clinical situations may require administration of ADPase enhanced apyrases or biologically active derivatives as a single effective dose, or may be administered daily for up to a week or a much as a month or more. Ideally ADPase enhanced apyrases will be administered to patients in a pharmaceutically acceptable form containing physiologically acceptable carriers, excipients or diluents. Such diluents and excipients may be comprised of neutral buffered saline solution, antioxidants (for example ascorbic acid), low molecular weight polypeptides (for example polypeptides$\leqq$10 amino acids) amino acids, carbohydrates (for example, glucose, dextrose, sucrose, or dextrans), chelating agents such as EDTA, stabilizers (such as glutathione). Additionally, cosubstrates for the ADPase enhanced apyrases or biologically active derivatives, for example, calcium ($Ca^{2+}$) may be administered at time of dosage for maximal activity of the enzyme. Such carriers and diluents will be nontoxic to the patient at recommended dosages and concentrations. It is also envisioned in the present invention that ADPase enhanced apyrases or biologically active derivatives may be administer with other agents that synergistically enhance the benefit of ADPase enhanced apyrases or biologically active derivatives alone. For example, it is envisioned that administration of other antiplatelets or anticoagulants, such as aspirin, heparin or bivalirudin with ADPase enhanced apyrases or biologically active derivative may have additional benefits such as improve reperfusion, extend therapeutic time window, prevent reocclusion, and prevent microvascular thrombosis. It is also envisioned that administration of ADPase enhanced apyrases or biologically active derivatives may improve efficacy and lower the effective dosage of thrombolytics (Activase®, TNKase™, vampire bat plasminogen activator, urokinase, streptokinase, staphylokinase, and ancrod). It is still further envisioned in the present invention that operable fusion polypeptides between, for example, and ADP enhanced apyrase and thrombolytic (for example, TNKase) may provide an ideal therapeutic solution for acute myocardial infarction (AMI), percutaneous coronary intervention (PCI) and acute ischemic stroke (AIS).

Thrombosis also has a proinflammatory component whereby biologically functional substances are synthesized by interactions between platelets and neutrophils (*In: Inflammation*: Basic principles and clinical correlates, 3rd ed., Gallin, J. I., and Snyderman, R. (1999) pp. 77-95). Activation of platelets releases ADP as well as ATP. It has been demonstrated that extracellular ATP induces secretion of pro-inflammatory interferon-γ and IL-2 (Langston, H., et al., *J. Immunol.* (2003) 170:2962-2970). Recent studies show that CD39 on Langerhans cells modulates inflammation and immunity in the skin (Granstein, R., *Nature Medicine* (2002). 8:336-338). Therefore the ATPase activity of ADPase enhanced apyrases and biologically active derivatives may indirectly lower inflammatory and/or immune responses at sites of vascular injury and provide a clinical benefit to patients receiving such treatment.

In adrenergic nerves, ATP and norepinephrine are stored together in vesicles, and both are released in parallel during neurotransmission. Excessive norepinephrine release is a major cause of ischemic cardiac dysfunction and reperfusion arrhythmias which can precipitate sudden cardiac death (Levi, R., and Smith, N., *J. Pharmacol Exp. Ther.* (2000) 292:825-830). Hydrolysis of ATP released by sympathetic nerve endings lead to inhibition of norepinephrine release (Sesti, C., et al., *J. Pharmacol. Exp. Ther.* (2002) 300:605-611). Hence, ATPase activity of ADPase enhanced apyrases may provide cardioprotective effect and prevent fatal arrhythmia for patients receiving such treatment.

Certain clinical situations may require the slow and prolonged release of biologically active ADPase enhanced apyrases or biological derivatives. Such situations may require the sequestrations of ADPase enhanced apyrases or biological derivatives in, for example, hydrogel or other pharmaceutically acceptable polymerizable gels. Additionally, a polyethylene glycol (PEG) can be added to prolong the blood half-life to increase efficacy of a soluble ADPase enhanced apyrases. In the case where ADPase enhanced apyrases is used as a preventative medication, this may allow for single-bolus dose administration to maintain protective effects of ADPase enhanced apyrases for longer periods. Other protein modifications to alter protein half-life include, for example, albumin conjugation, IgG fusion molecules and altering of the proteins glycosylation pattern.

It is also envisioned in the present invention that certain medical procedures or instances may require inhibition of circulating ADPase enhanced apyrase activity. Such inhibitors could be, for example, pharmaceutically acceptable enzyme inhibitors (for example, ADP analogues), pharmaceutically acceptable calcium chelators, antibodies specific to ADPase enhanced apyrase. Other medical procedures could also include, for example, blood transfusions or platelet transfusions.

ADPase enhanced apyrases and biologically active derivatives are useful in any clinical situation where the hydrolysis of ATP and/or ADP to AMP is clinically beneficent including disease states where ATP and/or ADP concentrations are abnormally high. ADPase enhanced apyrases and biologically active derivatives are beneficial in clinical situations where platelets or activated platelets play an important role in disease progression, for example, tumor metastases (Bakewell, S. J., et al., *PNAS* (2003) 100:14205-14210).

Dosage requirements of ADPase enhanced apyrases or biologically active derivatives may vary significantly depending on age, race, weight, height, gender, duration of treatment, methods of administration, biological activity of ADPase enhanced apyrases, and severity of condition or other clinical variables. Effective dosages may be determined by a skilled physician or other skilled medical personnel.

The clinical and biological effectiveness of the administered ADPase enhanced apyrases or biological derivative can be readily evaluated at given time intervals after administration. For example, administration of ADPase enhanced apyrases or biological derivatives should promote longer bleeding times in the setting where platelet count remains unchanged. Additionally, direct measurement of blood samples for enzyme activity of ADPase enhanced apyrases or biological derivative will also indicate presence of the molecule in the circulating blood. Based on precise sampling of blood samples coupled with methods known in the art for assessing biochemical function of ADPase enhanced apyrases the half life of the protein can be estimated. Additional clinically relevant assays for the presence of biologically active ADPase enhanced apyrases or biologically active derivative may also be envisioned.

The following examples are intended to illustrate but not to limit the invention. Unless otherwise defined, all technical and scientific terms used herein have meanings commonly known to one ordinarily skilled in the art. Although methods and materials similar or equivalent to those described herein can be used in the practice or testing of the invention, suitable methods are described below and are intended to illustrate but not to limit the invention. All publications, patent applications, patents, and other references mentioned herein are incorporated by reference in their entirety. Other features and advantages of the invention will also be apparent from following the detailed description and claims of the invention.

In the following examples, various modified forms of enzymes that catalyze hydrolysis of various nucleotides are prepared. For convenience, these modified forms are listed below:

| Protein | Native | Modification |
|---------|--------|--------------|
| 8429 | Sol CD39 | — |
| 8848 | Sol CD39 | H66G |
| 8864 | Sol CD39 | H66A |
| 8812 | Sol CD39 | H66G, S68R |
| 8828 | Sol CD39 | H66A, S68R |
| 8272 | Sol CD39L3 | — |
| 8555 | Sol CD39L3 | R67A |
| 8519 | Sol CD39L3 | R67G |
| 8906 | Sol CD39L3 | R67A, T69R |
| 8742 | Sol CD39L3 | R67G, T69R |
| 9170 | CD39 | +linker + kringle |
| 9173 | CD39 | +linker + kringle + R67A, T69R |
| 9150 | CD39L3 | +linker + kringle |
| 9124 | CD39L3 | +linker + kringle + R67G, T69R |
| 9198 | Sol SCAN-1 | — |
| 9267 | Sol SCAN-1 | L199S |
| 9275 | Sol SCAN-1 | I252W |
| 9279 | Sol SCAN-1 | E279S, D282F |
| 9285 | Sol SCAN-1 | E334V, G338D |

EXAMPLE 1

Cloning of CD39

CD39 has been previously identified and cloned (Maliszerski, C. R., et. al., *J. Immunol.* (1994) 153:3574). Cloning of CD39 can be accomplished by numerous methods available to one skilled in the art. For example, total RNA or poly-A RNA can be purified from human tissues samples abundant in CD39 expression (for example placenta or spleen tissue) and used as a template for gene specific RT-PCR. Additionally, pre-made cDNA libraries can be purchased from commercial sources and PCR can be employed to amplify the CD39 cDNA directly. Still further, synthetic oligos can be constructed to create a synthetic gene for CD39 based on sequence information available for CD39 (Genbank accession # np_001767). Additionally, full length cDNA clones can be obtained from, for example, the IMAGE clone consortium (which can be found on the web at: image.llnl.gov/).

The full length cDNA clone for CD39 was isolated by PCR from human placenta large insert cDNA library Lot 2060677 (Clontech, Palo Alto, Calif.) using the oligonucleotide primer CD39 5' B (FL) (SEQ. ID. NO: 1) and CD39 3' (FL) (SEQ. ID. NO: 2). CD39 was cloned by combining 5 µl of library extract, 1 µl of CD39 5' B (FL) primer (100 ng), 1 µl of CD39 3' (FL) primer (100 ng) and 50 µl PCR Supermix High Fidelity (Invitrogen, Carlsbad, Calif.). Thirty (30) cycles of PCR under the following conditions 94C-30sec, 55C-30sec, 72C-1 min were performed.

Following PCR amplification the PCR product was directly subcloned in pGEM T-easy (Promega Madison, Wis.) and designated pAPT7948. The authenticity of the sequence of the cloned CD39 was confirmed (the second amino acid residue was changed from lysine to glutamine by introduction of the NcoI restriction enzyme site) to be identical to the sequence published in GenBank. (accession # np_001767) (Matsumoto, M., et al., *FEBS Lett.* (1999) 453: 335-340) by DNA sequence analysis using sequencing primers 39-1 through 39-10 (SEQ. ID. NOs: 3-12). The full length nucleotide sequence of CD39 is designated SEQ. ID. NO: 53 and the deduced amino acid sequence is designated SEQ. ID. NO: 54.

EXAMPLE 2

Cloning of CD39L3

CD39L3 has been determined to be an isozyme of CD39 that is preferably expressed in human brain tissue. Chadwick and Frischauf (*Genomics* (1998) 50:357-367) have studied the tissue distribution of several CD39 family members including CD39L3. Based on their observations it is clear that CD39L3 is predominately expressed in Human brain and pancreas tissues and represent preferred source material for cloning CD39L3. Other tissue sources useful for cloning CD39L3 include but are not limited to placenta, spleen, prostate, ovary, small intestine and colon.

Cloning of CD39L3 can be accomplished by numerous methods available to one skilled in the art. For example, total RNA or poly-A RNA can be purified from source tissues mentioned supra and used as a template for gene specific RT-PCR. Additionally, pre-made cDNA libraries can be purchased from commercial sources and PCR can be employed to amplify the CD39L3 cDNA directly. Still further, synthetic oligos can be constructed to create a synthetic gene for CD39L3 based on sequence information available for CD39L3 (Genbank accession # np_001239). Additionally, full length cDNA clones can be obtained from, for example, the IMAGE clone consortium.

CD39L3 was cloned from the Large-Insert Human Brain cDNA Library (Clontech Palo Alto, Calif. Cat # HL5500u, Lot #1070483) by PCR using gene specific primers. An NcoI site was introduced at the translations start site for CD39L3 for convenient cloning into expression plasmids. CD39L3 was cloned by combining 5 µl of library extract, 1 µl of 5' primer (100 ng), 1 µl of 3' primer (100 ng) and 50 µl PCR Supermix High Fidelity (Invitrogen, Carlsbad, Calif.). Thirty (30) cycles of PCR under the following conditions 94C-30sec, 55C-30sec, 72C-1 min were performed.

The full length CD39L3 clone was obtained in three separate PCR reactions. The 5' portion of the gene was amplified with the primer CD39L3 5' FL (SEQ. ID. NO: 25) and primer L3-8 (SEQ. ID. NO: 36). The middle portion of the gene was amplified with primer L3-3 (SEQ. ID. NO: 31) and CD39L3 3' (SEQ. ID. NO: 28) and the 3' end of the gene was amplified with primer L3-5 (SEQ. ID. NO: 33) and CD39L3 3' FL (SEQ. ID. NO: 27). Amplified products were cloned into pGEM-T Easy (Promega, Madison, Wis.) and sequenced resulting in pAPT7894, pAPT7863, and pAPT7903 respectively. The full length cDNA was constructed using convenient restrictions sites located within the CD39L3 coding region and pGEM-T Easy resulting in the production of plasmid pAPT7949. The primers used for sequencing the CD39L3 gene are designated L3-1 through L3-10 (SEQ. ID. NOs: 29-38). The sequence of the cloned full length CD39L3 is shown as SEQ. ID. NO: 55 and the deduced amino acid sequence is shown as SEQ. ID. NO: 56. Based on the sequence results obtained, amino acid 496 was changed from valine to alanine based on the sequence deposited in Genbank (accession # np_001239). Site directed mutagenesis may be used to change the amino acid back to valine.

EXAMPLE 3

Design and Cloning of a Soluble Form of CD39

The soluble form of CD39 (solCD39), generated by removing the N-terminal 37 amino acids and C-terminal 33 amino acids, has been previously described. (Gayle, R. B., et al., *J. Clin. Invest.* (1998) 101:1851-1859). pAPT7948 was used as atemplate for PCR to generate solCD39 using the PCR primers CD39 Sma 5' (SEQ. ID. NO: 13) and CD39 Sma 3' (SEQ. ID. NO: 14). In order to facilitate cloning of solCD39 into vectors suitable for expression in mammalian cells (for example, CHO, COS, HEK293), a SmaI site was introduced in frame with the ATG translation initiation codon.

The PCR product was digested with SmaI and subcloned directly into pSP72 (Promega Madison, Wis.) resulting in plasmid pAPT 7987. The sequence of the soluble form of CD39 was re-confirmed. N-terminal translational fusions of solCD39 with, for example, secretion signals can be easily obtained by removing the solCD39 open reading frame by SmaI restriction enzyme digestion. The nucleotide sequence of the solCD39 is designated SEQ. ID. NO: 57 and the deduced amino acid sequence designated SEQ. ID. NO: 58. The plasmid pAPT7987 comprising solCD39 was also utilized for subsequent site directed mutagenesis studies described in Example 6.

EXAMPLE 4

Design and Cloning of a Soluble Form of CD39L3

The protein sequence of CD39L3 was analyzed by Swiss-Prot (Bairoch, A., and Apweiler, R., *Nucleic Acids Res* (2000) 28:45-48). The analysis indicated that CD39L3 has a transmembrane domain at both the N- and C-termini; also seven potential N-glycosylation sites were identified. Based on the analysis, a soluble form of CD39L3 was designed by removing the N-terminal 44 amino acids and the C-terminal 43 amino acids.

In order to facilitate cloning of CD39L3 into vectors suitable for expression in mammalian cells (for example, CHO, COS, HEK293), the soluble form of CD39L3 was modified by PCR to introduce a SmaI restriction site in frame with the ATG of soluble CD39L3 using PCR primers L3-Sma5' (SEQ. ID. NO: 39) and L3-Sma3' (SEQ. ID. NO: 40). The resulting PCR product was cloned into the SmaI site of pSP72 (Promega, Madison, Wis.) and the sequence was reconfirmed resulting in plasmid pAPT7983. The nucleotide sequence of the sol-CD39L3 is designated SEQ. ID. NO: 59 and the deduced amino acid sequence designated SEQ. ID. NO: 60.

EXAMPLE 5

Identification of Key Amino Acid Residues for Nucleotide Specificity of Human CD39 Apyrase Family Structure based sequence comparison between the ACR's of the human CD39 apyrase family members indicates that Lysine 18 of actin is replaced by arginine in NDPase members (for example NTPDase4, NTPDase5, NTPDase6) that would enhance interaction with the α- and β-phosphates (FIG. 3, Table 1). In contrast, Leucine 16 of actin is replaced by a glycine or serine at the analogous position in the members having high NDPase activity. A histidine or arginine was found in ACR1 of CD39, NTPase2 and CD39L3 which are active with ATP substitutes. This positively charged residue may interact with both β- and γ-phosphates. Based on the understanding of key residues involved in enzyme catalysis and substrate specificity determination, several site directed mutations were introduced to CD39 and CD39L3 (Table 2).

TABLE 2

Site directed mutants of ACR1 in CD39 and CD39L3

| | | |
|---|---|---|
| CD39 | ... IVLDAGSSHTSLYIY | (SEQ ID NO:161) ... |
| CD39 H66G | ... IVLDAGSSGTSLYIY | (SEQ ID NO:162) ... |
| CD39 H66A | ... IVLDAGSSATSLYIY | (SEQ ID NO:163) ... |
| CD39 H66G S68R | ... IVLDAGSSGTRLYIY | (SEQ ID NO:164) ... |
| CD39 H66A S68R | ... IVLDAGSSATRLYIY | (SEQ ID NO:165) ... |
| CD39L3 | ... IVLDAGSSRTTVYVY | (SEQ ID NO:166) ... |
| CD39L3 R67G | ... IVLDAGSSGTTVYVY | (SEQ ID NO:167) ... |
| CD39L3 R67A | ... IVLDAGSSATTVYVY | (SEQ ID NO:168) ... |
| CD39L3 R67G T69R | ... IVLDAGSSGTRVYVY | (SEQ ID NO:169) ... |
| CD39L3 R67A T69R | ... IVLDAGSSATRVYVY | (SEQ ID NO:170) ... |

EXAMPLE 6

Site Directed Mutagenesis of solCD39 and solCD39L3

Site directed mutagenesis was performed on solCD39 and solCD39L3 using the templates pAPT7987 and pAPT7987 respectively. Point mutations described in Example 5 (Table 2) were introduced using the quick change site directed mutagenesis kit (Stratagene, La Jolla, Calif.) according to manufactures instructions. Four independent mutations were generated for both solCD39 and solCD39L3 (Table 2). Mutagenesis primers used to introduce the respective point mutations in solCD39 and solCD39L3 are identified in Table 3. Following site directed mutagenesis the sequence of the entire open reading frame of all the mutants generated were verified by DNA sequence analysis. The resulting clones generated by site directed mutagenesis along with their corresponding mammalian expression plasmid identification are listed in Table 3.

TABLE 3

Coding sequence and expression plasmids of wild type and mutant forms of solCD39 and solCD39L3.

| Gene | Plasmid | Base Plasmid Type | SEQ. ID. NO: Mutagenesis Primers | SEQ. ID. NO: Nucleotide | SEQ. ID. NO: Peptide | Expression Plasmid/Protein | Base Expression Plasmid |
|---|---|---|---|---|---|---|---|
| solCD39 | pAPT7987 | pSP72 | — | 57 | 58 | pAPT8429/APT8429 | pSeqTag2 SrfI |
| solCD39 H66G | pAPT8696 | pSP72 | 15, 16 | 61 | 62 | pAPT8848/APT8848 | pSeqTag2 SrfI |
| solCD39 H66A | pAPT8698 | pSP72 | 17, 18 | 63 | 64 | pAPT8864/APT8864 | pSeqTag2 SrfI |
| solCD39 H66G S68R | pAPT8701 | pSP72 | 19, 20 | 65 | 66 | pAPT8812/APT8812 | pSeqTag2 SrfI |
| solCD39 H66A S68R | pAPT8702 | pSP72 | 21, 22 | 67 | 68 | pAPT8828/APT8828 | pSeqTag2 SrfI |
| solCD39L3 | pAPT7983 | pSP72 | — | 59 | 60 | pAPT8272/APT8272 | pSeqTag2 SrfI |
| solCD39L3 R67A | pAPT8468 | pSP72 | 41, 42 | 69 | 70 | pAPT8555/APT8555 | 3X Flag CMV 8 |
| solCD39L3 R67G | pAPT8459 | pSP72 | 43, 44 | 71 | 72 | pAPT8519/APT8519 | 3X Flag CMV 8 |
| solCD39L3 R67A T69R | pAPT8461 | pSP72 | 45, 46 | 73 | 74 | pAPT8906/APT8906 | pSeqTag2 SrfI |
| solCD39L3 R67G T69R | pAPT8470 | pSP72 | 46, 47 | 75 | 76 | pAPT8742/APT8742 | pSeqTag2 SrfI |

EXAMPLE 7

Expression of Wild Type and Mutant Forms of solCD39 and solCD39L3

To test the in vitro and in vivo enzymatic properties of the various mutations in solCD39 and solCD39L3 the genes comprising the mutations were cloned into appropriate expression plasmids (Table 3, for example, 3xFLAG CMV8 (Sigma-Aldrich, St. Louis, Mo.) and pSEQTAG2a (Invitrogen Carlsbad, Calif.) suitable for the production of secreted recombinant protein in mammalian cells (for example, CHO and HEK293).

Specifically, solCD39L3 mutants R67A and R67G were translationally fused to a blunt ended Not I site of 3xFLAG CMV8 resulting in plasmids pAPT8555 and pAPT8519 respectively (Table 3). In addition to the Preprotrypsin secretion signal a 3xFLAG sequence was also translationally fused to the N-terminus of solCD39L3 R67A and solCD39L3 R67G.

To facilitate rapid cloning of the remaining open reading frames comprising wild type and mutant forms of solCD39 and solCD39L3, pSEQTAG2a (Invitrogen, Carlsbad Calif.) was modified by site directed mutagenesis (Quick Change, Stratagene, Carlsbad, Calif.) to introduce a SrfI restriction site in frame with the Igκ leader sequence (FIG. 7) using mutagenesis primers Seqtag2-srfA (SEQ. ID. NO: 51) and Seqtag2-srfB (SEQ. ID. NO: 52).

The SmaI fragment of the remaining solCD39 and solCD39L3 genes were translationally fused to the SrfI site in plasmid pSEQTAG2a SrfI. The resulting expression plasmids derived from the various cloning are listed in Table 3. Proper post translation processing of the secretory Igκ leader sequence in pSEQTAG2a SrfI will result in the fusion of four additional amino acids (D-A-P-G) to the N-terminus of the respective proteins.

EXAMPLE 8

Transient Transfection and Partial Purification of ADPase Enhanced Apyrases in HEK293T Cells Expression plasmids listed in Table 3 were transfected into 293T cell lines (GenHunter, Nashville, Tenn.) in four 100 mm dishes using transfectant FuGene 6 (Roche) according to manufacturer's recommendations. Transfected cells were grown in DMEM medium, supplemented with 1% BCS, 1% MEM non-essential amino acids, 1% penicillin-streptomycin and 2 mM L-glutamine. After 3 days growth, the conditioned medium (CM) was collected and the cell debris was removed by centrifugation. All the proteins in CM were harvested by centrifugation after 65% ammonium sulfate precipitation. The pellet was dissolved in 2.5 ml of 20 mM Tris-HCl, pH 7.4, and desalted through EconoPac 10DG desalting column (BioRad, Hercules, Calif.). Total 4 ml of desalted CM was loaded on a DEAE column and washed with 10 ml of 20 mM Tris-HCl (pH 7.4) and 10 ml of 50 mM NaCl in the Tris buffer. SolCD39 (APT8429), solCD39L3 (APT8272) and mutants thereof were eluted with 10 ml of 300 mM NaCl in the Tris buffer. For platelet aggregation study, the buffer was exchanged by 1× Tris buffered saline (Sigma, St. Louis, Mo.).

The ADPase and ATPase activities of soluble ADPase enhanced apyrases were estimated by ADP and ATP hydrolysis assays using malachite green (Baykov, et al., *Anal. Biochem.* (1988) 171:266-270). Enzymatic analysis was initiated by the addition of 5 µl of the partially purified ADPase enhanced apyrases to 495 µl of a mixture containing 50 mM Tris-HCl (pH 7.4), 8 mM $CaCl_2$, and various concentrations of ADP or ATP. Following 30 minute incubation at 37° C., 50 µl of the reaction solution was mixed with 900 µl of 50 mM Tris-HCl (pH 7.4) and 50 µl of the malachite working solution. The inorganic phosphate released from the ADP or ATP reacts with the malachite working solution, resulting in a green color. Since the enzymatic activity of apyrases is proportional to the amount of the released inorganic phosphate, apyrase activity can be measured by monitoring the absorbance at 630 nm using an Agilent 8453 UV-Visible spectrophotometer (Agilent, Palo Alto, Calif.). The kinetics of the enzymatic reaction was determined by measuring the time course of the color development at a wavelength of 630 nm. Initial rates of ADP hydrolysis by the recombinant soluble CD39 were determined and kinetic constants were derived.

EXAMPLE 9

Determination of Kinetic Parameters of ADPase Enhanced Apyrases

Following partial purification kinetic parameters were determined for the various site directed mutants of CD39 (APT8429, APT8848, APT8864, APT8812, APT8828) and CD39L3 (APT8272, APT8555, APT8519, APT8906, APT8742) (Table 4). Based on the data presented in Table 4 there was noticeable improvement in the ratio of ADPase to ATPase $((V/K)^{ATP}/(V/K)^{ADP})$ for APT8555, APT8742, APT8828, and APT8848. The mutations introduced into APT8906 resulted in a 5-fold increase in ADPase activity and a 4-fold increase in ATPase activity, while retaining a similar ratio $((V/K)^{ATP}/(V/K)^{ADP})$ to the wild type enzyme (APT8272) indication that these mutation improved the overall catalytic performance of the enzyme. The mutation represented in APT8848 had an improved $V/K)^{ATP}/(V/K)^{ADP}$ resulting from a 2 fold reduction of ATPase activity. with no change in ADPase activity. In the case of the double mutation represented in APT8742 ADPase activity was improved approximately 5 fold with a slight increase in ATPase activity. Similar to the APT8848 mutant, APT8828 displayed a slight increase in ADPase activity and slight decrease in ATPase activity resulting a ADPase enhanced apyrase compared to their wild type counterparts. Therefore to get full benefit of improved ratio of ADPase to ATPase $((V/K)^{ATP}/(V/K)^{ADP})$ the mutations represented in APT8742, APT8848, and APT8828 are preferred. Its is also envisioned in the present invention that one skilled in the art may devise alternative amino acid substitutions and combinations of substitutions that may impact the ratio of ADPase to ATPase $((V/K)^{ATP}/(V/K)^{ADP})$.

EXAMPLE 10

Cloning of Kringle Domain with Linker Sequence

Human Plasminogen binds to fibrin clots via its Kringle domains at the N-terminal regions (Castellino, F. J., and McCance, S. G. *CIBA Found Symp* (1997) 212: 46-60). These Kringle domains are approximately 80 amino acids long and some if them possess lysine binding capability. Kringle 1 from human plasminogen has the highest lysine binding affinity and was cloned from human plasminogen to generate a C-terminal fusion with solCD39, solCD39L3 or mutants thereof. The human plasminogen cDNA (IMAGE Clone #453147) was used as a template for PCR amplification using primers Kringle 5' c (SEQ. ID. NO: 79) and Kringle 3' (SEQ. ID. NO: 80). To ensure that the Kringle 1 domain can fold independent of the fusion to solCD39, solCD39L3 or mutants thereof, a 20 amino acid linker domain was added in two successive PCR amplifications using primers Kringle 5' b (SEQ. ID. NO: 78) and Kringle 5' a (SEQ. ID. NO: 77) with Kringle 3'. The resulting PCR product was directly cloned into pGEM-T easy (Promega, Madison, Wis.) and fully sequenced resulting in plasmid pAPT8989. The nucleotide sequence of the linker domain and Kringle 1 is represented as SEQ. ID. NO: 81 and the deduced amino acid sequence represented as SEQ. ID. NO: 82.

EXAMPLE 11

Cloning of a Clot Enhanced Apyrases

In order to generate C-terminal translational fusions with the linker plus Kringle 1 domain (pAPT8989), the termination codon for APT8429 (solCD39), APT8272 (solCD39L3), APT8742 (solCD39L3 R67G T69R), and APT8906 (solCD39L3 R67A T69R) was removed by site directed mutagenesis (Quick Change, Stratagene, La Jolla, Calif.) by introducing an in frame EcoRV site prior to the native termination codon. Table 5 lists the various template plasmids and resulting mutant plasmids generated by site directed mutagenesis.

TABLE 4

Kinetic parameters of ADPase enhanced apyrases

| | ATP | | | ADP | | | |
|---|---|---|---|---|---|---|---|
| | $K_m(\mu M)^{ATP}$ | $V_{max}(\times 10^{-4} s^{-1})^{ATP}$ | $V_{max}/K_m$ | $K_m(\mu M)^{ADP}$ | $V_{max}(\times 10^{-4} s^{-1})^{ADP}$ | $V_{max}/K_m$ | $(V/K)^{atp}/(V/K)^{adp}$ |
| APT8272 | 135.93 | 14.11 | 0.1038 | 134.09 | 4.67 | 0.0348 | 2.98 |
| APT8555 | 257.20 | 10.42 | 0.0405 | 257.00 | 4.94 | 0.0192 | 2.11 |
| APT8519 | 152.90 | 10.06 | 0.0658 | 281.80 | 5.64 | 0.0200 | 3.29 |
| APT8906 | 10.00 | 4.40 | 0.4400 | 27.00 | 4.40 | 0.1630 | 2.70 |
| APT8742 | 29.09 | 4.77 | 0.1639 | 46.42 | 6.26 | 0.1348 | 1.22 |
| APT8429 | 3.48 | 0.25 | 0.0706 | 11.00 | 0.35 | 0.0315 | 2.24 |
| APT8848 | 25.34 | 1.20 | 0.0473 | 32.14 | 0.90 | 0.0281 | 1.68 |
| APT8864 | 52.51 | 3.18 | 0.0607 | 94.81 | 2.52 | 0.0266 | 2.28 |
| APT8812 | 52.69 | 2.48 | 0.0470 | 90.22 | 1.48 | 0.0164 | 2.87 |
| APT8828 | 45.87 | 2.38 | 0.0520 | 35.00 | 1.40 | 0.0401 | 1.30 |

These results are shown graphically in FIG. 8A.

TABLE 5

Apyrase plasmids mutated to remove the termination codon for C-termal fusions

| Gene | Template Plasmid | Mutant Plasmid | Mutagenesis Primers | SEQ. ID. NO: Nucleotide | Peptide |
|---|---|---|---|---|---|
| CD39 RV | pAPT7987 | pAPT8926 | 23, 24 | 83 | 84 |
| CD39L3 RV | pAPT7983 | pAPT8359 | 49, 50 | 85 | 86 |
| CD39L3 R67A T69R RV | pAPT8461 | pAPT8916 | 49, 50 | 87 | 88 |
| CD39L3 R67G T69R RV | pAPT8470 | pAPT8922 | 49, 50 | 89 | 90 |

Following mutagenesis the coding frames from the various mutants were excised from the respective plasmids using restriction enzyme EcoRV and cloned into EcoRV digested and calf intestine alkaline phosphatase (CIAP) treated pAPT8989. Following successful translational fusion to the linker plus Kringle 1 of pAPT8989, the entire open reading frame of the apyrase translationally fused to linker plus Kringle 1 was excised using the restriction enzyme SmaI and cloned directly into SrfI and CIAP treated pSEQTag2 SrfI. The resulting plasmids generated are listed in Table 6.

TABLE 6

Clot enhanced apyrase plasmids generated by C-terminal translational fusion of Human Plasminogen Kringle 1 domain.

| Gene | Plasmid | Base Plasmid Type | SEQ. ID. NO: Nucleotide | Peptide | Expression Plasmid/Protein | Base Expression Plasmid |
|---|---|---|---|---|---|---|
| Linker + Kringle | pAPT8989 | pGEM-T Easy | 81 | 82 | — | — |
| CD39 + Linker + Kringle | pAPT9050 | pGEM-T Easy | 91 | 92 | pAPT9170/APT9170 | pSeqTag2 SrfI |
| CD39L3 + Linker + Kringle | pAPT9018 | pGEM-T Easy | 93 | 94 | pAPT9150/APT9150 | pSeqTag2 SrfI |
| CD39L3 R67A T69R + Linker + Kringle | pAPT9030 | pGEM-T Easy | 95 | 96 | pAPT9173/APT9173 | pSeqTag2 SrfI |
| CD39L3 R67G T69R + Linker + Kringle | pAPT9068 | pGEM-T Easy | 97 | 98 | pAPT9124/APT9124 | pSeqTag2 SrfI |

EXAMPLE 12

Expression and Purification of Clot Enhanced Apyrases

Expression plasmids listed in Table 6 were transfected FreeStyle™ 293-F cell lines (Invitrogen, Carlsbad, Calif.) in 100 ml spinners using transfectant 293fectin™ according to manufacturer's recommendations. Transfected cells were grown in FreeStyle™ 293 Expression Medium. After 3 days growth, the conditioned medium (CM) was collected and the cells were removed by centrifugation. The CM was 5-fold concentrated using Amicon Stirred Cells and Ultramembrane 10 kD MWCO. The concentrated CM was dialyzed against 1 L of 10 mM Tris-HCl, pH7.4 at 4° C. overnight. Dialyzed CM was loaded on 10 ml of L-Lysine column (Sigma, St. Louis, Mo.) equilibrated with 10 mM Tris-HCl, pH 7.4. After five volume of washing with the same buffer, non-specific bound proteins were washed with 10 mM Tris-HCl, pH7.4/100 mM NaCl. Kringle domain fused apyrases were eluted with 1× Tris buffered saline (Sigma, St. Louis, Mo.) and 0.2M ε-amino-n-caproic acid (EACA).

EXAMPLE 13

Activity of Clot Enhanced Apyrases

ADPase activity of the soluble apyrases and their clot enhanced apyrases were measured using 4 μl (APT8272, APT9150, APT8742, APT9124) or 20μl (APT8429, APT9170) of the desalted concentrated conditioned media (as described in Example 8) in assay buffer containing 50 mM Tris-HCl (pH 7.4), 8 mM $CaCl_2$ and 0.1 mM ADP or 1 mM ADP. The assay was performed as described in Example 9. Based on the measured activities, all the clot enhanced apyrases retained comparable ADPase activity suggesting the Kringle domain linked to C-terminus of the soluble apyrases did not have a significant impact on enzymatic activity (FIG. 8B).

EXAMPLE 14

Platelet Aggregation Studies

Human blood was collected via plastic tubing using acid citrate-dextrose (38 mM citric acid; 75 mM sodium citrate; 135 mM glucose) as anticoagulant from the healthy donor who did not ingest acetylsalicylic acid (ASA, aspirin) for the last week. Platelet-rich plasma (PRP) was prepared with an initial whole blood centrifugation (200×g, 15 min, 25° C.), and a second centrifugation of the PRP (90×g, 10 min, 25° C.) to eliminate residual erythrocytes and leukocytes (Gayle, III, et al., *J. Clinical Investigation* (1998) 101:1851-1859).

PRP (containing 1.2-1.5×$10^8$ platelets) was preincubated for 3 minutes at 37° C. in an aggregometer cuvette (Lumiaggregometer; Chrono-Log, Havertown, Pa.) alone or in combination with test samples containing solCD39 (APT8429), solCD39L3 (APT8272), solCD39L3 R67G T69R (APT8742) or solCD39L3 R67G T69R+linker+kringle (APT9124). Total volumes were adjusted to 300 μl with Tris-buffered saline. After the 3-min preincubation, ADP was added at the concentrations indicated and the aggregation response was recorded for 4-5 minutes.

Figure 9:
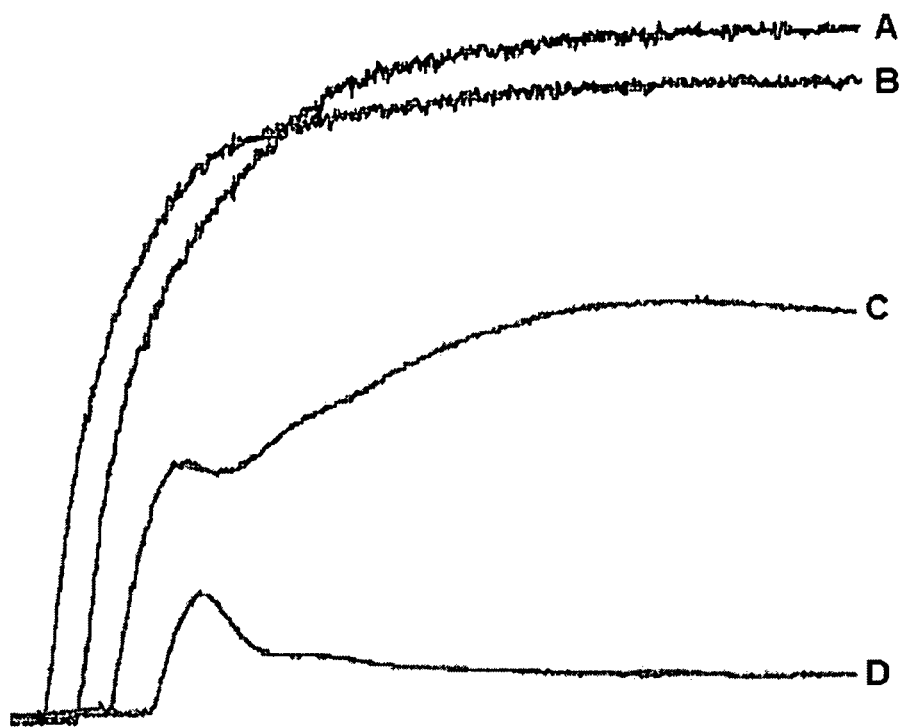
FIG. 9. Platelet aggregometer profiles of ADP induced human platelet aggregation. Platelets in platelet rich plasma (PRP) preincubated for 3 minutes at 37° C. were aggregated by the addition of (A) 1 μM, (B) 2 μM, (C) 5 μM or (D) 10 μM ADP.
Figure 10:
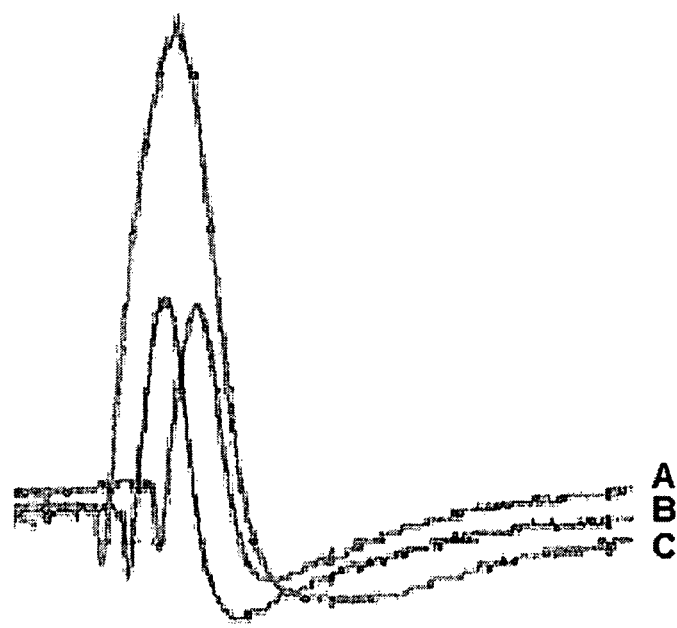
FIG. 10. Platelet aggregometer profiles of inhibition of ADP induced human platelet aggregation by ADPase enhanced apyrases. Platelet aggregation by 5 μM ADP was strongly inhibited by the added (A) 15 μg of APT8272, (B) 4 μg of APT8742 or (C) 1 μg of APT9124.
Figure 11:
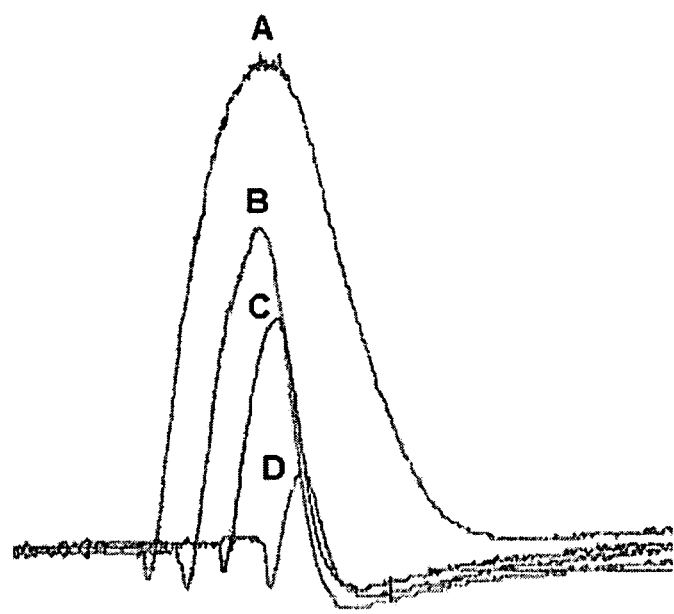
FIG. 11. Platelet aggregometer profiles of inhibition of ADP induced human platelet aggregation at different doses of APT9124. Platelet aggregation by 10 μM ADP was dose-dependently and very strongly inhibited, and traces returned to baseline by the added (A) 0.4 μg, (B) 1.2 μg, (C) 2 μg or (D) 6 μg of APT9124.

The following experiments demonstrate the effectiveness of the ADP enhanced apyrases for inhibiting and reversing ADP induced platelet aggregation in vitro. Specifically, PRP was preincubated for 3 min followed by the addition of 1 μM, 2 μM, 5 μM or 10 μM ADP to verify that the platelet aggregation was ADP-dose dependent (FIG. 9). Following proper ADP induced platelet aggregation response, PRP was preincubated for 3 min followed by the addition of 15 μg of APT8272 or 4 μg of APT8742 or 1 μg of APT9124 and 5 μM ADP, demonstrating that platelet aggregation was strongly inhibited by all the enzymes preparations. Based on the platelet aggregation response curves it was estimated that ATP8742 and APT9124 were 4-fold and 15-fold more potent than APT8272, respectively (FIG. 10). In order to demonstrate dose depended inhibition of platelet activation, PRP was preincubated for 3 min followed by the addition of 0.4 μg, 1.2 μg, 2 μg or 6 μg of APT9124 and 10 μM ADP. This result demonstrated that platelet aggregation is dose-dependently and very strongly inhibited, and traces return to baseline (FIG. 11).

Figure 12:
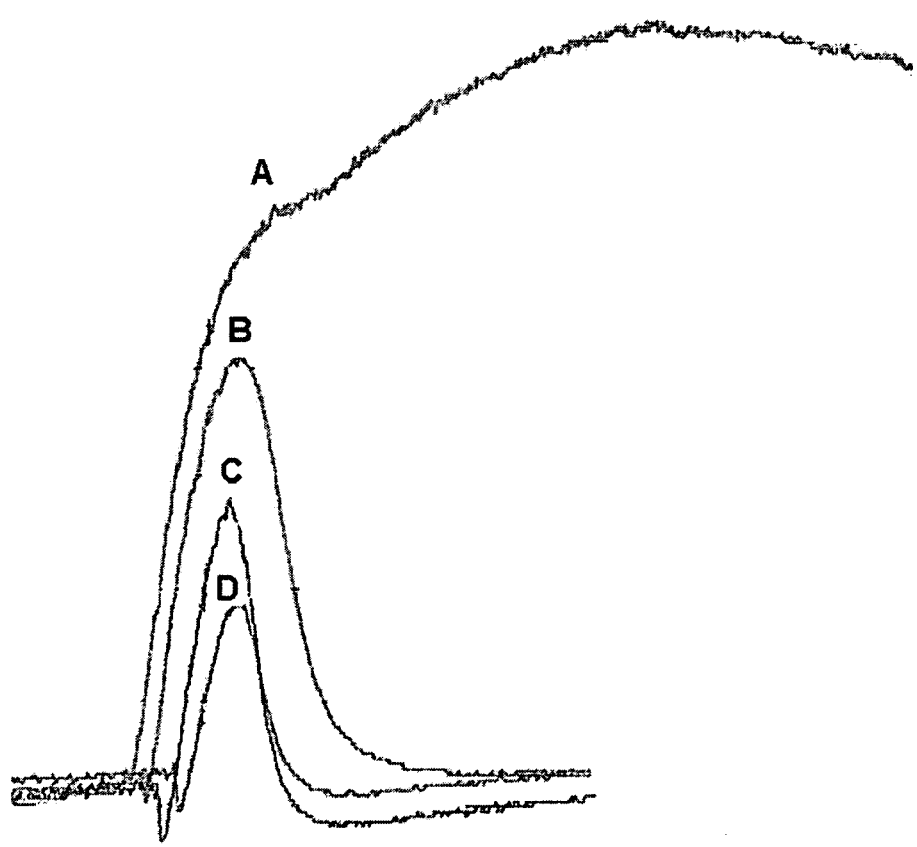
FIG. 12. ATPase induced potential pro-thrombotic effect and its neutralization by ADPase activity. Added 30 μM ATP hydrolyzed by ATPase activity to ADP that caused platelet aggregation followed by inhibition of ADPase activity hydrolyzed the ADP to AMP. Added apyrase are 15 μg of (A) APT8429, (B) APT8272, (C) APT8742 or (D) APT9124.
Figure 13:
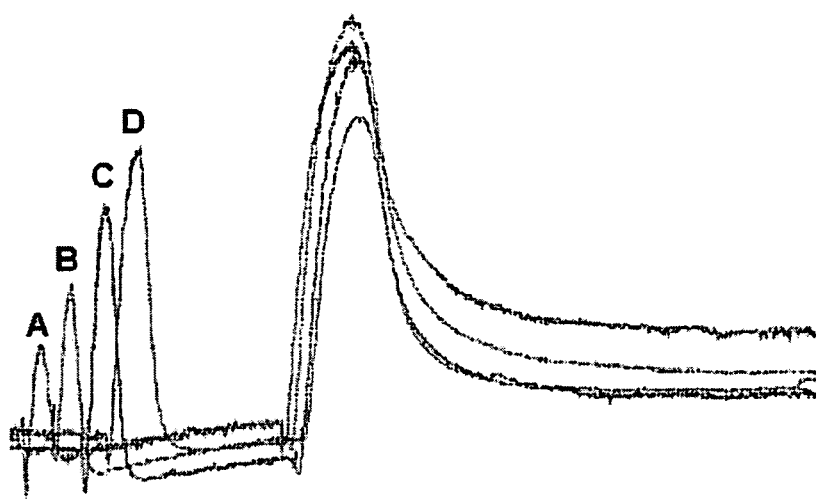
FIG. 13. Platelet aggregometer profiles of inhibition of ADP induced human platelet aggregation by 4 μg of APT9124 in the presence of ADP and ATP. (A) 10 μM ADP, (B) 10 μM ADP+10 μM ATP, (C) 10 μM ADP+50 μM ATP or (D) 10 μM ADP+100 μM ATP. Platelet aggregation from extra 300μ ATP after 5 minutes was also fully inhibited.

In order to demonstrate any potential pro-thrombotic effect from the ATPase activity, PRP was preincubated for 3 min followed by the addition of 15 μg APT8429, APT8272, APT8742 or APT9124 and 30 μM ATP. This experiment confirms that the platelet aggregation inhibitory activity was proportional to ADPase/ATPase ratio of the apyrases (FIG. 12). In another example, PRP was preincubated for 3 min followed by the addition of 4 μg of APT9124 and 10 μM ADP simultaneously added with 0 μM, 10 μM, 50 μM or 100 μM ATP. This experiment demonstrated in all cases that platelet aggregation was efficiently reversed by APT9124 in the presence of ADP and ATP and even totally reversed platelet aggregation by the addition of 300 μM ATP 5 minutes later indication that APT9124 strongly inhibits ATP-derived ADP induced platelet aggregation (FIG. 13).

EXAMPLE 15

90 Minute Temporary Middle Cerebral Artery Occlusion (MCAO) Model Study of APT8742

The efficacy of APT8742 was studied in a rat, 90-minute temporary middle cerebral artery occlusion (MCAO) model (Belayev, L., et al., *Stroke* (2003) 34:758-763). In the initial phase of the study, 24 male, Wistar rats weighing 300-340 grams were blindly randomized to vehicle with a dose of APT8742 of 1.5 mg/kg at 30 minutes after MCAO. The animals were anesthetized chloral hydrate for the MCAO surgery and this was maintained until reperfusion. The stroke model of MCAO temporary occlusion for 90 minutes was performed using the suture model. A coated 3-0 suture was inserted into the middle cerebral artery via the internal carotid artery and advanced until the tip of the suture was in the anterior cerebral artery. After 90 minutes the suture was withdrawn from the intracranial circulation. Temperature was maintained at 37 degrees Celsius and blood pressure was monitored continuously. Arterial blood gases were sampled at baseline and at 90 minutes after MCAO. After withdrawing the suture and discontinuing the anesthesia, the animals were allowed to recover and returned to the main animal medicine facility for overnight monitoring. At 24 hours after MCAO, the animals were evaluated with the Zea Longa neurological assessment scale and then sacrificed under deep chloral hydrate anesthesia. The brains were removed and stained with TTC for calculation of corrected infarct volumes. In the initial phase of the study, the treatment group was compared to the vehicle group used a 1-tailed paired t-test and in the study extension, the low-dose and vehicle groups were compared using this statistical approach.

The results of this initial phase of the study demonstrated that the infarct volume of the low-dose group had significantly lower smaller infarcts at 127.2 mm$^3$ than controls, 179.3 mm$^3$ with a p<0.05 (one tailed) (Table 7). The physiological variables showed no differences among the groups. The results of this study suggest that a low-dose (1.5 mg/kg) of APT8742 significantly reduces (>50% reduction in all responders) infarct volume by approximately 25-30% with no observable hemorrhage in the rat, temporary MCAO model. The results of this study suggest that APT8742 provides greater efficacy with a five fold lower therapeutic dosage than CD39.

TABLE 7

Reduction of infarct volume at 1.5 mg/kg dose of APT8742 in the rat temporary MCAO model

| | Infarct volume | |
|---|---|---|
| Animal No. | Vehicle (1× TBS) | APT8742 (1.5 mg/kg) |
| 1 | 155.7 | 173.9 |
| 2 | 116.2 | 68.1 |
| 3 | 159.6 | 262.9 |
| 4 | 145.3 | 148.6 |
| 5 | 165.4 | 231 |
| 6 | 148.2 | 46.6 |
| 7 | 323.8 | 46.9 |
| 8 | 135.4 | 62.9 |
| 9 | 161.2 | 85.2 |
| 10 | 219.8 | 95.2 |
| 11 | 230.6 | 91.2 |
| 12 | 190.8 | 214.4 |
| Average | 179.3 | 127.2 |

EXAMPLE 16

Cloning of Soluble Human Scan-1

A soluble version (generated by removal of the amino terminal 60 amino acids) of the Human SCAN-1 cDNA (gi: 22218108) was cloned by PCR directly from the IMAGE clone #1131402 (Image clone consortium (http://image.lln-l.gov) using PCR primers Scan 5' (SEQ. ID. NO: 99) and Scan 3' (SEQ ID. NO: 100) resulting in plasmid pAPT9005. A SmaI and NcoI restriction enzyme recognition site were transitionally introduced into the soluble SCAN-1 PCR product in order to aid future cloning into suitable mammalian and *E. coli* expression plasmids. The nucleotide sequence of the soluble SCAN-1 cDNA is represented as SEQ. ID. NO: 117 and the deduced amino acid sequence represented as SEQ. ID. NO: 118. In order to aid future cloning of soluble SCAN-1 into *E. coli* expression plasmids an internal NcoI restriction enzyme site was removed by site directed mutagenesis (Quick Change, Stratagene, La Jolla, Calif.) from soluble scan using the mutagenesis primers Scan-NcoI (SEQ. ID. NO: 107) and Scan-Nco2 (SEQ. ID. NO: 108) resulting in plasmid pAPT9231. The nucleotide sequence of SCAN-1 (NcoI) mutant is represented as SEQ. ID. NO: 119 and the deduced amino acid sequence is represented as SEQ. ID. NO: 120.

EXAMPLE 17

Design of ADP Enhanced Human Scan-1

Human SCAN-1 is a nucleoside-diphosphatase (EC 3.6.1.6) preferring UDP, GDP and IDP as much as 20 to 100 fold over ADP and CDP. (Failer, et al., *J. Biol. Chem.* (2002) 277:36978-36986; Smith, et al., *Arch. Biochem. Biophys.* (2002) 406:105-115; Murphy, et al., *Biochemistry* (2003)

42:2412-2421). The Km values for GDP and ADP were estimated to be 0.46 mM and 5.4 mM, respectively (Murphy, et al., *Biochemistry* (2003) 42:2412-2421). Therefore to convert human SCAN-1 to ADPase enhanced apyrase, its substrate binding site should be designed to accommodate ADP.

With no crystal structure of human SCAN-1 or a related apyrase available, we examined (using DeepView/Swiss-PdbViewer (Gues & Peitsch *Electrophoresis* (1997), 18:2714-2723; which can be found on the web at: www.expasy.org/spdbv) the physiochemical interaction between the nucleotide bases and protein residues surrounding the nucleotide bases bound to other proteins (for example, Phosphatases, Kinases and GTP binding proteins), whose structures were solved in the RCSB Protein Data Bank (which can be found on the web at: www.rcsb.org/pdb/index.html). Based on these studied of structures interaction with the purine and pyrimidine rings of the nucleotide bases, we observed the following:

The purine nucleotide ring (for example, guanine, inosine, adenine) has extra imidazole ring compared to the pyrimidine nucleotide ring (for example, uracil and cytosine), therefore the physical size of the nucleotide ring may cause discrepancy in the enzymes substrate preference.

Preferred substrates of UDP, GDP and IDP share a common cis-peptide bond in their pyrimidine nucleotide ring while the C4-keto group is replaced by a C4-amino group in the nucleotides ADP and CDP, therefore the enzymes substrate binding pocket, evolved to accommodate UDP, GDP and IDP, may not be preferable to binding ADP and CDP based on different hydrogen bonding interactions between the nucleotide bases and amino acid residues in the enzymes active site (FIG. 3).

Figure 14:
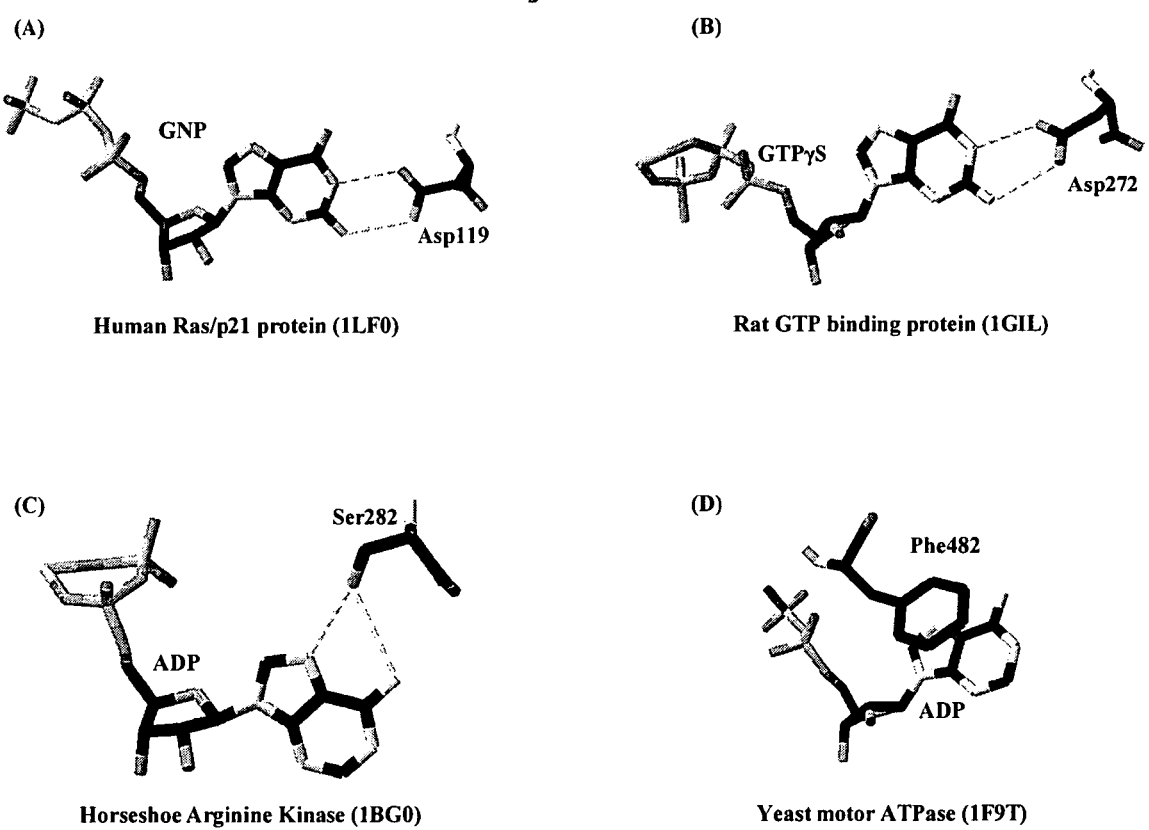
FIG. 14. Structural interactions of nucleotides with their biding proteins (A) GNP with human Ras protein, (B) GTPγS with rat GTP binding protein, (C) ADP with horseshoe arginine kinase and (D) ADP with yeast motor ATPase All the structures were obtained from the RCSB Protein Data (which can be found on the web at: rcsb.org/pdb/index.html).

Structural analysis of GDP or GTP binding proteins in the Protein Data Bank revealed that nucleotide guanine interacts with the protein through a series of hydrogen bonding interactions between two amino groups in the guanidine structure in the purine ring and the carboxyl group of an Aspartic acid of the protein (for example, human Ras protein or rat GTP-binding protein, FIGS. 14A, 14B).

Structural analysis of ADP or ATP binding proteins in the Protein Data Bank revealed that the nucleotide adenine interacts with the protein mostly through a single H-bonding interaction between adenine's C4-amino group and an appropriate proton acceptor group of the protein (for example, a hydroxyl group in arginine kinase FIG. 14C). Therefore apyrases may have replacement of Asp of GDPase s by very likely but not limited to Ser, Thr, Asn or Gln.

Structural analysis ADP binding proteins (for example, a yeast ATPase FIG. 14D) indicated that the adenine binding pocket of the protein preferably has an aromatic side chain residue, such as Phe, Tyr or Trp, within 4 Å distance contributing hydrophobic interaction with the purine and pyrimidine ring of the nucleotide base, therefore the aromatic residue will be conserved among known apyrases with ADP binding activity.

Based on the above considerations, we carefully analyzed two ClustalW multiple sequence alignment; first, the Human SCAN-1 aligned with its related proteins (for example, *Phlebotomus* apyrase, gi: 10443907; *Cimex* apyrase, gi: 4185746; Rat ER NDPase, gi: 21262131) (FIG. 15), and second Human SCAN-1 aligned with the *Cimex* apyrase (gi: 4185746) (FIG. 16). Notably, SCAN-1 shares 45% amino acid sequence identity with *Cimex* bed bug apyrase. Both enzymes are strictly dependent on Ca2+. However, the substrate specificities are strikingly different. The bed bug apyrase hydrolyzes ADP and ATP efficiently, whereas SCAN-1 hydrolyzes UDP, GDP, and IDP 20-50 fold faster than ADP and CDP and hydrolyzes ATP only to a very small extent (Murphy, D., et al., *Biochemistry* (2003) 42:2412-2421). Hence, the key residues determining nucleotide specificities can be identified by correct sequence alignment. Based on observation 4 above, a conserved serine or threonine residue (for example, *Cimex* S191) was identified in the blood sucking insect apyrases with a substrate specificity for ADP, while SCAN-1 and related enzymes with a substrate specificity preference of GDP and CDP maintained a leucine (for example, L199) at this position. Also based on observation 4, conserved Asp or Glu residues (for example SCAN-1 E279 or D282) that were conserved among SCAN-1 like enzymes were also candidates for engineering ADP specificity. Other amino acids such as glycine, cysteine or proline conserved in one group (for example SCAN-1 related enzymes) and not in the other group (for example, blood sucking insect apyrases) were studied due to their potential roles in forming the protein's three dimensional structure. Based on observation 5, aromatic residues that were conserved in apyrases (for example, blood sucking insect apyrases) and not in SCAN-1 were also potential candidates for engineering protein specificity due to the aromatic residues role for adenine ring binding. Following were the list of candidates came out from the analyses and numbers are of human SCAN-1. Residues for engineered human SCAN-1 were selected from counter residues in, for example the *Cimex* apyrase; leucine 199 vs. serine 191 in for *Cimex* apyrases (adenine binding); isoleucine 252 vs. tryptophan 244 in *Cimex* apyrases (adenine binding); glutamine 279 vs. serine 271 in *Cimex* apyrases (possible H-bonds for guanidine binding); aspartate 282 vs. phenylalanine 274 in *Cimex* apyrases (possible H-bonds for guanidine binding); Glu334 vs. valine 327 in *Cimex* apyrases (possible H-bonds for guanidine binding); Gly338 vs. aspartate 331 in *Cimex* apyrases (important structural change).

These mutations identified can be introduced into SCAN-1 as individual point mutations or in various combinations. Also one skilled in the art may recognize other amino acid substitutions that will have similar effects on altering the substrate specificity of SCAN-1 from GDP, CDP, and UDP to ADP.

EXAMPLE 18

Mutagenesis of Human Scan-1

Site directed mutagenesis (Quick Change, Stratagene, LaJolla, Calif.) was performed on soluble Human Scan-1 using pAPT9231 as a template. The point mutations described in Example 21 were introduced into soluble SCAN-1 as described in Table 8. Following site directed mutagenesis the sequence of the entire open reading frame of all the mutants generated was verified by DNA sequence analysis. The resulting clones generated by site directed mutagenesis and their corresponding mammalian expression plasmids are identified in Table 8.

TABLE 8

Coding sequence and mammalian expression plasmids of wild type and mutant forms of soluble SCAN-1.

| Gene | Plasmid | Base Plasmid Type | SEQ. ID. NO: Mutagenesis Primers | Nucleotide | Peptide | Expression Plasmid/Protein | Base Expression Plasmid |
|---|---|---|---|---|---|---|---|
| sol SCAN-1 | pAPT9005 | pGEM-T Easy | — | 117 | 118 | pAPT9198/APT9198 | pSeqTag2 SrfI |
| sol SCAN-1 L199S | pAPT9241 | pGEM-T Easy | 109, 110 | 121 | 122 | pAPT9267/APT9267 | pSeqTag2 SrfI |
| sol SCAN-1 I252W | pAPT9246 | pGEM-T Easy | 111, 112 | 123 | 124 | pAPT9275/APT9275 | pSeqTag2 SrfI |
| sol SCAN-1 E279S, D282F | pAPT9247 | pGEM-T Easy | 113, 114 | 125 | 126 | pAPT9279/APT9279 | pSeqTag2 SrfI |
| sol SCAN-1 E334V, G338D | pAPT9256 | pGEM-T Easy | 115, 116 | 127 | 128 | pAPT9285/APT9285 | pSeqTag2 SrfI |

EXAMPLE 19

Expression of Human Scan-1

In order to test the in vitro enzymatic properties of the engineered soluble SCAN-1 clones, 30 µg of mammalian expression plasmid DNA (Table 8) were transfected into 293T cells (GenHunter, Nashville, Tenn.) in four 100 mm dishes using the transfectant FuGene 6 (Roche) according to manufacturer's recommendations. Transfected cells were grown for three days in DMEM medium, supplemented with 1% BCS, 1% MEM non-essential amino acids, 1% penicillin-streptomycin and 2 mM L-glutamine. Following growth, the conditioned medium (CM) was collected and the cell debris was removed by centrifugation. The protein in CM was harvested by centrifugation following 65% ammonium sulfate precipitation. The protein pellet was dissolved in 2.5 ml of 20 mM Tris-HCl, pH 7.4, and desalted through EconoPac 10DG desalting column (BioRad, Hercules, Calif.) resulting in approximately 4 ml of collected desalted extract resulting in approximately 5-fold concentration of the secreted soluble SCAN-1 enzymes. The samples were stored at 4° C. until assayed (Example 24).

EXAMPLE 20

Activity of Human Scan-1

NDPase activity of the soluble wild type and soluble engineered human SCAN-1 proteins were measured with 10 µl (wild type, APT9279, APT9285) or 5 µl (APT9267, APT9275) of the concentrated conditioned media in 50 mM Tris-HCl buffer (pH 7.4) containing 8 mM CaCl$_2$ and 1 mM ADP, 1 mM ATP, 1 mM GDP, 1 mM CDP, or 1 mM UDP. The assay was performed as described in Example 9.

Figure 17:
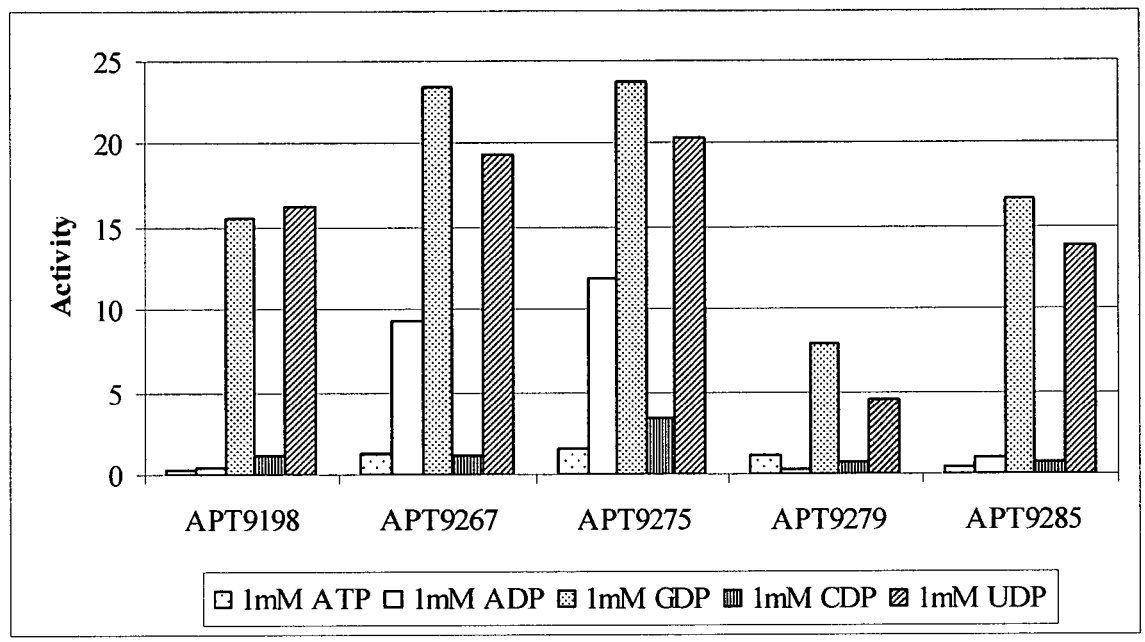
FIG. 17. Nucleotidase activities of APT9198, APT9267, APT9275, APT9279, and APT9285 human SCAN-1 apyrases vs. 1 mM ATP, ADP, GDP, CDP and UDP.

Based on the initial enzymatic analysis, ADPase activity was estimated to be improved in the engineered SCAN-1 enzymes ATP9285 (E334V&G338D), APT9267 (L199S), and APT9275 (I252W) by 4-fold, 32-fold and 46-fold, respectively (FIG. 17). Due to the sensitivity of the colorimetric assay method employed, ADPase activity of ATP9275 was re-measured with a 10-fold dilution of the enzyme resulting in at least a 100-fold improvement of ADPase activity compared to wildtype. These results of the engineered SCAN-1 support the rationale that adenine binding may be improved by hydrogen bond formation (L199S) or by hydrophobic interactions (I252W).

Detectable ATPase activity was also observed in the engineered SCAN-1 APT9267 and APT9275. UDP and GDPases activities of the engineered SCAN-1 enzymes remained comparable (APT9285) or better (APT9267, APT9275) then the wild type enzyme. APT9279 has slightly poorer enzyme performance compared to the wild type enzyme. Individual point mutations, for example E279S, D282F, E334V, and G338D may be studied to assess the implications of single point mutations on ADP, ATP, CDP, GTP and UTP binding.

The effect of pH on enzyme activity was also studied with APT9267 and APT9275 at human blood physiological pH (pH 7.4) versus the reported optimal pH for the wild type enzyme (pH 6.5). Both SCAN-1 mutants APT9267 and APT9275 had >95% activity at the preferred physiological pH 7.4. Based on the preliminary enzymatic analysis, the human SCAN-1 mutant apyrases, for example, APT9267 and APT9275 are candidates as anti-platelet agents useful for preventing or reversing platelet activation in human blood compared. Additional kinetic studies may be employed to measure $K_m$ and $V_{max}$ of the SCAN-1 mutants.

EXAMPLE 21

Cloning, Expression and Activity of Soluble CD39L4

The soluble form (deletion of N-terminal 19 amino acids) of CD39L4 (solCD39L4), was cloned from normal Human kidney cDNA (ResGen D8070-01, Lot PX1091901) by PCR using the primers CD39L4-SMA 5' (SEQ. ID. NO: 129) and CD39L4-SMA 3' (SEQ. ID. NO: 130). The resulting PCR product was digested with SmaI and subcloned directly into pSP72 (Promega Madison, Wis.) resulting in plasmid pAPT7980. The nucleotide sequence of the cloned solCD39L4 was determined using sequencing primers CD39L41-10 (SEQ. ID. NOs: 131-140). The nucleotide sequence is reported as SEQ. ID. NO: 141 and the deduced amino acid sequence reported as SEQ. ID. NO: 142.

Figure 18:
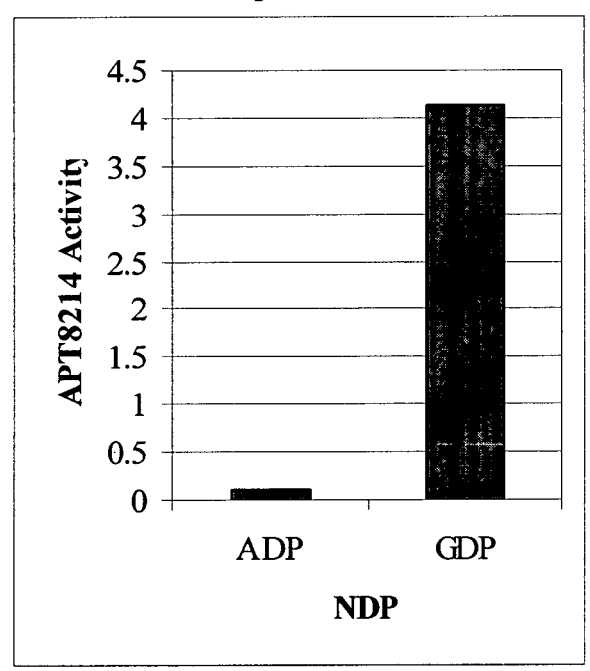
FIG. 18. Nucleotidase activity of human CD39L4 (APT8214) vs. 200 μM of ADP and GDP.

The SmaI fragment solCD39L4 was translationally fused to the SrfI site of pSEQTAQ2SrfI resulting in plasmid pAPT8214. The plasmid was transfected into HEK293T cells and activity measured as in Example 8. Based on the activity measured for APT8214 (FIG. 18) it was determined that the solCD39L4 has a strong preference for GDP over ADP. Protein engineering may be employed to alter the substrate specificity of solCD39L4 from GDP to ADP.

The invention claimed is:

1. An ADPase enhanced apyrase, which ADPase enhanced apyrase is a modified form of a soluble form of CD39L3 or a fusion protein of said soluble form with heterologous sequence wherein said modification results in
   increased ADPase activity; or
   substantially the same ADPase activity combined with decreased ATPase activity as compared with the native apyrase,
   wherein the enhanced apyrase contains two amino acid substitutions;
   wherein one of said two amino acid substitutions is either at position 67 or at position 69 of human CD39L3 as set forth in SEQ ID NO: 56 or positions corresponding thereto in an isoenzyme of human CD39L3,
   wherein said soluble form of human CD39L3 lacks a 43 amino acids sequence from the N-terminus and lacks a 44 amino acid sequence from the C-terminus of SEQ ID NO: 56.

2. The ADPase enhanced apyrase of claim 1, wherein said substitutions are at positions 67 and 69 of CD39L3 (SEQ ID NO: 56), in soluble form or positions corresponding thereto in an isoenzyme of human CD39L3 in soluble form.

3. The ADPase enhanced apyrase of claim 2, wherein the mutations replace Arg at position 67 with Gly and Thr at position 69 with Arg, designated APT8742, or wherein the mutations replace Arg at position 67 with Ala and Thr at position 69 with Arg, designated APT8906.

4. A composition which comprises the ADPase enhanced apyrase of claim 1 in admixture with a pharmaceutically acceptable carrier.

5. The ADPase enhanced apyrase of claim 1, which is included in a fusion protein comprising a targeting region.

6. The ADPase enhanced apyrase of claim 5, wherein said targeting region binds to thrombus and/or to activated platelets.

7. The ADPase enhanced apyrase of claim 6, wherein said targeting region is the kringle region of human plasminogen.

8. A composition which comprises the ADPase enhanced apyrase of claim 5 in admixture with a pharmaceutically acceptable carrier.

9. A method to inhibit platelet aggregation which method comprises contacting a system in which platelet aggregation occurs with the ADPase enhanced apyrase of claim 1 or a composition thereof that includes a pharmaceutically acceptable carrier.

10. A method to inhibit platelet aggregation which method comprises contacting a system in which platelet aggregation occurs with the ADPase enhanced apyrase of claim 5 or a composition thereof that includes a pharmaceutically acceptable carrier.

11. A method to treat thrombosis in a subject which method comprises administering to a subject in need thereof an effective amount of the ADPase enhanced apyrase of claim 1 or a composition thereof that includes a pharmaceutically acceptable carrier.

12. A method to treat thrombosis in a subject which method comprises administering to a subject in need thereof an effective amount of the ADPase enhanced apyrase of claim 5 or composition thereof that includes a pharmaceutically acceptable carrier.

13. A method to treat stroke, coronary artery disease, injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders or thrombotic disorders in a subject which method comprises administering to a subject in need thereof an effective amount of the ADP enhanced apyrase of claim 1 or a composition thereof that includes a pharmaceutically acceptable carrier.

14. The ADP enhanced apyrase of claim 3 which is APT8742.

15. A method to treat stroke, coronary artery disease, injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders or thrombotic disorders in a subject which method comprises administering to a subject in need thereof an effective amount of the ADP enhanced apyrase of claim 5 or a composition thereof that includes a pharmaceutically acceptable carrier.

16. A method to treat an inflammatory disorder in a subject which method comprises administering to a subject in need thereof an effective amount of the ADPase enhanced apyrase of claim 1 or a composition thereof that includes a pharmaceutically acceptable carrier.

17. A method to treat an inflammatory disorder in a subject which method comprises administering to a subject in need thereof an effective amount of the ADPase enhanced apyrase of claim 5 or a composition thereof that includes a pharmaceutically acceptable carrier.

18. A composition which comprises the ADPase enhanced apyrase of claim 2 in admixture with a pharmaceutically acceptable carrier.

19. The ADPase enhanced apyrase of claim 2, which is included in a fusion protein comprising a targeting region.

20. A composition which comprises the ADPase enhanced apyrase of claim 19 in admixture with a pharmaceutically acceptable carrier.

21. A method to inhibit platelet aggregation which method comprises contacting a system in which platelet aggregation occurs with the ADPase enhanced apyrase of claim 2 or a composition thereof that includes a pharmaceutically acceptable carrier.

22. A method to inhibit platelet aggregation which method comprises contacting a system in which platelet aggregation occurs with the ADPase enhanced apyrase of claim 19 or a composition thereof that includes a pharmaceutically acceptable carrier.

23. A method to treat thrombosis in a subject which method comprises administering to a subject in need thereof an effective amount of the ADPase enhanced apyrase of claim 2 or a composition thereof that includes a pharmaceutically acceptable carrier.

24. A method to treat thrombosis in a subject which method comprises administering to a subject in need thereof an effective amount of the ADPase enhanced apyrase of claim 19 or a composition thereof that includes a pharmaceutically acceptable carrier.

25. A method to treat stroke, coronary artery disease, injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders or thrombotic disorders in a subject which method comprises administering to a subject in need thereof an effective amount of the ADP enhanced apyrase of claim 2 or a composition thereof that includes a pharmaceutically acceptable carrier.

26. A method to treat stroke, coronary artery disease, injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders or thrombotic disorders in a subject which method comprises administering to a subject in need thereof an effective amount of the ADP enhanced apyrase of claim 19 or a composition thereof that includes a pharmaceutically acceptable carrier.

27. A method to treat an inflammatory disorder in a subject which method comprises administering to a subject in need thereof an effective amount of the ADPase enhanced apyrase of claim 2 or composition thereof that includes a pharmaceutically acceptable carrier.

28. A method to treat an inflammatory disorder in a subject which method comprises administering to a subject in need thereof an effective amount of the ADPase enhanced apyrase of claim 19 or composition thereof that includes a pharmaceutically acceptable carrier.

\* \* \* \* \*

SEQUENCE LISTING

<160> NUMBER OF SEQ ID NOS: 184

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1
ttggatccat ggagggaacc aaggacctga c                          31

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
cctcgaggat cctcactata ccatatcttt ccagaaa                    37

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
ggcgtggtgc atcaagtag                                        19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
cctttgactt ccagggtgc                                        19

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ggcaaggact acaatgtc                                         18

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
ccatcaaagc atcctggag                                        19

<210> SEQ ID NO 7
<211> LENGTH: 19

-continued

```
<212> TYPE: DNA
<213> ORGANISM: Artificial Sequence
<220> FEATURE:
<223> OTHER INFORMATION: Primer

<400> SEQUENCE: 7
gaagtacctg agtgaatac                                               19

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gtattcactc aggtacttc                                               19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
ctccaggatg ctttgatgg                                               19

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
gacattgtag tccttgcc                                                18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcaccctgga agtcaaggg                                               20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ctacttgatg caccacgcc                                               19

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
```
aaaacccggg atgcagaaca aagcattgcc agaaaacg					38

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
aaaacccggg tcactaatag gtggagtggg agagagg					37

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gatgcgggtt cttctgggac aagtttatac atc					33

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gatgtataaa cttgtcccag aagaacccgc atc					33

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
gatgcgggtt cttctgcgac aagtttatac atc					33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
gatgtataaa cttgtcgcag aagaacccgc atc					33

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
gtgctggatg cgggttcttc tgggacacgc ttatacatct ataag			45

<210> SEQ ID NO 20
<211> LENGTH: 45
<212> TYPE: DNA
<213> ORGANISM: Artificial Sequence

```
<220> FEATURE:
<223> OTHER INFORMATION: Primer

<400> SEQUENCE: 20
cttatagatg tataagcgtg tcccagaaga acccgcatcc agcac            45

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
gtgctggatg cgggttcttc tgcgacacgc ttatacatct ataag            45

<210> SEQ ID NO 22
<211> LENGTH: 45
<212> TYPE: DNA
<213> ORGANISM: Artificial Sequence
<220> FEATURE:
<223> OTHER INFORMATION: Primer

<400> SEQUENCE: 22
cttatagatg tataagcgtg tcgcagaaga acccgcatcc agcac            45

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
ctctcccact ccaccgatat ctgacccggg gatcc                       35

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
ggatccccgg gtcagatatc ggtggagtgg gagag                       35

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ttggatccat ggtcactgtg ctgacccgcc                             30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
ttggatccat ggagatccac aagcaagagg                             30
```

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
cctcgaggat cctatcagtc agaatccact gcatggtc                                38

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
cctcgaggat cctatcagac aggtggttct atgggcag                                38

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ccggagtggt cagtcaaacc                                                    20

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30 gcccttttgac tttagggg                                                     18

<210> SEQ ID NO 31
<211> LENGTH: 16
<212> TYPE: DNA
<213> ORGANISM: Artificial Sequence
<220> FEATURE:
<223> OTHER INFORMATION: Primer

<400> SEQUENCE: 31
ggctacgtat acacgc                                                        16

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
ggtggcttcc atatttgac                                                     19

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
gatgaggtat atgcccgc                                              18

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
gcgggcatat acctcatc                                              18

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
gtcaaatatg gaagccacc                                             19

<210> SEQ ID NO 36
<211> LENGTH: 16
<212> TYPE: DNA
<213> ORGANISM: Artificial Sequence
<220> FEATURE:
<223> OTHER INFORMATION: Primer

<400> SEQUENCE: 36
gcgtgtatac gtagcc                                                16

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
taaagtcaaa gggctggg                                              18

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ggtttgactg accactccgg                                            20

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
aaaacccggg atgcagatcc acaagcaaga ggtcctccc                       39

<210> SEQ ID NO 40

```
<211> LENGTH: 35
<212> TYPE: DNA
<213> ORGANISM: Artificial Sequence
<220> FEATURE:
<223> OTHER INFORMATION: Primer

<400> SEQUENCE: 40
aaaacccggg ctatcagaca ggtggttcta tgggc                              35

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
ggatgccggg tcttcagcga ccacagtcta cgtg                               34

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
cacgtggact gtggtcgctg aagacccggc atcc                               34

<210> SEQ ID NO 43
<211> LENGTH: 34
<212> TYPE: DNA
<213> ORGANISM: Artificial Sequence
<220> FEATURE:
<223> OTHER INFORMATION: Primer

<400> SEQUENCE: 43
ggatgccggg tcttcaggga ccacagtcta cgtg                               34

<210> SEQ ID NO 44
<211> LENGTH: 34
<212> TYPE: DNA
<213> ORGANISM: Artificial Sequence
<220> FEATURE:
<223> OTHER INFORMATION: Primer

<400> SEQUENCE: 44
cacgtacact gtggtccctg aagacccggc atcc                               34

<210> SEQ ID NO 45
<211> LENGTH: 45
<212> TYPE: DNA
<213> ORGANISM: Artificial Sequence
<220> FEATURE:
<223> OTHER INFORMATION: Primer

<400> SEQUENCE: 45
gctggatgcc gggtcttcag cgacccgcgt ctacgtgtat caatg                   45

<210> SEQ ID NO 46
<211> LENGTH: 45
<212> TYPE: DNA
<213> ORGANISM: Artificial Sequence
<220> FEATURE:
<223> OTHER INFORMATION: Primer

<400> SEQUENCE: 46
```
cattgataca cgtagacgcg ggtcgctgaa gacccggcat ccagc       45

<210> SEQ ID NO 47
<211> LENGTH: 45
<212> TYPE: DNA
<213> ORGANISM: Artificial Sequence
<220> FEATURE:
<223> OTHER INFORMATION: Primer

<400> SEQUENCE: 47
gctggatgcc gggtcttcag gacccgcgt ctacgtgtat caatg        45

<210> SEQ ID NO 48
<211> LENGTH: 45
<212> TYPE: DNA
<213> ORGANISM: Artificial Sequence
<220> FEATURE:
<223> OTHER INFORMATION: Primer

<400> SEQUENCE: 48
cattgataca cgtagacgcg ggtccctgaa gacccggcat ccagc       45

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
cgtctgccca tagaaccaga tatctgatag cccggggatc ctct        44

<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50
agaggatccc cgggctatca gatatctggt tctatgggca gacg        44

<210> SEQ ID NO 51
<211> LENGTH: 36
<212> TYPE: DNA
<213> ORGANISM: Artificial Sequence
<220> FEATURE:
<223> OTHER INFORMATION: Primer

<400> SEQUENCE: 51
tccactggtg acgcgcccgg gccggccagg cgcgcc                 36

<210> SEQ ID NO 52
<211> LENGTH: 36
<212> TYPE: DNA
<213> ORGANISM: Artificial Sequence
<220> FEATURE:
<223> OTHER INFORMATION: Primer

<400> SEQUENCE: 52
ggggcgcctg gccggcccgg gcgcgtcacc agtgga                 36

<210> SEQ ID NO 53
<211> LENGTH: 1557
<212> TYPE: DNA

<213> ORGANISM: Homo sapiens

<400> SEQUENCE: 53

```
atggagggaa ccaaggacct gacaagccag cagaaggagt ctaacgtgaa gacattttgc      60
tccaagaata tcctagccat ccttggcttc tcctctatca tagctgtgat agctttgctt     120
gctgtggggt tgacccagaa caaagcattg ccagaaaacg ttaagtatgg gattgtgctg     180
gatgcgggtt cttctcacac aagtttatac atctataagt ggccagcaga aaaggagaat     240
gacacaggcg tggtgcatca agtagaagaa tgcagggtta aggtcctgga atctcaaaa      300
tttgttcaga aagtaaatga aataggcatt tacctgactg attgcatgga agagctagg      360
gaagtgattc caaggtccca gcaccaagag acacccgttt acctgggagc acggcaggc      420
atgcggttgc tcaggatgga aagtgaagag ttggcagaca gggttctgga tgtggtggag     480
aggagcctca gcaactaccc ctttgacttc cagggtgcca ggatcattac tggccaagag     540
gaaggtgcct atgctggat tactatcaac tatctgctgg gcaaattcag tcagaaaaca      600
aggtggttca gcatagtccc atatgaaacc aataatcagg aaacctttgg agctttggac     660
cttgggggag cctctacaca agtcactttt gtaccccaaa accagactat cgagtcccca     720
gataatgctc tgcaatttcg cctctatggc aaggactaca atgtctacac acatagcttc     780
tgtgctatg ggaaggatca ggcactctgg cagaaactgg ccaaggacat tcaggttgca      840
agtaatgaaa ttctcaggga cccatgcttt catcctggat ataagaaggt agtgaacgta     900
agtgaccttt acaagacccc ctgcaccaag agatttgaga tgactcttcc attccagcag     960
tttgaaatcc agggtattgg aaactatcaa caatgccatc aaagcatcct ggagctcttc    1020
aacaccagtt actgccctta ctcccagtgt gccttcaatg gattttcttg ccaccactc     1080
caggggat ttgggcatt ttcagctttt tactttgtga tgaagttttt aaacttgaca       1140
tcagagaaag tctctcagga aaaggtgact gagatgatga aaaagttctg tgctcagcct    1200
tgggaggaga taaaaacatc ttacgctgga gtaaaggaga agtacctgag tgaatactgc    1260
ttttctggta cctacattct ctccctcctt ctgcaaggct atcatttcac agctgattcc    1320
tgggagcaca tccatttcat ggcaagatc agggcagcg acgccggctg gactttgggc     1380
tacatgctga acctgaccaa catgatccca gctgagcaac cattgtccac acctctctcc    1440
cactccacct atgtcttcct catggttcta ttctccctgg tccttttcac agtggccatc    1500
ataggcttgc ttatctttca caagccttca tatttctgga agatatggt atagtga       1557
```

<210> SEQ ID NO 54
<211> LENGTH: 517
<212> TYPE: PRT
<213> ORGANISM: Homo sapiens

<400> SEQUENCE: 54

```
Met Glu Gly Thr Lys Asp Leu Thr Ser Gln Gln Lys Glu Ser Asn Val
  1               5                  10                  15

Lys Thr Phe Cys Ser Lys Asn Ile Leu Ala Ile Leu Gly Phe Ser Ser
             20                  25                  30

Ile Ile Ala Val Ile Ala Leu Leu Ala Val Gly Leu Thr Gln Asn Lys
         35                  40                  45

Ala Leu Pro Glu Asn Val Lys Tyr Gly Ile Val Leu Asp Ala Gly Ser
     50                  55                  60

Ser His Thr Ser Leu Tyr Ile Tyr Lys Trp Pro Ala Glu Lys Glu Asn
 65                  70                  75                  80
```

```
Asp Thr Gly Val Val His Gln Val Glu Glu Cys Arg Val Lys Gly Pro
                85                  90                  95
Gly Ile Ser Lys Phe Val Gln Lys Val Asn Glu Ile Gly Ile Tyr Leu
            100                 105                 110
Thr Asp Cys Met Glu Arg Ala Arg Glu Val Ile Pro Arg Ser Gln His
        115                 120                 125
Gln Glu Thr Pro Val Tyr Leu Gly Ala Thr Ala Gly Met Arg Leu Leu
    130                 135                 140
Arg Met Glu Ser Glu Glu Leu Ala Asp Arg Val Leu Asp Val Val Glu
145                 150                 155                 160
Arg Ser Leu Ser Asn Tyr Pro Phe Asp Phe Gln Gly Ala Arg Ile Ile
                165                 170                 175
Thr Gly Gln Glu Glu Gly Ala Tyr Gly Trp Ile Thr Ile Asn Tyr Leu
            180                 185                 190
Leu Gly Lys Phe Ser Gln Lys Thr Arg Trp Phe Ser Ile Val Pro Tyr
        195                 200                 205
Glu Thr Asn Asn Gln Glu Thr Phe Gly Ala Leu Asp Leu Gly Gly Ala
    210                 215                 220
Ser Thr Gln Val Thr Phe Val Pro Gln Asn Gln Thr Ile Glu Ser Pro
225                 230                 235                 240
Asp Asn Ala Leu Gln Phe Arg Leu Tyr Gly Lys Asp Tyr Asn Val Tyr
                245                 250                 255
Thr His Ser Phe Leu Cys Tyr Gly Lys Asp Gln Ala Leu Trp Gln Lys
            260                 265                 270
Leu Ala Lys Asp Ile Gln Val Ala Ser Asn Glu Ile Leu Arg Asp Pro
        275                 280                 285
Cys Phe His Pro Gly Tyr Lys Lys Val Val Asn Val Ser Asp Leu Tyr
290                 295                 300
Lys Thr Pro Cys Thr Lys Arg Phe Glu Met Thr Leu Pro Phe Gln Gln
305                 310                 315                 320
Phe Glu Ile Gln Gly Ile Gly Asn Tyr Gln Gln Cys His Gln Ser Ile
                325                 330                 335
Leu Glu Leu Phe Asn Thr Ser Tyr Cys Pro Tyr Ser Gln Cys Ala Phe
            340                 345                 350
Asn Gly Ile Phe Leu Pro Pro Leu Gln Gly Asp Phe Gly Ala Phe Ser
        355                 360                 365
Ala Phe Tyr Phe Val Met Lys Phe Leu Asn Leu Thr Ser Glu Lys Val
    370                 375                 380
Ser Gln Glu Lys Val Thr Glu Met Met Lys Lys Phe Cys Ala Gln Pro
385                 390                 395                 400
Trp Glu Glu Ile Lys Thr Ser Tyr Ala Gly Val Lys Glu Lys Tyr Leu
                405                 410                 415
Ser Glu Tyr Cys Phe Ser Gly Thr Tyr Ile Leu Ser Leu Leu Leu Gln
            420                 425                 430
Gly Tyr His Phe Thr Ala Asp Ser Trp Glu His Ile His Phe Ile Gly
        435                 440                 445
Lys Ile Gln Gly Ser Asp Ala Gly Trp Thr Leu Gly Tyr Met Leu Asn
    450                 455                 460
Leu Thr Asn Met Ile Pro Ala Glu Gln Pro Leu Ser Thr Pro Leu Ser
465                 470                 475                 480
His Ser Thr Tyr Val Phe Leu Met Val Leu Phe Ser Leu Val Leu Phe
                485                 490                 495
Thr Val Ala Ile Ile Gly Leu Leu Ile Phe His Lys Pro Ser Tyr Phe
```

```
            500                 505                 510
Trp Lys Asp Met Val
        515

<210> SEQ ID NO 55
<211> LENGTH: 1590
<212> TYPE: DNA
<213> ORGANISM: Homo sapiens

<400> SEQUENCE: 55
atggtcactg tgctgacccg ccaaccatgt gagcaagcag gcctcaaggc cctctaccga     60
actccaacca tcattgcctt ggtggtcttg cttgtgagta ttgtggtact tgtgagtatc    120
actgtcatcc agatccacaa gcaagaggtc ctccctccag gactgaagta tggtattgtg    180
ctggatgccg ggtcttcaag aaccacagtc tacgtgtatc aatggccagc agaaaaagag    240
aataataccg gagtggtcag tcaaaccttc aaatgtagtg tgaaaggctc tggaatctcc    300
agctatggaa ataaccccca agatgtcccc agagcctttg aggagtgtat gcaaaaagtc    360
aaggggcagg ttccatccca cctccacgga tccaccccca ttcacctggg agccacggct    420
gggatgcgct tgctgaggtt gcaaaatgaa acagcagcta atgaagtcct tgaaagcatc    480
caaagctact tcaagtccca gccctttgac tttaggggtg ctcaaatcat ttctgggcaa    540
gaagaagggg tatatggatg gattacagcc aactatttaa tgggaaattt cctggagaag    600
aacctgtggc acatgtgggt gcaccccgcat ggagtgaaaa ccacgggtgc cctggactta    660
ggtggtgcct ccacccaaat atccttcgtg caggagagaa agatggatct gaacaccagc    720
gacatcatgc aggtgtccct gtatggctac gtatacacgc tctacacaca cagcttccag    780
tgctatggcc ggaatgaggc tgagaagaag tttctggcaa tgctcctgca gaattctcct    840
accaaaaacc atctcaccaa tccctgttac cctcgggatt atagcatcag cttcaccatg    900
ggccatgtat ttgatagcct gtgcactgtg gaccagaggc agaaagtta taaccccaat    960 gatgtcatca cttttgaagg aactggggac ccatctctgt gtaaggagaa ggtggcttcc   1020
atatttgact tcaaagcttg ccatgatcaa gaaacctgtt cttttgatgg ggtttatcag   1080
ccaaagatta agggccatt tgtggctttt gcaggattct actacacagc cagtgcttta   1140
aatctttcag gtagcttttc cctggacacc ttcaactcca gcacctggaa tttctgctca   1200
cagaattgga gtcagctccc actgctgctc cccaaatttg atgaggtata tgcccgctct   1260
tactgcttct cagccaacta catctaccac ttgtttgtga acggttacaa attcacagag   1320
gagacttggc cccaaataca ctttgaaaaa gaagtgggga atagcagcat agcctggtct   1380
cttggctaca tgctcagcct gaccaaccag atcccagctg aaagccctct gatccgtctg   1440
cccatagaac cacctgtctt tgtgggcacc ctcgctttct tcacagcggc agccttgctg   1500
tgtctggcat tcttgcata cctgtgttca gcaaccagaa gaaagaggca ctccgagcat   1560 gccttttgacc atgcagtgga ttctgactga                                    1590

<210> SEQ ID NO 56
<211> LENGTH: 529
<212> TYPE: PRT
<213> ORGANISM: Homo sapiens

<400> SEQUENCE: 56

Met Val Thr Val Leu Thr Arg Gln Pro Cys Glu Gln Ala Gly Leu Lys
1               5                  10                  15

Ala Leu Tyr Arg Thr Pro Thr Ile Ile Ala Leu Val Val Leu Leu Val
```

```
                    20                  25                  30
Ser Ile Val Val Leu Val Ser Ile Thr Val Ile Gln Ile His Lys Gln
                35                  40                  45
Glu Val Leu Pro Pro Gly Leu Lys Tyr Gly Ile Val Leu Asp Ala Gly
            50                  55                  60
Ser Ser Arg Thr Thr Val Tyr Val Tyr Gln Trp Pro Ala Glu Lys Glu
65                  70                  75                  80
Asn Asn Thr Gly Val Val Ser Gln Thr Phe Lys Cys Ser Val Lys Gly
                85                  90                  95
Ser Gly Ile Ser Ser Tyr Gly Asn Asn Pro Gln Asp Val Pro Arg Ala
            100                 105                 110
Phe Glu Glu Cys Met Gln Lys Val Lys Gly Gln Val Pro Ser His Leu
        115                 120                 125
His Gly Ser Thr Pro Ile His Leu Gly Ala Thr Ala Gly Met Arg Leu
    130                 135                 140
Leu Arg Leu Gln Asn Glu Thr Ala Ala Asn Glu Val Leu Glu Ser Ile
145                 150                 155                 160
Gln Ser Tyr Phe Lys Ser Gln Pro Phe Asp Phe Arg Gly Ala Gln Ile
                165                 170                 175
Ile Ser Gly Gln Glu Glu Gly Val Tyr Gly Trp Ile Thr Ala Asn Tyr
            180                 185                 190
Leu Met Gly Asn Phe Leu Glu Lys Asn Leu Trp His Met Trp Val His
        195                 200                 205
Pro His Gly Val Glu Thr Thr Gly Ala Leu Asp Leu Gly Gly Ala Ser
    210                 215                 220
Thr Gln Ile Ser Phe Val Ala Gly Glu Lys Met Asp Leu Asn Thr Ser
225                 230                 235                 240
Asp Ile Met Gln Val Ser Leu Tyr Gly Tyr Val Tyr Thr Leu Tyr Thr
                245                 250                 255
His Ser Phe Gln Cys Tyr Gly Arg Asn Glu Ala Glu Lys Lys Phe Leu
            260                 265                 270
Ala Met Leu Leu Gln Asn Ser Pro Thr Lys Asn His Leu Thr Asn Pro
        275                 280                 285
Cys Tyr Pro Arg Asp Tyr Ser Ile Ser Phe Thr Met Gly His Val Phe
    290                 295                 300
Asp Ser Leu Cys Thr Val Asp Gln Arg Pro Glu Ser Tyr Asn Pro Asn
305                 310                 315                 320
Asp Val Ile Thr Phe Glu Gly Thr Gly Asp Pro Ser Leu Cys Lys Glu
                325                 330                 335
Lys Val Ala Ser Ile Phe Asp Phe Lys Ala Cys His Asp Gln Glu Thr
            340                 345                 350
Cys Ser Phe Asp Gly Val Tyr Gln Pro Lys Ile Lys Gly Pro Phe Val
        355                 360                 365
Ala Phe Ala Gly Phe Tyr Tyr Thr Ala Ser Ala Leu Asn Leu Ser Gly
    370                 375                 380
Ser Phe Ser Leu Asp Thr Phe Asn Ser Ser Thr Trp Asn Phe Cys Ser
385                 390                 395                 400
Gln Asn Trp Ser Gln Leu Pro Leu Leu Pro Lys Phe Asp Glu Val
                405                 410                 415
Tyr Ala Arg Ser Tyr Cys Phe Ser Ala Asn Tyr Ile Tyr His Leu Phe
            420                 425                 430
Val Asn Gly Tyr Lys Phe Thr Glu Glu Thr Trp Pro Gln Ile His Phe
        435                 440                 445
```

Glu Lys Glu Val Gly Asn Ser Ser Ile Ala Trp Ser Leu Gly Tyr Met
    450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Ala
                485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
        515                 520                 525

Asp

<210> SEQ ID NO 57
<211> LENGTH: 1326
<212> TYPE: DNA
<213> ORGANISM: Homo sapiens

<400> SEQUENCE: 57

| | | |
|---|---|---|
| atgcagaaca aagcattgcc agaaaacgtt aagtatggga ttgtgctgga tgcgggttct | 60 |
| tctcacacaa gtttatacat ctataagtgg ccagcagaaa aggagaatga cacaggcgtg | 120 |
| gtgcatcaag tagaagaatg cagggttaaa ggtcctggaa tctcaaaatt tgttcagaaa | 180 |
| gtaaatgaaa taggcattta cctgactgat tgcatggaaa gagctaggga agtgattcca | 240 |
| aggtcccagc accaagagac acccgtttac ctgggagcca cggcaggcat gcggttgctc | 300 |
| aggatggaaa gtgaagagtt ggcagacagg gttctggatg tggtggagag gagcctcagc | 360 |
| aactacccct ttgacttcca gggtgccagg atcattactg ccaagagga aggtgcctat | 420 |
| ggctggatta ctatcaacta tctgctgggc aaattcagtc agaaaacaag gtggttcagc | 480 |
| atagtcccat atgaaaccaa taatcaggaa acctttggag ctttggacct tgggggagcc | 540 |
| tctacacaag tcacttttgt accccaaaac cagactatcg agtccccaga taatgctctg | 600 |
| caatttcgcc tctatggcaa ggactacaat gtctacacac atagcttctt gtgctatggg | 660 |
| aaggatcagg cactctggca gaaactggcc aaggacattc aggttgcaag taatgaaatt | 720 |
| ctcagggacc catgctttca tcctggatat aagaaggtag tgaacgtaag tgacctttac | 780 |
| aagacccct gcaccaagag atttgagatg actcttccat tccagcagtt tgaaatccag | 840 |
| ggtattggaa actatcaaca atgccatcaa agcatcctgg agctcttcaa caccagttac | 900 |
| tgcccttact cccagtgtgc cttcaatggg attttcttgc caccactcca ggggattt | 960 |
| ggggcatttt cagctttta ctttgtgatg aagtttttaa acttgacatc agagaaagtc | 1020 |
| tctcaggaaa aggtgactga gatgatgaaa agttctgtg ctcagccttg ggaggagata | 1080 |
| aaaacatctt acgctggagt aaaggagaag tacctgagtg aatactgctt ttctggtacc | 1140 |
| tacattctct ccctccttct gcaaggctat catttcacag ctgattcctg ggagcacatc | 1200 |
| catttcattg gcaagatcca gggcagcgac gccggctgga ctttgggcta catgctgaac | 1260 |
| ctgaccaaca tgatcccagc tgagcaacca ttgtccacac ctctctccca ctccacctat | 1320 |
| tagtga | 1326 |

<210> SEQ ID NO 58
<211> LENGTH: 440
<212> TYPE: PRT
<213> ORGANISM: Homo sapiens

<400> SEQUENCE: 58

```
Met Gln Asn Lys Ala Leu Pro Glu Asn Val Lys Tyr Gly Ile Val Leu
 1               5                  10                  15

Asp Ala Gly Ser Ser His Thr Ser Leu Tyr Ile Tyr Lys Trp Pro Ala
                20                  25                  30

Glu Lys Glu Asn Asp Thr Gly Val Val His Gln Val Glu Glu Cys Arg
            35                  40                  45

Val Lys Gly Pro Gly Ile Ser Lys Phe Val Gln Lys Val Asn Glu Ile
 50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Glu Gly Ala Tyr Gly Trp Ile Thr
130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
            195                 200                 205

Tyr Asn Val Tyr Thr His Ser Phe Leu Cys Tyr Gly Lys Asp Gln Ala
 210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
                260                 265                 270

Pro Phe Gln Gln Phe Glu Ile Gln Gly Ile Gly Asn Tyr Gln Gln Cys
            275                 280                 285

His Gln Ser Ile Leu Glu Leu Phe Asn Thr Ser Tyr Cys Pro Tyr Ser
            290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
            355                 360                 365

Glu Lys Tyr Leu Ser Glu Tyr Cys Phe Ser Gly Thr Tyr Ile Leu Ser
 370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415
```

```
Tyr Met Leu Asn Leu Thr Asn Met Ile Pro Ala Glu Gln Pro Leu Ser
            420                 425                 430

Thr Pro Leu Ser His Ser Thr Tyr
            435                 440

<210> SEQ ID NO 59
<211> LENGTH: 1335
<212> TYPE: DNA
<213> ORGANISM: Homo sapiens

<400> SEQUENCE: 59
atgcagatcc acaagcaaga ggtcctccct ccaggactga gtatggtat tgtgctggat    60 gccgggtctt caagaaccac agtctacgtg tatcaatggc cagcagaaaa agagaataat   120
accggagtgg tcagtcaaac cttcaaatgt agtgtgaaag ctctggaat ctccagctat   180 ggaaataacc cccaagatgt ccccagagcc tttgaggagt gtatgcaaaa agtcaagggg   240
caggttccat cccacctcca cggatccacc cccattcacc tgggagccac ggctgggatg   300
cgcttgctga ggttgcaaaa tgaaacagca gctaatgaag tccttgaaag catccaaagc   360
tacttcaagt cccagccctt tgactttagg ggtgctcaaa tcatttctgg caagaagaa   420 ggggtatatg gatggattac agccaactat ttaatgggaa atttcctgga agaacctg    480 tggcacatgt gggtgcaccc gcatggagtg gaaaccacgg tgccctgga cttaggtggt   540 gcctccaccc aaatatcctt cgtggcagga gagaagatgg atctgaacac cagcgacatc   600
atgcaggtgt ccctgtatgg ctacgtatac acgctctaca cacacagctt ccagtgctat   660
ggccggaatg aggctgagaa gaagtttctg gcaatgctcc tgcagaattc tcctaccaaa   720
aaccatctca ccaatccctg ttaccctcgg gattatagca tcagcttcac catgggccat   780
gtatttgata gcctgtgcac tgtggaccag aggccagaaa gttataaccc caatgatgtc   840
atcacttttg aaggaactgg ggaccccatct ctgtgtaagg agaaggtggc ttccatattt   900
gacttcaaag cttgccatga tcaagaaacc tgttcttttg atggggttta tcagccaaag   960
attaaagggc catttgtggc ttttgcagga ttctactaca cagccagtgc tttaaatctt  1020
tcaggtagct tttccctgga caccttcaac tccagcacct ggaatttctg ctcacagaat  1080
tggagtcagc tcccactgct gctccccaaa tttgatgagg tatatgcccg ctcttactgc  1140
ttctcagcca actacatcta ccacttgttt gtgaacggtt acaaattcac agaggagact  1200 tggcccccaaa tacactttga aaaagaagtg gggaatagca gcatagcctg gtctcttggc  1260
tacatgctca gcctgaccaa ccagatccca gctgaaagcc tctgatccg tctgcccata  1320 gaaccacctg tctga                                                    1335

<210> SEQ ID NO 60
<211> LENGTH: 444
<212> TYPE: PRT
<213> ORGANISM: Homo sapiens

<400> SEQUENCE: 60

Met Gln Ile His Lys Gln Glu Val Leu Pro Gly Leu Lys Tyr Gly
  1               5                  10                  15

Ile Val Leu Asp Ala Gly Ser Ser Arg Thr Thr Val Tyr Val Tyr Gln
                 20                  25                  30

Trp Pro Ala Glu Lys Glu Asn Asn Thr Gly Val Val Ser Gln Thr Phe
             35                  40                  45

Lys Cys Ser Val Lys Gly Ser Gly Ile Ser Ser Tyr Gly Asn Asn Pro
         50                  55                  60
```

```
Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Glu Gly Val Tyr Gly
130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
        275                 280                 285

Pro Ser Leu Cys Lys Glu Lys Val Ala Ser Ile Phe Asp Phe Lys Ala
290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
        355                 360                 365

Pro Lys Phe Asp Glu Val Tyr Ala Arg Ser Tyr Cys Phe Ser Ala Asn
370                 375                 380

Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
                405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Pro Val
        435                 440

<210> SEQ ID NO 61
<211> LENGTH: 1323
<212> TYPE: DNA
<213> ORGANISM: Homo sapiens
```

<400> SEQUENCE: 61

```
atgcagaaca aagcattgcc agaaaacgtt aagtatggga ttgtgctgga tgcgggttct      60
tctgggacaa gtttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcattta cctgactgat tgcatggaaa gagctaggga agtgattcca     240
aggtcccagc accaagagac acccgtttac ctgggagcca cggcaggcat gcggttgctc     300
aggatggaaa gtgaagagtt ggcagacagg gttctggatg tggtggagag gagcctcagc     360
aactacccct tgacttcca gggtgccagg atcattactg ccaagagga aggtgcctat       420
ggctggatta ctatcaacta tctgctgggc aaattcagtc agaaaacaag gtggttcagc     480
atagtcccat atgaaaccaa taatcaggaa acctttggag ctttggacct tggggagcc     540
tctacacaag tcacttttgt accccaaaac cagactatcg agtccccaga taatgctctg     600
caatttcgcc tctatggcaa ggactacaat gtctacacac atagcttctt gtgctatggg     660
aaggatcagg cactctggca gaaactggcc aaggacattc aggttgcaag taatgaaatt     720
ctcagggacc catgctttca tcctggatat aagaaggtag tgaacgtaag tgaccttac     780
aagaccccct gcaccaagag atttgagatg actcttccat tccagcagtt tgaaatccag     840
ggtattggaa actatcaaca atgccatcaa agcatcctgg agctcttcaa caccagttac     900
tgcccttact cccagtgtgc cttcaatggg attttcttgc caccactcca ggggattt      960
gggggcatttt cagctttta ctttgtgatg aagttttaa acttgacatc agagaaagtc    1020
tctcaggaaa aggtgactga gatgatgaaa aagttctgtg ctcagccttg ggaggagata   1080
aaaacatctt acgctggagt aaaggagaag tacctgagtg aatactgctt ttctggtacc   1140
tacattctct ccctccttct gcaaggctat catttcacag ctgattcctg ggagcacatc   1200
catttcattg gcaagatcca gggcagcgac gccggctgga ctttgggcta catgctgaac   1260
ctgaccaaca tgatcccagc tgagcaacca ttgtccacac ctctctccca ctccacctat   1320
tag                                                                  1323
```

<210> SEQ ID NO 62
<211> LENGTH: 440
<212> TYPE: PRT
<213> ORGANISM: Homo sapiens

<400> SEQUENCE: 62

```
Met Gln Asn Lys Ala Leu Pro Glu Asn Val Lys Tyr Gly Ile Val Leu
  1               5                  10                  15

Asp Ala Gly Ser Ser Gly Thr Ser Leu Tyr Ile Tyr Lys Trp Pro Ala
             20                  25                  30

Glu Lys Glu Asn Asp Thr Gly Val Val His Gln Val Glu Glu Cys Arg
         35                  40                  45

Val Lys Gly Pro Gly Ile Ser Lys Phe Val Gln Lys Val Asn Glu Ile
     50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
             85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125
```

```
Ala Arg Ile Ile Thr Gly Gln Glu Gly Ala Tyr Gly Trp Ile Thr
        130                 135                 140
Ile Asn Tyr Leu Leu Gly Lys Phe Ser Gln Lys Thr Arg Trp Phe Ser
145                 150                 155                 160
Ile Val Pro Tyr Glu Thr Asn Asn Gln Glu Thr Phe Gly Ala Leu Asp
                165                 170                 175
Leu Gly Gly Ala Ser Thr Gln Val Thr Phe Val Pro Asn Gln Thr
        180                 185                 190
Ile Glu Ser Pro Asp Asn Ala Leu Gln Phe Arg Leu Tyr Gly Lys Asp
            195                 200                 205
Tyr Asn Val Tyr Thr His Ser Phe Leu Cys Tyr Gly Lys Asp Gln Ala
        210                 215                 220
Leu Trp Gln Lys Leu Ala Lys Asp Ile Gln Val Ala Ser Asn Glu Ile
225                 230                 235                 240
Leu Arg Asp Pro Cys Phe His Pro Gly Tyr Lys Lys Val Val Asn Val
                245                 250                 255
Ser Asp Leu Tyr Lys Thr Pro Cys Thr Lys Arg Phe Glu Met Thr Leu
            260                 265                 270
Pro Phe Gln Gln Phe Glu Ile Gln Gly Ile Gly Asn Tyr Gln Gln Cys
        275                 280                 285
His Gln Ser Ile Leu Glu Leu Phe Asn Thr Ser Tyr Cys Pro Tyr Ser
        290                 295                 300
Gln Cys Ala Phe Asn Gly Ile Phe Leu Pro Pro Leu Gln Gly Asp Phe
305                 310                 315                 320
Gly Ala Phe Ser Ala Phe Tyr Phe Val Met Lys Phe Leu Asn Leu Thr
                325                 330                 335
Ser Glu Lys Val Ser Gln Glu Lys Val Thr Glu Met Met Lys Lys Phe
            340                 345                 350
Cys Ala Gln Pro Trp Glu Glu Ile Lys Thr Ser Tyr Ala Gly Val Lys
        355                 360                 365
Glu Lys Tyr Leu Ser Glu Tyr Cys Phe Ser Gly Thr Tyr Ile Leu Ser
        370                 375                 380
Leu Leu Leu Gln Gly Tyr His Phe Thr Ala Asp Ser Trp Glu His Ile
385                 390                 395                 400
His Phe Ile Gly Lys Ile Gln Gly Ser Asp Ala Gly Trp Thr Leu Gly
                405                 410                 415
Tyr Met Leu Asn Leu Thr Asn Met Ile Pro Ala Glu Gln Pro Leu Ser
            420                 425                 430
Thr Pro Leu Ser His Ser Thr Tyr
        435                 440

<210> SEQ ID NO 63
<211> LENGTH: 1323
<212> TYPE: DNA
<213> ORGANISM: Homo sapiens

<400> SEQUENCE: 63
atgcagaaca aagcattgcc agaaaacgtt aagtatggga ttgtgctgga tgcgggttct      60
tctgcgacaa gtttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcatttta cctgactgat tgcatggaaa gagctaggga agtgattcca     240
aggtcccagc accaagagac acccgtttac ctgggagcca cggcaggcat gcggttgctc     300
```

-continued

```
aggatggaaa gtgaagagtt ggcagacagg gttctggatg tggtggagag gagcctcagc      360
aactacccct ttgacttcca gggtgccagg atcattactg ccaagagga aggtgcctat      420
ggctggatta ctatcaacta tctgctgggc aaattcagtc agaaaacaag gtggttcagc      480
atagtcccat atgaaaccaa taatcaggaa acctttggag ctttggacct tgggggagcc      540
tctacacaag tcactttgt accccaaaac cagactatcg agtccccaga taatgctctg      600
caatttcgcc tctatggcaa ggactacaat gtctacacac atagcttctt gtgctatggg      660
aaggatcagg cactctggca gaaactggcc aaggacattc aggttgcaag taatgaaatt      720
ctcagggacc catgctttca tcctggatat aagaaggtag tgaacgtaag tgaccttac      780
aagaccccct gcaccaagag atttgagatg actcttccat ccagcagtt tgaaatccag      840
ggtattggaa actatcaaca atgccatcaa agcatcctgg agctcttcaa caccagttac      900
tgcccttact cccagtgtgc cttcaatggg attttcttgc caccactcca ggggatttt      960
ggggcatttt cagcttttta ctttgtgatg aagtttttaa acttgacatc agagaaagtc     1020
tctcaggaaa aggtgactga gatgatgaaa aagttctgtg ctcagccttg ggaggagata     1080
aaaacatctt acgctggagt aaaggagaag tacctgagtg aatactgctt ttctggtacc     1140
tacattctct ccctccttct gcaaggctat catttcacag ctgattcctg ggagcacatc     1200
catttcattg gcaagatcca gggcagcgac gccggctgga ctttgggcta catgctgaac     1260
ctgaccaaca tgatcccagc tgagcaacca ttgtccacac ctctctccca ctccacctat     1320
tag                                                                  1323
```

<210> SEQ ID NO 64
<211> LENGTH: 440
<212> TYPE: PRT
<213> ORGANISM: Homo sapiens

<400> SEQUENCE: 64

```
Met Gln Asn Lys Ala Leu Pro Glu Asn Val Lys Tyr Gly Ile Val Leu
  1               5                  10                  15

Asp Ala Gly Ser Ser Ala Thr Ser Leu Tyr Ile Tyr Lys Trp Pro Ala
             20                  25                  30

Glu Lys Glu Asn Asp Thr Gly Val Val His Gln Val Glu Glu Cys Arg
         35                  40                  45

Val Lys Gly Pro Gly Ile Ser Lys Phe Val Gln Lys Val Asn Glu Ile
     50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190
```

Ile Glu Ser Pro Asp Asn Ala Leu Gln Phe Arg Leu Tyr Gly Lys Asp
         195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr Tyr
        435                 440

<210> SEQ ID NO 65
<211> LENGTH: 1323
<212> TYPE: DNA
<213> ORGANISM: Homo sapiens

<400> SEQUENCE: 65
atgcagaaca aagcattgcc agaaaacgtt aagtatggga ttgtgctgga tgcgggttct      60
tctgggacac gcttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcattta cctgactgat tgcatggaaa gagctaggga agtgattcca     240
aggtcccagc accaagagac acccgtttac ctgggagcca cggcaggcat gcggttgctc     300
aggatggaaa gtgaagagtt ggcagacagg gttctggatg tggtggagag gagcctcagc     360
aactacccct ttgacttcca gggtgccagg atcattactg ccaagagga aggtgcctat     420
ggctggatta ctatcaacta tctgctgggc aaattcagtc agaaaacaag gtggttcagc     480
atagtcccat atgaaaccaa taatcaggaa acctttggag ctttggacct tggggagcc     540
tctacacaag tcacttttgt accccaaaac cagactatcg agtccccaga taatgctctg     600
caatttcgcc tctatggcaa ggactacaat gtctacacac atagcttctt gtgctatggg     660

```
aaggatcagg cactctggca gaaactggcc aaggacattc aggttgcaag taatgaaatt    720
ctcagggacc catgctttca tcctggatat aagaaggtag tgaacgtaag tgacctttac    780
aagacccctt gcaccaagag atttgagatg actcttccat ccagcagtt tgaaatccag     840 ggtattggaa actatcaaca atgccatcaa agcatcctgg agctcttcaa caccagttac    900
tgcccttact cccagtgtgc cttcaatggg attttcttgc caccactcca gggggatttt    960
ggggcatttt cagcttttta ctttgtgatg aagttttaa acttgacatc agagaaagtc    1020
tctcaggaaa aggtgactga gatgatgaaa aagttctgtg ctcagccttg ggaggagata   1080
aaaacatctt acgctggagt aaaggagaag tacctgagtg aatactgctt ttctggtacc    1140
tacattctct ccctccttct gcaaggctat catttcacag ctgattcctg ggagcacatc    1200
catttcattg gcaagatcca gggcagcgac gccggctgga ctttgggcta catgctgaac    1260
ctgaccaaca tgatcccagc tgagcaacca ttgtccacac ctctctccca ctccacctat    1320
tag                                                                  1323
```

<210> SEQ ID NO 66
<211> LENGTH: 440
<212> TYPE: PRT
<213> ORGANISM: Homo sapiens

<400> SEQUENCE: 66

```
Met Gln Asn Lys Ala Leu Pro Glu Asn Val Lys Tyr Gly Ile Val Leu
 1               5                  10                  15

Asp Ala Gly Ser Ser Gly Thr Arg Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255
```

Ser Asp Leu Tyr Lys Thr Pro Cys Thr Lys Arg Phe Glu Met Thr Leu
          260                 265                 270

Pro Phe Gln Gln Phe Glu Ile Gln Gly Ile Gly Asn Tyr Gln Gln Cys
          275                 280                 285

His Gln Ser Ile Leu Glu Leu Phe Asn Thr Ser Tyr Cys Pro Tyr Ser
          290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
              325                 330                 335

Ser Glu Lys Val Ser Gln Glu Lys Val Thr Glu Met Met Lys Lys Phe
          340                 345                 350

Cys Ala Gln Pro Trp Glu Glu Ile Lys Thr Ser Tyr Ala Gly Val Lys
          355                 360                 365

Glu Lys Tyr Leu Ser Glu Tyr Cys Phe Ser Gly Thr Tyr Ile Leu Ser
          370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
              405                 410                 415

Tyr Met Leu Asn Leu Thr Asn Met Ile Pro Ala Glu Gln Pro Leu Ser
          420                 425                 430

Thr Pro Leu Ser His Ser Thr Tyr
          435                 440

<210> SEQ ID NO 67
<211> LENGTH: 1323
<212> TYPE: DNA
<213> ORGANISM: Homo sapiens

<400> SEQUENCE: 67

```
atgcagaaca aagcattgcc agaaaacgtt aagtatggga ttgtgctgga tgcgggttct      60
tctgcgacac gcttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcattta cctgactgat tgcatggaaa gagctaggga agtgattcca     240
aggtcccagc accaagagac acccgtttac ctgggagcca cggcaggcat gcggttgctc     300
aggatggaaa gtgaagagtt ggcagacagg gttctggatg tggtggagag gagcctcagc     360
aactacccct ttgacttcca gggtgccagg atcattactg ccaagaggaa ggtgcctat      420
ggctggatta ctatcaacta tctgctgggc aaattcagtc agaaaacaag gtggttcagc     480
atagtcccat atgaaaccaa taatcaggaa acctttggag ctttggacct tggggagcc      540
tctacacaag tcactttgt accccaaaac cagactatcg agtccccaga taatgctctg     600
caatttcgcc tctatggcaa ggactacaat gtctacacac atagcttctt gtgctatggg     660
aaggatcagg cactctggca gaaactggcc aaggacattc aggttgcaag taatgaaatt     720
ctcagggacc catgctttca tcctggatat aagaaggtag tgaacgtaag tgacctttac     780
aagaccccct gcaccaagag atttgagatg actcttccat tccagcagtt tgaaatccag     840
ggtattggaa actatcaaca atgccatcaa agcatcctgg agctcttcaa caccagttac     900
tgcccttact cccagtgtgc cttcaatggg attttcttgc caccactcca ggggattt      960
gggcatttt cagctttta ctttgtgatg aagttttaa acttgacatc agagaaagtc      1020
```

```
tctcaggaaa aggtgactga gatgatgaaa aagttctgtg ctcagccttg ggaggagata   1080
aaaacatctt acgctggagt aaaggagaag tacctgagtg aatactgctt ttctggtacc   1140
tacattctct ccctccttct gcaaggctat catttcacag ctgattcctg ggagcacatc   1200
catttcattg gcaagatcca gggcagcgac gccggctgga ctttgggcta catgctgaac   1260
ctgaccaaca tgatcccagc tgagcaacca ttgtccacac ctctctccca ctccacctat   1320
tag                                                                1323
```

<210> SEQ ID NO 68
<211> LENGTH: 440
<212> TYPE: PRT
<213> ORGANISM: Homo sapiens

<400> SEQUENCE: 68

```
Met Gln Asn Lys Ala Leu Pro Glu Asn Val Lys Tyr Gly Ile Val Leu
 1               5                  10                  15

Asp Ala Gly Ser Ser Ala Thr Arg Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
           100                 105                 110

Asp Val Val Glu Arg Ser Leu Ser Asn Tyr Pro Phe Asp Phe Gln Gly
       115                 120                 125

Ala Arg Ile Ile Thr Gly Gln Glu Glu Gly Ala Tyr Gly Trp Ile Thr
   130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
               165                 170                 175

Leu Gly Gly Ala Ser Thr Gln Val Thr Phe Val Pro Gln Asn Gln Thr
           180                 185                 190

Ile Glu Ser Pro Asp Asn Ala Leu Gln Phe Arg Leu Tyr Gly Lys Asp
       195                 200                 205

Tyr Asn Val Tyr Thr His Ser Phe Leu Cys Tyr Gly Lys Asp Gln Ala
   210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
               245                 250                 255

Ser Asp Leu Tyr Lys Thr Pro Cys Thr Lys Arg Phe Glu Met Thr Leu
           260                 265                 270

Pro Phe Gln Gln Phe Glu Ile Gln Gly Ile Gly Asn Tyr Gln Gln Cys
       275                 280                 285

His Gln Ser Ile Leu Glu Leu Phe Asn Thr Ser Tyr Cys Pro Tyr Ser
   290                 295                 300

Gln Cys Ala Phe Asn Gly Ile Phe Leu Pro Pro Leu Gln Gly Asp Phe
305                 310                 315                 320
```

Gly Ala Phe Ser Ala Phe Tyr Phe Val Met Lys Phe Leu Asn Leu Thr
            325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
            355                 360                 365

Glu Lys Tyr Leu Ser Glu Tyr Cys Phe Ser Gly Thr Tyr Ile Leu Ser
            370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr Tyr
            435                 440

<210> SEQ ID NO 69
<211> LENGTH: 1335
<212> TYPE: DNA
<213> ORGANISM: Homo sapiens

<400> SEQUENCE: 69

| | | | | |
|---|---|---|---|---|
| atgcagatcc | acaagcaaga | ggtcctccct | ccaggactga | agtatggtat tgtgctggat | 60 |
| gccgggtctt | cagcgaccac | agtctacgtg | tatcaatggc | agcagaaaaa agagaataat | 120 |
| accggagtgg | tcagtcaaac | cttcaaatgt | agtgtgaaag | gctctggaat ctccagctat | 180 |
| ggaaataacc | cccaagatgt | ccccagagcc | tttgaggagt | gtatgcaaaa agtcaagggg | 240 |
| caggttccat | cccacctcca | cggatccacc | ccattcacc | tgggagccac ggctgggatg | 300 |
| cgcttgctga | ggttgcaaaa | tgaaacagca | gctaatgaag | tccttgaaag catccaaagc | 360 |
| tacttcaagt | cccagccctt | tgactttagg | ggtgctcaaa | tcatttctgg caagaagaa | 420 |
| ggggtatatg | gatggattac | agccaactat | ttaatggaa | atttcctgga gaagaacctg | 480 |
| tggcacatgt | gggtgcaccc | gcatggagtg | aaaccacgg | gtgccctgga cttaggtggt | 540 |
| gcctccaccc | aaatatcctt | cgtggcagga | gagaagatgg | atctgaacac cagcgacatc | 600 |
| atgcaggtgt | ccctgtatgg | ctacgtatac | acgctctaca | cacacagctt ccagtgctat | 660 |
| ggccggaatg | aggctgagaa | gaagtttctg | gcaatgctcc | tgcagaattc tcctaccaaa | 720 |
| aaccatctca | ccaatccctg | ttaccctcgg | gattatagca | tcagcttcac catgggccat | 780 |
| gtatttgata | gcctgtgcac | tgtggaccag | aggccagaaa | gttataaccc caatgatgtc | 840 |
| atcactttg | aaggaactgg | ggacccatct | ctgtgtaagg | agaaggtggc ttccatattt | 900 |
| gacttcaaag | cttgccatga | tcaagaaacc | tgttcttttg | atggggttta tcagccaaag | 960 |
| attaaagggc | atttgtggc | ttttgcagga | ttctactaca | cagccagtgc tttaaatctt | 1020 |
| tcaggtagct | tttccctgga | caccttcaac | tccagcacct | ggaatttctg ctcacagaat | 1080 |
| tggagtcagc | tcccactgct | gctccccaaa | tttgatgagg | tatatgcccg ctcttactgc | 1140 |
| ttctcagcca | actacatcta | ccacttgttt | gtgaacggtt | acaaattcac agaggagact | 1200 |
| tggccccaaa | tacactttga | aaaagaagtg | gggaatagca | gcatagcctg gtctcttggc | 1260 |
| tacatgctca | gcctgaccaa | ccagatccca | gctgaaagcc | ctctgatccg tctgcccata | 1320 |
| gaaccacctg | tctga | | | | 1335 |

<210> SEQ ID NO 70
<211> LENGTH: 444
<212> TYPE: PRT
<213> ORGANISM: Homo sapiens

<400> SEQUENCE: 70

```
Met Gln Ile His Lys Gln Glu Val Leu Pro Gly Leu Lys Tyr Gly
  1               5                  10                  15

Ile Val Leu Asp Ala Gly Ser Ser Ala Thr Thr Val Tyr Val Tyr Gln
                 20                  25                  30

Trp Pro Ala Glu Lys Glu Asn Asn Thr Gly Val Val Ser Gln Thr Phe
             35                  40                  45

Lys Cys Ser Val Lys Gly Ser Gly Ile Ser Ser Tyr Gly Asn Asn Pro
 50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
            115                 120                 125

Phe Arg Gly Ala Gln Ile Ile Ser Gly Gln Glu Glu Gly Val Tyr Gly
130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
    210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
        275                 280                 285

Pro Ser Leu Cys Lys Glu Lys Val Ala Ser Ile Phe Asp Phe Lys Ala
    290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
        355                 360                 365

Pro Lys Phe Asp Glu Val Tyr Ala Arg Ser Tyr Cys Phe Ser Ala Asn
    370                 375                 380
```

Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
            405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Pro Val
            435                 440

<210> SEQ ID NO 71
<211> LENGTH: 1335
<212> TYPE: DNA
<213> ORGANISM: Homo sapiens

<400> SEQUENCE: 71

```
atgcagatcc acaagcaaga ggtcctccct ccaggactga agtatggtat tgtgctggat      60
gccgggtctt cagggaccac agtctacgtg tatcaatggc agcagaaaaa agagaataat     120
accggagtgg tcagtcaaac cttcaaatgt agtgtgaaag ctctggaat  ctccagctat     180
ggaaataacc cccaagatgt ccccagagcc tttgaggagt gtatgcaaaa agtcaagggg     240
caggttccat cccacctcca cggatccacc cccattcacc tgggagccac ggctgggatg     300
cgcttgctga ggttgcaaaa tgaaacagca gctaatgaag tccttgaaag catccaaagc     360
tacttcaagt cccagccctt tgactttagg ggtgctcaaa tcatttctgg caagaagaa      420
ggggtatatg gatggattac agccaactat ttaatgggaa atttcctgga gaagaacctg     480
tggcacatgt gggtgcaccc gcatggagtg gaaaccacgg gtgccctgga cttaggtggt     540
gcctccaccc aaatatcctt cgtggcagga gagaagatga tctgaacac  cagcgacatc     600
atgcaggtgt ccctgtatgg ctacgtatac acgctctaca cacacagctt ccagtgctat     660
ggccggaatg aggctgagaa gaagtttctg caatgctcc  tgcagaattc tcctaccaaa     720
aaccatctca ccaatccctg ttaccctcgg gattatagca tcagcttcac catgggccat     780
gtatttgata gcctgtgcac tgtggaccag aggccagaaa gttataaccc caatgatgtc     840
atcacttttg aaggaactgg ggacccatct ctgtgtaagg agaaggtggc ttccatattt     900
gacttcaaag cttgccatga tcaagaaacc tgttctttg  atggggttta tcagccaaag     960
attaaagggc catttgtggc ttttgcagga ttctactaca cagccagtgc tttaaatctt    1020
tcaggtagct tttccctgga cacctcaac  tccagcacct ggaatttctg ctcacagaat    1080
tggagtcagc tcccactgct gctccccaaa tttgatgagg tatatgcccg ctcttactgc    1140
ttctcagcca actacatcta ccacttgttt gtgaacggtt acaaattcac agaggagact    1200
tggccccaaa tacactttga aaagaagtg  gggaatagca gcatagcctg gtctcttggc    1260
tacatgctca gcctgaccaa ccagatccca gctgaaagcc ctctgatccg tctgcccata    1320
gaaccacctg tctga                                                     1335
```

<210> SEQ ID NO 72
<211> LENGTH: 444
<212> TYPE: PRT
<213> ORGANISM: Homo sapiens

<400> SEQUENCE: 72

Met Gln Ile His Lys Gln Glu Val Leu Pro Pro Gly Leu Lys Tyr Gly
1               5                   10                  15

Ile Val Leu Asp Ala Gly Ser Ser Gly Thr Thr Val Tyr Val Tyr Gln

-continued

```
                    20                  25                  30
Trp Pro Ala Glu Lys Glu Asn Asn Thr Gly Val Val Ser Gln Thr Phe
            35                  40                  45
Lys Cys Ser Val Lys Gly Ser Gly Ile Ser Ser Tyr Gly Asn Asn Pro
    50                  55                  60
Gln Asp Val Pro Arg Ala Phe Glu Glu Cys Met Gln Lys Val Lys Gly
65                  70                  75                  80
Gln Val Pro Ser His Leu His Gly Ser Thr Pro Ile His Leu Gly Ala
                85                  90                  95
Thr Ala Gly Met Arg Leu Leu Arg Leu Gln Asn Glu Thr Ala Ala Asn
            100                 105                 110
Glu Val Leu Glu Ser Ile Gln Ser Tyr Phe Lys Ser Gln Pro Phe Asp
        115                 120                 125
Phe Arg Gly Ala Gln Ile Ile Ser Gly Gln Glu Glu Gly Val Tyr Gly
    130                 135                 140
Trp Ile Thr Ala Asn Tyr Leu Met Gly Asn Phe Leu Glu Lys Asn Leu
145                 150                 155                 160
Trp His Met Trp Val His Pro His Gly Val Glu Thr Thr Gly Ala Leu
                165                 170                 175
Asp Leu Gly Gly Ala Ser Thr Gln Ile Ser Phe Val Ala Gly Glu Lys
            180                 185                 190
Met Asp Leu Asn Thr Ser Asp Ile Met Gln Val Ser Leu Tyr Gly Tyr
        195                 200                 205
Val Tyr Thr Leu Tyr Thr His Ser Phe Gln Cys Tyr Gly Arg Asn Glu
    210                 215                 220
Ala Glu Lys Lys Phe Leu Ala Met Leu Leu Gln Asn Ser Pro Thr Lys
225                 230                 235                 240
Asn His Leu Thr Asn Pro Cys Tyr Pro Arg Asp Tyr Ser Ile Ser Phe
                245                 250                 255
Thr Met Gly His Val Phe Asp Ser Leu Cys Thr Val Asp Gln Arg Pro
            260                 265                 270
Glu Ser Tyr Asn Pro Asn Asp Val Ile Thr Phe Glu Gly Thr Gly Asp
        275                 280                 285
Pro Ser Leu Cys Lys Glu Lys Val Ala Ser Ile Phe Asp Phe Lys Ala
    290                 295                 300
Cys His Asp Gln Glu Thr Cys Ser Phe Asp Gly Val Tyr Gln Pro Lys
305                 310                 315                 320
Ile Lys Gly Pro Phe Val Ala Phe Ala Gly Phe Tyr Tyr Thr Ala Ser
                325                 330                 335
Ala Leu Asn Leu Ser Gly Ser Phe Ser Leu Asp Thr Phe Asn Ser Ser
            340                 345                 350
Thr Trp Asn Phe Cys Ser Gln Asn Trp Ser Gln Leu Pro Leu Leu Leu
        355                 360                 365
Pro Lys Phe Asp Glu Val Tyr Ala Arg Ser Tyr Cys Phe Ser Ala Asn
    370                 375                 380
Tyr Ile Tyr His Leu Phe Val Asn Gly Tyr Lys Phe Thr Glu Glu Thr
385                 390                 395                 400
Trp Pro Gln Ile His Phe Glu Lys Glu Val Gly Asn Ser Ser Ile Ala
                405                 410                 415
Trp Ser Leu Gly Tyr Met Leu Ser Leu Thr Asn Gln Ile Pro Ala Glu
            420                 425                 430
Ser Pro Leu Ile Arg Leu Pro Ile Glu Pro Pro Val
        435                 440
```

<210> SEQ ID NO 73
<211> LENGTH: 1335
<212> TYPE: DNA
<213> ORGANISM: Homo sapiens

<400> SEQUENCE: 73

```
atgcagatcc acaagcaaga ggtcctccct ccaggactga agtatggtat tgtgctggat      60
gccgggtctt cagcgacccg cgtctacgtg tatcaatggc cagcagaaaa agagaataat     120
accggagtgg tcagtcaaac cttcaaatgt agtgtgaaag ctctggaat ctccagctat      180
ggaaataacc cccaagatgt ccccagagcc tttgaggagt gtatgcaaaa agtcaagggg     240
caggttccat cccacctcca cggatccacc cccattcacc tgggagccac ggctgggatg     300
cgcttgctga ggttgcaaaa tgaaacagca gctaatgaag tccttgaaag catccaaagc     360
tacttcaagt cccagccctt tgactttagg ggtgctcaaa tcatttctgg caagaagaa     420
ggggtatatg gatggattac agccaactat ttaatgggaa atttcctgga gaagaacctg     480
tggcacatgt gggtgcaccc gcatggagtg gaaaccacgg tgccctgga cttaggtggt     540
gcctccaccc aaatatcctt cgtggcagga gagaagatgg atctgaacac cagcgacatc     600
atgcaggtgt ccctgtatgg ctacgtatac acgctctaca cacacagctt ccagtgctat     660
ggccggaatg aggctgagaa gaagtttctg caatgctcc tgcagaattc tcctaccaaa     720
aaccatctca ccaatccctg ttaccctcgg gattatagca tcagcttcac catgggccat     780
gtatttgata gcctgtgcac tgtggaccag aggccagaaa gttataaccc caatgatgtc     840
atcacttttg aaggaactgg ggacccatct ctgtgtaagg agaaggtggc ttccatattt     900
gacttcaaag cttgccatga tcaagaaacc tgttctttg atggggttta tcagccaaag     960
attaaagggc catttgtggc ttttgcagga ttctactaca agccagtgc tttaaatctt    1020
tcaggtagct tttccctgga caccttcaac tccagcacct ggaatttctg ctcacagaat    1080
tggagtcagc tcccactgct gctccccaaa tttgatgagg tatatgcccg ctcttactgc    1140
ttctcagcca actacatcta ccacttgttt gtgaacggtt acaaattcac agaggagact    1200
tggccccaaa tacactttga aaaagaagtg gggaatagca gcatagcctg gtctcttggc    1260
tacatgctca gcctgaccaa ccagatccca gctgaaagcc ctctgatccg tctgcccata    1320
gaaccacctg tctga                                                     1335
```

<210> SEQ ID NO 74
<211> LENGTH: 444
<212> TYPE: PRT
<213> ORGANISM: Homo sapiens

<400> SEQUENCE: 74

```
Met Gln Ile His Lys Gln Glu Val Leu Pro Pro Gly Leu Lys Tyr Gly
  1               5                  10                  15

Ile Val Leu Asp Ala Gly Ser Ser Ala Thr Arg Val Tyr Val Tyr Gln
             20                  25                  30

Trp Pro Ala Glu Lys Glu Asn Asn Thr Gly Val Val Ser Gln Thr Phe
         35                  40                  45

Lys Cys Ser Val Lys Gly Ser Gly Ile Ser Ser Tyr Gly Asn Asn Pro
     50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
```

|  |  |  |  |  |  |  |  |  |  |  | 85 |  |  |  |  | 90 |  |  |  |  | 95 |  |
|---|---|---|---|---|---|---|---|---|---|---|---|---|---|---|---|---|---|---|---|---|---|---|

Thr Ala Gly Met Arg Leu Leu Arg Leu Gln Asn Glu Thr Ala Ala Asn
            100                 105                 110
Glu Val Leu Glu Ser Ile Gln Ser Tyr Phe Lys Ser Gln Pro Phe Asp
            115                 120                 125
Phe Arg Gly Ala Gln Ile Ile Ser Gly Gln Glu Glu Gly Val Tyr Gly
        130                 135                 140
Trp Ile Thr Ala Asn Tyr Leu Met Gly Asn Phe Leu Glu Lys Asn Leu
145                 150                 155                 160
Trp His Met Trp Val His Pro His Gly Val Glu Thr Thr Gly Ala Leu
                    165                 170                 175
Asp Leu Gly Gly Ala Ser Thr Gln Ile Ser Phe Val Ala Gly Glu Lys
                180                 185                 190
Met Asp Leu Asn Thr Ser Asp Ile Met Gln Val Ser Leu Tyr Gly Tyr
            195                 200                 205
Val Tyr Thr Leu Tyr Thr His Ser Phe Gln Cys Tyr Gly Arg Asn Glu
        210                 215                 220
Ala Glu Lys Lys Phe Leu Ala Met Leu Leu Gln Asn Ser Pro Thr Lys
225                 230                 235                 240
Asn His Leu Thr Asn Pro Cys Tyr Pro Arg Asp Tyr Ser Ile Ser Phe
                    245                 250                 255
Thr Met Gly His Val Phe Asp Ser Leu Cys Thr Val Asp Gln Arg Pro
                260                 265                 270
Glu Ser Tyr Asn Pro Asn Asp Val Ile Thr Phe Glu Gly Thr Gly Asp
            275                 280                 285
Pro Ser Leu Cys Lys Glu Lys Val Ala Ser Ile Phe Asp Phe Lys Ala
        290                 295                 300
Cys His Asp Gln Glu Thr Cys Ser Phe Asp Gly Val Tyr Gln Pro Lys
305                 310                 315                 320
Ile Lys Gly Pro Phe Val Ala Phe Ala Gly Phe Tyr Tyr Thr Ala Ser
                    325                 330                 335
Ala Leu Asn Leu Ser Gly Ser Phe Ser Leu Asp Thr Phe Asn Ser Ser
                340                 345                 350
Thr Trp Asn Phe Cys Ser Gln Asn Trp Ser Gln Leu Pro Leu Leu Leu
            355                 360                 365
Pro Lys Phe Asp Glu Val Tyr Ala Arg Ser Tyr Cys Phe Ser Ala Asn
        370                 375                 380
Tyr Ile Tyr His Leu Phe Val Asn Gly Tyr Lys Phe Thr Glu Glu Thr
385                 390                 395                 400
Trp Pro Gln Ile His Phe Glu Lys Glu Val Gly Asn Ser Ser Ile Ala
                    405                 410                 415
Trp Ser Leu Gly Tyr Met Leu Ser Leu Thr Asn Gln Ile Pro Ala Glu
                420                 425                 430
Ser Pro Leu Ile Arg Leu Pro Ile Glu Pro Pro Val
            435                 440

<210> SEQ ID NO 75
<211> LENGTH: 1335
<212> TYPE: DNA
<213> ORGANISM: Homo sapiens

<400> SEQUENCE: 75
atgcagatcc acaagcaaga ggtcctccct ccaggactga gtatggtat tgtgctggat    60 gccgggtctt cagggacccg cgtctacgtg tatcaatggc cagcagaaaa agagaataat   120

-continued

```
accggagtgg tcagtcaaac cttcaaatgt agtgtgaaag gctctggaat ctccagctat      180
ggaaataacc cccaagatgt ccccagagcc tttgaggagt gtatgcaaaa agtcaagggg      240
caggttccat cccacctcca cggatccacc cccattcacc tgggagccac ggctgggatg      300
cgcttgctga ggttgcaaaa tgaaacagca gctaatgaag tccttgaaag catccaaagc      360
tacttcaagt cccagccctt tgactttagg ggtgctcaaa tcatttctgg caagaagaa       420
ggggtatatg gatggattac agccaactat ttaatgggaa atttcctgga agaacctg       480
tggcacatgt gggtgcaccc gcatggagtg gaaaccacgg gtgccctgga cttaggtggt      540
gcctccaccc aaatatcctt cgtggcagga gagaagatgg atctgaacac cagcgacatc      600
atgcaggtgt ccctgtatgg ctacgtatac acgctctaca cacacagctt ccagtgctat      660
ggccggaatg aggctgagaa aagtttctg gcaatgctcc tgcagaattc tcctaccaaa      720
aaccatctca ccaatccctg ttaccctcgg gattatagca tcagcttcac catgggccat      780
gtatttgata gcctgtgcac tgtggaccag aggccagaaa gttataaccc caatgatgtc      840
atcacttttg aaggaactgg ggacccatct ctgtgtaagg agaaggtggc ttccatattt      900
gacttcaaag cttgccatga tcaagaaacc tgttcttttg atggggttta tcagccaaag      960
attaaagggc catttgtggc ttttgcagga ttctactaca cagccagtgc tttaaatctt     1020
tcaggtagct tttccctgga caccttcaac tccagcacct ggaatttctg ctcacagaat     1080
tggagtcagc tcccactgct gctccccaaa tttgatgagg tatatgcccg ctcttactgc     1140
ttctcagcca actacatcta ccacttgttt gtgaacggtt acaaattcac agaggagact     1200
tggcccaaa tacactttga aaaagaagtg gggaatagca gcatagcctg gtctcttggc     1260
tacatgctca gcctgaccaa ccagatccca gctgaaagcc ctctgatccg tctgcccata     1320
gaaccacctg tctga                                                      1335
```

<210> SEQ ID NO 76
<211> LENGTH: 444
<212> TYPE: PRT
<213> ORGANISM: Homo sapiens

<400> SEQUENCE: 76

Met Gln Ile His Lys Gln Glu Val Leu Pro Gly Leu Lys Tyr Gly
 1               5                  10                  15

Ile Val Leu Asp Ala Gly Ser Ser Gly Thr Arg Val Tyr Val Gln
                20                  25                  30

Trp Pro Ala Glu Lys Glu Asn Asn Thr Gly Val Val Ser Gln Thr Phe
                35                  40                  45

Lys Cys Ser Val Lys Gly Ser Gly Ile Ser Ser Tyr Gly Asn Asn Pro
     50                  55                  60

Gln Asp Val Pro Arg Ala Phe Glu Glu Cys Met Gln Lys Val Lys Gly
65                  70                  75                  80

Gln Val Pro Ser His Leu His Gly Ser Thr Pro Ile His Leu Gly Ala
                85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
            115                 120                 125

Phe Arg Gly Ala Gln Ile Ile Ser Gly Gln Glu Glu Gly Val Tyr Gly
        130                 135                 140

Trp Ile Thr Ala Asn Tyr Leu Met Gly Asn Phe Leu Glu Lys Asn Leu

```
                145                 150                 155                 160
Trp His Met Trp Val His Pro His Gly Val Glu Thr Thr Gly Ala Leu
                    165                 170                 175
Asp Leu Gly Gly Ala Ser Thr Gln Ile Ser Phe Val Ala Gly Glu Lys
                180                 185                 190
Met Asp Leu Asn Thr Ser Asp Ile Met Gln Val Ser Leu Tyr Gly Tyr
            195                 200                 205
Val Tyr Thr Leu Tyr Thr His Ser Phe Gln Cys Tyr Gly Arg Asn Glu
        210                 215                 220
Ala Glu Lys Lys Phe Leu Ala Met Leu Leu Gln Asn Ser Pro Thr Lys
225                 230                 235                 240
Asn His Leu Thr Asn Pro Cys Tyr Pro Arg Asp Tyr Ser Ile Ser Phe
                245                 250                 255
Thr Met Gly His Val Phe Asp Ser Leu Cys Thr Val Asp Gln Arg Pro
                260                 265                 270
Glu Ser Tyr Asn Pro Asn Asp Val Ile Thr Phe Glu Gly Thr Gly Asp
            275                 280                 285
Pro Ser Leu Cys Lys Glu Lys Val Ala Ser Ile Phe Asp Phe Lys Ala
        290                 295                 300
Cys His Asp Gln Glu Thr Cys Ser Phe Asp Gly Val Tyr Gln Pro Lys
305                 310                 315                 320
Ile Lys Gly Pro Phe Val Ala Phe Ala Gly Phe Tyr Tyr Thr Ala Ser
                325                 330                 335
Ala Leu Asn Leu Ser Gly Ser Phe Ser Leu Asp Thr Phe Asn Ser Ser
                340                 345                 350
Thr Trp Asn Phe Cys Ser Gln Asn Trp Ser Gln Leu Pro Leu Leu Leu
                355                 360                 365
Pro Lys Phe Asp Glu Val Tyr Ala Arg Ser Tyr Cys Phe Ser Ala Asn
        370                 375                 380
Tyr Ile Tyr His Leu Phe Val Asn Gly Tyr Lys Phe Thr Glu Glu Thr
385                 390                 395                 400
Trp Pro Gln Ile His Phe Glu Lys Glu Val Gly Asn Ser Ser Ile Ala
                405                 410                 415
Trp Ser Leu Gly Tyr Met Leu Ser Leu Thr Asn Gln Ile Pro Ala Glu
                420                 425                 430
Ser Pro Leu Ile Arg Leu Pro Ile Glu Pro Pro Val
            435                 440

<210> SEQ ID NO 77
<211> LENGTH: 44
<212> TYPE: DNA
<213> ORGANISM: Artificial Sequence
<220> FEATURE:
<223> OTHER INFORMATION: Primer

<400> SEQUENCE: 77
aaaaaagata tcggctcgac gagcggcggg tcgacaagtg gtgg                    44

<210> SEQ ID NO 78
<211> LENGTH: 41
<212> TYPE: DNA
<213> ORGANISM: Artificial Sequence
<220> FEATURE:
<223> OTHER INFORMATION: Primer

<400> SEQUENCE: 78
gggtcgacaa gtggtggatc tactagtggc tctggatccg g                       41
```

<210> SEQ ID NO 79
<211> LENGTH: 40
<212> TYPE: DNA
<213> ORGANISM: Artificial Sequence
<220> FEATURE:
<223> OTHER INFORMATION: Primer

<400> SEQUENCE: 79
ctagtggctc tggatccgga atttgcaaga ctgggaatgg                               40

<210> SEQ ID NO 80
<211> LENGTH: 35
<212> TYPE: DNA
<213> ORGANISM: Artificial Sequence
<220> FEATURE:
<223> OTHER INFORMATION: Primer

<400> SEQUENCE: 80 tttttteccg ggttatcaac actcaagaat gtcgc                                   35

<210> SEQ ID NO 81
<211> LENGTH: 314
<212> TYPE: DNA
<213> ORGANISM: Artificial Sequence
<220> FEATURE:
<223> OTHER INFORMATION: Linker

<400> SEQUENCE: 81
gatatcggct cgacgagcgg cgggtcgaca agtggtggat ctactagtgg ctctggatcc         60
ggaatttgca agactgggaa tggaaagaac tacagaggga cgatgtccaa aacaaaaaat        120
ggcatcacct gtcaaaaatg gagttccact tctccccaca gacctagatt ctcacctgct        180
acacacccct cagagggact ggaggagaac tactgcagga atccagacaa cgatccgcag        240
gggccctggt gctatactac tgatccagaa aagagatatg actactgcga cattctgagt        300
gttgataacc cggg                                                          314

<210> SEQ ID NO 82
<211> LENGTH: 100
<212> TYPE: PRT
<213> ORGANISM: Artificial Sequence
<220> FEATURE:
<223> OTHER INFORMATION: Linker

<400> SEQUENCE: 82

Asp Ile Gly Ser Thr Ser Gly Gly Ser Thr Ser Gly Gly Ser Thr Ser
1               5                   10                  15

Gly Ser Gly Ser Gly Ile Cys Lys Thr Gly Asn Gly Lys Asn Tyr Arg
                20                  25                  30

Gly Thr Met Ser Lys Thr Lys Asn Gly Ile Thr Cys Gln Lys Trp Ser
            35                  40                  45

Ser Thr Ser Pro His Arg Pro Arg Phe Ser Pro Ala Thr His Pro Ser
        50                  55                  60

Glu Gly Leu Glu Glu Asn Tyr Cys Arg Asn Pro Asp Asn Asp Gln Gly
65                  70                  75                  80

Pro Trp Cys Tyr Thr Thr Asp Pro Glu Lys Arg Tyr Asp Tyr Cys Asp
                85                  90                  95

Ile Leu Glu Cys
            100

<210> SEQ ID NO 83
<211> LENGTH: 1326
<212> TYPE: DNA
<213> ORGANISM: Homo sapiens

<400> SEQUENCE: 83

```
atgcagaaca aagcattgcc agaaaacgtt aagtatggga ttgtgctgga tgcgggttct      60
tctcacacaa gtttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcattta cctgactgat tgcatggaaa gagctaggga agtgattcca     240
aggtcccagc accaagagac acccgtttac ctgggagcca cggcaggcat gcggttgctc     300
aggatggaaa gtgaagagtt ggcagacagg gttctggatg tggtggagag gagcctcagc     360
aactacccct ttgacttcca gggtgccagg atcattactg ccaagagga aggtgcctat      420
ggctggatta ctatcaacta tctgctgggc aaattcagtc agaaaacaag gtggttcagc     480
atagtcccat atgaaaccaa taatcaggaa acctttggag ctttggacct tggggagcc      540
tctacacaag tcacttttgt accccaaaac cagactatcg agtccccaga taatgctctg     600
caatttcgcc tctatggcaa ggactacaat gtctacacac atagcttctt gtgctatggg     660
aaggatcagg cactctggca gaaactggcc aaggacattc aggttgcaag taatgaaatt     720
ctcagggacc catgctttca tcctggatat aagaaggtag tgaacgtaag tgaccttac     780
aagacccct gcaccaagag atttgagatg actcttccat ccagcagtt tgaaatccag     840
ggtattggaa actatcaaca atgccatcaa agcatcctgg agctcttcaa caccagttac     900
tgcccttact cccagtgtgc cttcaatggg attttcttgc caccactcca ggggattt      960
ggggcatttt cagctttta ctttgtgatg aagttttta acttgacatc agagaaagtc     1020
tctcaggaaa aggtgactga gatgatgaaa aagttctgtg ctcagccttg ggaggagata    1080
aaaacatctt acgctggagt aaaggagaag tacctgagtg aatactgctt ttctggtacc    1140
tacattctct ccctccttct gcaaggctat catttcacag ctgattcctg ggagcacatc    1200
catttcattg gcaagatcca gggcagcgac gccggctgga cttgggcta catgctgaac     1260
ctgaccaaca tgatcccagc tgagcaacca ttgtccacac ctctctccca ctccaccgat    1320
atctga                                                              1326
```

<210> SEQ ID NO 84
<211> LENGTH: 441
<212> TYPE: PRT
<213> ORGANISM: Homo sapiens

<400> SEQUENCE: 84

```
Met Gln Asn Lys Ala Leu Pro Glu Asn Val Lys Tyr Gly Ile Val Leu
 1               5                  10                  15

Asp Ala Gly Ser Ser His Thr Ser Leu Tyr Ile Tyr Lys Trp Pro Ala
             20                  25                  30

Glu Lys Glu Asn Asp Thr Gly Val Val His Gln Val Glu Glu Cys Arg
         35                  40                  45

Val Lys Gly Pro Gly Ile Ser Lys Phe Val Gln Lys Val Asn Glu Ile
     50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                 85                  90                  95
```

```
Met Arg Leu Leu Arg Met Glu Ser Glu Glu Leu Ala Asp Arg Val Leu
                100                 105                 110

Asp Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
        130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
        210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
        290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
        370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr Asp Ile
        435                 440

<210> SEQ ID NO 85
<211> LENGTH: 1335
<212> TYPE: DNA
<213> ORGANISM: Homo sapiens

<400> SEQUENCE: 85
atgcagatcc acaagcaaga ggtcctccct ccaggactga agtatggtat tgtgctggat      60
gccgggtctt caagaaccac agtctacgtg tatcaatggc cagcagaaaa agagaataat     120
accggagtgg tcagtcaaac cttcaaatgt agtgtgaaag ctctggaat ctccagctat     180
```

-continued

```
ggaaataacc cccaagatgt ccccagagcc tttgaggagt gtatgcaaaa agtcaagggg      240
caggttccat cccacctcca cggatccacc cccattcacc tgggagccac ggctgggatg      300
cgcttgctga ggttgcaaaa tgaaacagca gctaatgaag tccttgaaag catccaaagc      360
tacttcaagt cccagccctt tgactttagg ggtgctcaaa tcatttctgg caagaagaa       420 ggggtatatg gatggattac agccaactat ttaatgggaa atttcctgga gaagaacctg      480
tggcacatgt gggtgcaccc gcatggagtg gaaaccacgg gtgccctgga cttaggtggt      540
gcctccaccc aaatatcctt cgtggcagga gagaagatgg atctgaacac cagcgacatc      600
atgcaggtgt ccctgtatgg ctacgtatac acgctctaca cacacagctt ccagtgctat      660
ggccggaatg aggctgagaa gaagtttctg gcaatgctcc tgcagaattc tcctaccaaa      720
aaccatctca ccaatccctg ttaccctcgg gattatagca tcagcttcac catgggccat      780
gtatttgata gcctgtgcac tgtggaccag aggccagaaa gttataaccc caatgatgtc      840 atcactttg aaggaactgg ggacccatct ctgtgtaagg agaaggtggc ttccatattt       900
gacttcaaag cttgccatga tcaagaaacc tgttctttg atggggttta tcagccaaag       960 attaagggc catttgtggc ttttgcagga ttctactaca cagccagtgc tttaaatctt      1020
tcaggtagct tttccctgga caccttcaac tccagcacct ggaatttctg ctcacagaat      1080
tggagtcagc tcccactgct gctccccaaa tttgatgagg tatatgcccg ctcttactgc      1140
ttctcagcca actacatcta ccacttgttt gtgaacggtt acaaattcac agaggagact      1200 tggcccaaa tacactttga aaagaagtg gggaatagca gcatagcctg gtctcttggc       1260
tacatgctca gcctgaccaa ccagatccca gctgaaagcc ctctgatccg tctgcccata      1320
gaaccagata tctga                                                      1335
```

<210> SEQ ID NO 86
<211> LENGTH: 444
<212> TYPE: PRT
<213> ORGANISM: Homo sapiens

<400> SEQUENCE: 86

```
Met Gln Ile His Lys Gln Glu Val Leu Pro Pro Gly Leu Lys Tyr Gly
  1               5                  10                  15

Ile Val Leu Asp Ala Gly Ser Ser Arg Thr Thr Val Tyr Val Tyr Gln
             20                  25                  30

Trp Pro Ala Glu Lys Glu Asn Asn Thr Gly Val Val Ser Gln Thr Phe
         35                  40                  45

Lys Cys Ser Val Lys Gly Ser Gly Ile Ser Ser Tyr Gly Asn Asn Pro
     50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Glu Gly Val Tyr Gly
    130                 135                 140

Trp Ile Thr Ala Asn Tyr Leu Met Gly Asn Phe Leu Glu Lys Asn Leu
145                 150                 155                 160
```

```
Trp His Met Trp Val His Pro His Gly Val Glu Thr Gly Ala Leu
            165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
            195                 200                 205

Val Tyr Thr Leu Tyr Thr His Ser Phe Gln Cys Tyr Gly Arg Asn Glu
210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
            245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
            275                 280                 285

Pro Ser Leu Cys Lys Glu Lys Val Ala Ser Ile Phe Asp Phe Lys Ala
290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
            325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
            355                 360                 365

Pro Lys Phe Asp Glu Val Tyr Ala Arg Ser Tyr Cys Phe Ser Ala Asn
            370                 375                 380

Tyr Ile Tyr His Leu Phe Val Asn Gly Tyr Lys Phe Thr Glu Thr
385                 390                 395                 400

Trp Pro Gln Ile His Phe Glu Lys Glu Val Gly Asn Ser Ser Ile Ala
            405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Asp Ile
            435                 440

<210> SEQ ID NO 87
<211> LENGTH: 1335
<212> TYPE: DNA
<213> ORGANISM: Homo sapiens

<400> SEQUENCE: 87
atgcagatcc acaagcaaga ggtcctccct ccaggactga agtatggtat tgtgctggat    60
gccgggtctt cagcgacccg cgtctacgtg tatcaatggc cagcagaaaa agagaataat   120
accggagtgg tcagtcaaac cttcaaatgt agtgtgaaag ctctggaat ctccagctat   180 ggaaataacc cccaagatgt ccccagagcc tttgaggagt gtatgcaaaa agtcaagggg   240
caggttccat cccacctcca cggatccacc cccattcacc tgggagccac ggctgggatg   300
cgcttgctga ggttgcaaaa tgaaacagca gctaatgaag tccttgaaag catccaaagc   360
tacttcaagt cccagcccct tgactttagg ggtgctcaaa tcatttctgg caagaagaa   420 ggggtatatg gatggattac agccaactat ttaatgggaa atttcctgga agagaacctg   480
tggcacatgt gggtgcaccc gcatggagtg gaaaccacgg gtgccctgga cttaggtggt   540
```

-continued

```
gcctccaccc aaatatcctt cgtggcagga gagaagatgg atctgaacac cagcgacatc      600
atgcaggtgt ccctgtatgg ctacgtatac acgctctaca cacacagctt ccagtgctat      660
ggccggaatg aggctgagaa gaagtttctg gcaatgctcc tgcagaattc tcctaccaaa      720
aaccatctca ccaatccctg ttaccctcgg gattatagca tcagcttcac catgggccat      780
gtatttgata gcctgtgcac tgtggaccag aggccagaaa gttataaccc caatgatgtc      840 atcactttg aaggaactgg ggacccatct ctgtgtaagg agaaggtggc ttccatattt       900
gacttcaaag cttgccatga tcaagaaacc tgttcttttg atggggttta tcagccaaag      960
attaaagggc catttgtggc ttttgcagga ttctactaca cagccagtgc tttaaatctt     1020
tcaggtagct tttccctgga caccttcaac tccagcacct ggaatttctg ctcacagaat     1080
tggagtcagc tcccactgct gctccccaaa tttgatgagg tatatgcccg ctcttactgc     1140
ttctcagcca actacatcta ccacttgttt gtgaacggtt acaaattcac agaggagact     1200 tggcccccaaa tacactttga aaaagaagtg gggaatagca gcatagcctg gtctcttggc    1260
tacatgctca gcctgaccaa ccagatccca gctgaaagcc ctctgatccg tctgcccata     1320
gaaccagata tctga                                                       1335
```

<210> SEQ ID NO 88
<211> LENGTH: 444
<212> TYPE: PRT
<213> ORGANISM: Homo sapiens

<400> SEQUENCE: 88

```
Met Gln Ile His Lys Gln Glu Val Leu Pro Pro Gly Leu Lys Tyr Gly
 1               5                  10                  15

Ile Val Leu Asp Ala Gly Ser Ser Ala Thr Arg Val Tyr Val Tyr Gln
                20                  25                  30

Trp Pro Ala Glu Lys Glu Asn Asn Thr Gly Val Val Ser Gln Thr Phe
            35                  40                  45

Lys Cys Ser Val Lys Gly Ser Gly Ile Ser Ser Tyr Gly Asn Asn Pro
         50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Glu Gly Val Tyr Gly
    130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
    210                 215                 220
```

| Ala | Glu | Lys | Lys | Phe | Leu | Ala | Met | Leu | Leu | Gln | Asn | Ser | Pro | Thr | Lys |
| | 225 | | | | 230 | | | | | 235 | | | | | 240 |

| Asn | His | Leu | Thr | Asn | Pro | Cys | Tyr | Pro | Arg | Asp | Tyr | Ser | Ile | Ser | Phe |
| | | | | 245 | | | | | 250 | | | | | 255 | |

| Thr | Met | Gly | His | Val | Phe | Asp | Ser | Leu | Cys | Thr | Val | Asp | Gln | Arg | Pro |
| | | | | 260 | | | | | 265 | | | | | 270 | |

| Glu | Ser | Tyr | Asn | Pro | Asn | Asp | Val | Ile | Thr | Phe | Glu | Gly | Thr | Gly | Asp |
| | | | 275 | | | | | 280 | | | | | 285 | | |

| Pro | Ser | Leu | Cys | Lys | Glu | Lys | Val | Ala | Ser | Ile | Phe | Asp | Phe | Lys | Ala |
| | | | 290 | | | | | 295 | | | | | 300 | | |

| Cys | His | Asp | Gln | Glu | Thr | Cys | Ser | Phe | Asp | Gly | Val | Tyr | Gln | Pro | Lys |
| 305 | | | | | 310 | | | | | 315 | | | | | 320 |

| Ile | Lys | Gly | Pro | Phe | Val | Ala | Phe | Ala | Gly | Phe | Tyr | Tyr | Thr | Ala | Ser |
| | | | | 325 | | | | | 330 | | | | | 335 | |

| Ala | Leu | Asn | Leu | Ser | Gly | Ser | Phe | Ser | Leu | Asp | Thr | Phe | Asn | Ser | Ser |
| | | | | 340 | | | | | 345 | | | | | 350 | |

| Thr | Trp | Asn | Phe | Cys | Ser | Gln | Asn | Trp | Ser | Gln | Leu | Pro | Leu | Leu | Leu |
| | | | | 355 | | | | | 360 | | | | | 365 | |

| Pro | Lys | Phe | Asp | Glu | Val | Tyr | Ala | Arg | Ser | Tyr | Cys | Phe | Ser | Ala | Asn |
| | | | 370 | | | | | 375 | | | | | 380 | | |

| Tyr | Ile | Tyr | His | Leu | Phe | Val | Asn | Gly | Tyr | Lys | Phe | Thr | Glu | Glu | Thr |
| 385 | | | | | 390 | | | | | 395 | | | | | 400 |

| Trp | Pro | Gln | Ile | His | Phe | Glu | Lys | Glu | Val | Gly | Asn | Ser | Ser | Ile | Ala |
| | | | | 405 | | | | | 410 | | | | | 415 | |

| Trp | Ser | Leu | Gly | Tyr | Met | Leu | Ser | Leu | Thr | Asn | Gln | Ile | Pro | Ala | Glu |
| | | | | 420 | | | | | 425 | | | | | 430 | |

| Ser | Pro | Leu | Ile | Arg | Leu | Pro | Ile | Glu | Pro | Asp | Ile |
| | | | | 435 | | | | | 440 | | |

<210> SEQ ID NO 89
<211> LENGTH: 1335
<212> TYPE: DNA
<213> ORGANISM: Homo sapiens

<400> SEQUENCE: 89

| atgcagatcc acaagcaaga ggtcctccct ccaggactga agtatggtat tgtgctggat | 60 |
| gccgggtctt cagggacccg cgtctacgtg tatcaatggc agcagaaaaa agagaataat | 120 |
| accggagtgg tcagtcaaac cttcaaatgt agtgtgaaag ctctggaat ctccagctat | 180 |
| ggaaataacc cccaagatgt ccccagagcc tttgaggagt gtatgcaaaa agtcaagggg | 240 |
| caggttccat cccacctcca cggatccacc ccattcacc tgggagccac ggctgggatg | 300 |
| cgcttgctga ggttgcaaaa tgaaacagca gctaatgaag tccttgaaag catccaaagc | 360 |
| tacttcaagt cccagccctt tgactttagg ggtgctcaaa tcatttctgg caagaagaa | 420 |
| ggggtatatg gatggattac agccaactat ttaatggaaa atttcctgga agaacctg | 480 |
| tggcacatgt gggtgcaccc gcatggagtg gaaaccacgg gtgccctgga cttaggtggt | 540 |
| gcctccaccc aaatatcctt cgtggcagga gagaagatgg atctgaacac cagcgacatc | 600 |
| atgcaggtgt ccctgtatgg ctacgtatac acgctctaca cacacagctt ccagtgctat | 660 |
| ggccggaatg aggctgagaa gaagtttctg gcatgctcc tgcagaattc tcctaccaaa | 720 |
| aaccatctca ccaatccctg ttaccctcgg gattatagca tcagcttcac catgggccat | 780 |
| gtatttgata gcctgtgcac tgtggaccag aggccagaaa gttataaccc caatgatgtc | 840 |
| atcactttg aaggaactgg ggacccatct ctgtgtaagg agaaggtggc ttccatattt | 900 |

-continued

```
gacttcaaag cttgccatga tcaagaaacc tgttcttttg atggggttta tcagccaaag    960
attaaagggc catttgtggc ttttgcagga ttctactaca cagccagtgc tttaaatctt   1020
tcaggtagct tttccctgga caccttcaac tccagcacct ggaatttctg ctcacagaat   1080
tggagtcagc tcccactgct gctccccaaa tttgatgagg tatatgcccg ctcttactgc   1140
ttctcagcca actacatcta ccacttgttt gtgaacggtt acaaattcac agaggagact   1200 tggcccccaaa tacactttga aaagaagtg gggaatagca gcatagcctg gtctcttggc    1260
tacatgctca gcctgaccaa ccagatccca gctgaaagcc ctctgatccg tctgcccata   1320
gaaccagata tctga                                                    1335
```

<210> SEQ ID NO 90
<211> LENGTH: 444
<212> TYPE: PRT
<213> ORGANISM: Homo sapiens

<400> SEQUENCE: 90

```
Met Gln Ile His Lys Gln Glu Val Leu Pro Gly Leu Lys Tyr Gly
 1               5                  10                  15

Ile Val Leu Asp Ala Gly Ser Ser Gly Thr Arg Val Tyr Val Gln
                20                  25                  30

Trp Pro Ala Glu Lys Glu Asn Asn Thr Gly Val Val Ser Gln Thr Phe
                35                  40                  45

Lys Cys Ser Val Lys Gly Ser Gly Ile Ser Ser Tyr Gly Asn Asn Pro
50                  55                  60

Gln Asp Val Pro Arg Ala Phe Glu Glu Cys Met Gln Lys Val Lys Gly
65                  70                  75                  80

Gln Val Pro Ser His Leu His Gly Ser Thr Pro Ile His Leu Gly Ala
                    85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
                115                 120                 125

Phe Arg Gly Ala Gln Ile Ile Ser Gly Gln Glu Glu Gly Val Tyr Gly
            130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                    165                 170                 175

Asp Leu Gly Gly Ala Ser Thr Gln Ile Ser Phe Val Ala Gly Glu Lys
                180                 185                 190

Met Asp Leu Asn Thr Ser Asp Ile Met Gln Val Ser Leu Tyr Gly Tyr
                195                 200                 205

Val Tyr Thr Leu Tyr Thr His Ser Phe Gln Cys Tyr Gly Arg Asn Glu
            210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                    245                 250                 255

Thr Met Gly His Val Phe Asp Ser Leu Cys Thr Val Asp Gln Arg Pro
                260                 265                 270

Glu Ser Tyr Asn Pro Asn Asp Val Ile Thr Phe Glu Gly Thr Gly Asp
            275                 280                 285
```

```
Pro Ser Leu Cys Lys Glu Lys Val Ala Ser Ile Phe Asp Phe Lys Ala
    290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
        355                 360                 365

Pro Lys Phe Asp Glu Val Tyr Ala Arg Ser Tyr Cys Phe Ser Ala Asn
    370                 375                 380

Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
                405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Asp Ile
        435                 440

<210> SEQ ID NO 91
<211> LENGTH: 1626
<212> TYPE: DNA
<213> ORGANISM: Artificial Sequence
<220> FEATURE:
<223> OTHER INFORMATION: Linker

<400> SEQUENCE: 91
atgcagaaca aagcattgcc agaaaacgtt aagtatggga ttgtgctgga tgcgggttct      60
tctcacacaa gtttatacat ctataagtgg ccagcagaaa aggagaatga cacaggcgtg     120
gtgcatcaag tagaagaatg cagggttaaa ggtcctggaa tctcaaaatt tgttcagaaa     180
gtaaatgaaa taggcattta cctgactgat tgcatggaaa gagctaggga agtgattcca     240
aggtcccagc accaagagac acccgtttac ctgggagcca cggcaggcat gcggttgctc     300
aggatggaaa gtgaagagtt ggcagacagg gttctggatg tggtggagag gagcctcagc     360 aactaccccct ttgacttcca gggtgccagg atcattactg gccaagagga aggtgcctat     420
ggctggatta ctatcaacta tctgctgggc aaattcagtc agaaaacaag gtggttcagc     480
atagtcccat atgaaaccaa taatcaggaa acctttggag ctttggacct tgggggagcc     540
tctacacaag tcacttttgt accccaaaac cagactatcg agtccccaga taatgctctg     600
caatttcgcc tctatggcaa ggactacaat gtctacacac atagcttctt gtgctatggg     660
aaggatcagg cactctggca gaaactggcc aaggacattc aggttgcaag taatgaaatt     720
ctcagggacc catgctttca tcctggatat aagaaggtag tgaacgtaag tgaccttac      780 aagacccct gcaccaagag atttgagatg actcttccat ccagcagtt tgaaatccag      840 ggtattggaa actatcaaca atgccatcaa agcatcctgg agctcttcaa caccagttac     900
tgcccttact cccagtgtgc cttcaatggg attttcttgc accactcca ggggattttt      960 ggggcatttt cagcttttta ctttgtgatg aagttttaa acttgacatc agagaaagtc     1020
tctcaggaaa aggtgactga gatgataaa agttctgtg ctcagccttg ggaggagata     1080
aaaacatctt acgctggagt aaaggagaag tacctgagtg aatactgctt ttctggtacc     1140
tacattctct ccctccttct gcaaggctat catttcacag ctgattcctg ggagcacatc     1200
```

-continued

```
catttcattg gcaagatcca gggcagcgac gccggctgga ctttgggcta catgctgaac    1260
ctgaccaaca tgatcccagc tgagcaacca ttgtccacac ctctctccca ctccaccgat    1320
atcggctcga cgagcggcgg gtcgacaagt ggtggatcta ctagtggctc tggatccgga    1380
atttgcaaga ctgggaatgg aaagaactac agagggacga tgtccaaaac aaaaaatggc    1440
atcacctgtc aaaatggag ttccacttct ccccacagac ctagattctc acctgctaca    1500 caccccctcag agggactgga ggagaactac tgcaggaatc cagacaacga tccgcagggg    1560
ccctggtgct atactactga tccagaaaag agatatgact actgcgacat tcttgagtgt    1620
tgataa                                                                 1626
```

<210> SEQ ID NO 92
<211> LENGTH: 540
<212> TYPE: PRT
<213> ORGANISM: Artificial Sequence
<220> FEATURE:
<223> OTHER INFORMATION: Linker

<400> SEQUENCE: 92

```
Met Gln Asn Lys Ala Leu Pro Glu Asn Val Lys Tyr Gly Ile Val Leu
 1               5                  10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
           100                 105                 110

Asp Val Val Glu Arg Ser Leu Ser Asn Tyr Pro Phe Asp Phe Gln Gly
       115                 120                 125

Ala Arg Ile Ile Thr Gly Gln Glu Glu Gly Ala Tyr Gly Trp Ile Thr
   130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
```

```
                  275                 280                 285
His Gln Ser Ile Leu Glu Leu Phe Asn Thr Ser Tyr Cys Pro Tyr Ser
            290                 295                 300
Gln Cys Ala Phe Asn Gly Ile Phe Leu Pro Pro Leu Gln Gly Asp Phe
305                 310                 315                 320
Gly Ala Phe Ser Ala Phe Tyr Phe Val Met Lys Phe Leu Asn Leu Thr
                325                 330                 335
Ser Glu Lys Val Ser Gln Glu Lys Val Thr Glu Met Met Lys Lys Phe
            340                 345                 350
Cys Ala Gln Pro Trp Glu Glu Ile Lys Thr Ser Tyr Ala Gly Val Lys
        355                 360                 365
Glu Lys Tyr Leu Ser Glu Tyr Cys Phe Ser Gly Thr Tyr Ile Leu Ser
    370                 375                 380
Leu Leu Leu Gln Gly Tyr His Phe Thr Ala Asp Ser Trp Glu His Ile
385                 390                 395                 400
His Phe Ile Gly Lys Ile Gln Gly Ser Asp Ala Gly Trp Thr Leu Gly
                405                 410                 415
Tyr Met Leu Asn Leu Thr Asn Met Ile Pro Ala Glu Gln Pro Leu Ser
            420                 425                 430
Thr Pro Leu Ser His Ser Thr Asp Ile Gly Ser Thr Ser Gly Gly Ser
        435                 440                 445
Thr Ser Gly Gly Ser Thr Ser Gly Ser Gly Ser Gly Ile Cys Lys Thr
    450                 455                 460
Gly Asn Gly Lys Asn Tyr Arg Gly Thr Met Ser Lys Thr Lys Asn Gly
465                 470                 475                 480
Ile Thr Cys Gln Lys Trp Ser Ser Thr Ser Pro His Arg Pro Arg Phe
                485                 490                 495
Ser Pro Ala Thr His Pro Ser Glu Gly Leu Glu Glu Asn Tyr Cys Arg
            500                 505                 510
Asn Pro Asp Asn Asp Pro Gln Gly Pro Trp Cys Tyr Thr Thr Asp Pro
        515                 520                 525
Glu Lys Arg Tyr Asp Tyr Cys Asp Ile Leu Glu Cys
    530                 535                 540

<210> SEQ ID NO 93
<211> LENGTH: 1632
<212> TYPE: DNA
<213> ORGANISM: Artificial Sequence
<220> FEATURE:
<223> OTHER INFORMATION: Linker

<400> SEQUENCE: 93
atgcagatcc acaagcaaga ggtcctccct ccaggactga gtatggtat tgtgctggat    60 gccgggtctt caagaaccac agtctacgtg tatcaatggc cagcagaaaa agagaataat   120
accggagtgg tcagtcaaac cttcaaatgt agtgtgaaag ctctggaat ctccagctat   180 ggaaataacc cccaagatgt ccccagagcc tttgaggagt gtatgcaaaa agtcaagggg   240
caggttccat cccacctcca cggatccacc cccattcacc tgggagccac ggctgggatg   300
cgcttgctga ggttgcaaaa tgaaacagca gctaatgaag tccttgaaag catccaaagc   360
tacttcaagt cccagccctt tgactttagg ggtgctcaaa tcatttctgg caagaagaa   420 ggggtatatg atggattac agccaactat ttaatgggaa atttcctgga agagaacctg   480
tggcacatgt gggtgcaccc gcatggagtg aaaccacgg tgccctgga cttaggtggt   540 gcctccaccc aaatatcctt cgtggcagga gagaagatgg atctgaacac cagcgacatc   600
```

-continued

```
atgcaggtgt ccctgtatgg ctacgtatac acgctctaca cacacagctt ccagtgctat    660
ggccggaatg aggctgagaa gaagtttctg gcaatgctcc tgcagaattc tcctaccaaa    720
aaccatctca ccaatccctg ttaccctcgg gattatagca tcagcttcac catgggccat    780
gtatttgata gcctgtgcac tgtggaccag aggccagaaa gttataaccc caatgatgtc    840
atcacttttg aaggaactgg ggacccatct ctgtgtaagg agaaggtggc ttccatattt    900
gacttcaaag cttgccatga tcaagaaacc tgttcttttg atggggttta tcagccaaag    960
attaaagggc catttgtggc ttttgcagga ttctactaca cagccagtgc tttaaatctt   1020
tcaggtagct tttccctgga caccttcaac tccagcacct ggaatttctg ctcacagaat   1080
tggagtcagc tcccactgct gctcccaaa tttgatgagg tatatgcccg ctcttactgc   1140
ttctcagcca actacatcta ccacttgttt gtgaacggtt acaaattcac agaggagact   1200
tggccccaaa tacactttga aaagaagtg gggaatagca gcatagcctg gtctcttggc   1260
tacatgctca gcctgaccaa ccagatccca gctgaaagcc ctctgatccg tctgcccata   1320
gaaccagata tcggctcgac gagcggcggg tcgacaagtg gtggatctac tagtggctct   1380
ggatccggaa tttgcaagac tgggaatgga agaactaca gagggacgat gtccaaaaca   1440
aaaaatggca tcacctgtca aaatggagt tccacttctc cccacagacc tagattctca   1500
cctgctacac acccctcaga gggactggag gagaactact gcaggaatcc agacaacgat   1560
ccgcaggggc cctggtgcta ctactactgat ccagaaaaga gatatgacta ctgcgacatt   1620
cttgagtgtt ga                                                       1632
```

<210> SEQ ID NO 94
<211> LENGTH: 543
<212> TYPE: PRT
<213> ORGANISM: Artificial Sequence
<220> FEATURE:
<223> OTHER INFORMATION: Linker

<400> SEQUENCE: 94

```
Met Gln Ile His Lys Gln Glu Val Leu Pro Gly Leu Lys Tyr Gly
  1               5                  10                  15

Ile Val Leu Asp Ala Gly Ser Ser Arg Thr Thr Val Tyr Val Tyr Gln
                 20                  25                  30

Trp Pro Ala Glu Lys Glu Asn Asn Thr Gly Val Val Ser Gln Thr Phe
             35                  40                  45

Lys Cys Ser Val Lys Gly Ser Gly Ile Ser Ser Tyr Gly Asn Asn Pro
         50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
            115                 120                 125

Phe Arg Gly Ala Gln Ile Ile Ser Gly Gln Glu Glu Gly Val Tyr Gly
        130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175
```

```
Asp Leu Gly Gly Ala Ser Thr Gln Ile Ser Phe Val Ala Gly Glu Lys
            180                 185                 190
Met Asp Leu Asn Thr Ser Asp Ile Met Gln Val Ser Leu Tyr Gly Tyr
        195                 200                 205
Val Tyr Thr Leu Tyr Thr His Ser Phe Gln Cys Tyr Gly Arg Asn Glu
    210                 215                 220
Ala Glu Lys Lys Phe Leu Ala Met Leu Leu Gln Asn Ser Pro Thr Lys
225                 230                 235                 240
Asn His Leu Thr Asn Pro Cys Tyr Pro Arg Asp Tyr Ser Ile Ser Phe
                245                 250                 255
Thr Met Gly His Val Phe Asp Ser Leu Cys Thr Val Asp Gln Arg Pro
            260                 265                 270
Glu Ser Tyr Asn Pro Asn Asp Val Ile Thr Phe Glu Gly Thr Gly Asp
        275                 280                 285
Pro Ser Leu Cys Lys Glu Lys Val Ala Ser Ile Phe Asp Phe Lys Ala
    290                 295                 300
Cys His Asp Gln Glu Thr Cys Ser Phe Asp Gly Val Tyr Gln Pro Lys
305                 310                 315                 320
Ile Lys Gly Pro Phe Val Ala Phe Ala Gly Phe Tyr Tyr Thr Ala Ser
                325                 330                 335
Ala Leu Asn Leu Ser Gly Ser Phe Ser Leu Asp Thr Phe Asn Ser Ser
            340                 345                 350
Thr Trp Asn Phe Cys Ser Gln Asn Trp Ser Gln Leu Pro Leu Leu Leu
        355                 360                 365
Pro Lys Phe Asp Glu Val Tyr Ala Arg Ser Tyr Cys Phe Ser Ala Asn
    370                 375                 380
Tyr Ile Tyr His Leu Phe Val Asn Gly Tyr Lys Phe Thr Glu Glu Thr
385                 390                 395                 400
Trp Pro Gln Ile His Phe Glu Lys Glu Val Gly Asn Ser Ser Ile Ala
                405                 410                 415
Trp Ser Leu Gly Tyr Met Leu Ser Leu Thr Asn Gln Ile Pro Ala Glu
            420                 425                 430
Ser Pro Leu Ile Arg Leu Pro Ile Glu Pro Asp Ile Gly Ser Thr Ser
        435                 440                 445
Gly Gly Ser Thr Ser Gly Gly Ser Thr Gly Ser Gly Ser Gly Ile
    450                 455                 460
Cys Lys Thr Gly Asn Gly Lys Asn Tyr Arg Gly Thr Met Ser Lys Thr
465                 470                 475                 480
Lys Asn Gly Ile Thr Cys Gln Lys Trp Ser Ser Thr Ser Pro His Arg
                485                 490                 495
Pro Arg Phe Ser Pro Ala Thr His Pro Ser Glu Gly Leu Glu Glu Asn
            500                 505                 510
Tyr Cys Arg Asn Pro Asp Asn Asp Pro Gln Gly Pro Trp Cys Tyr Thr
        515                 520                 525
Thr Asp Pro Glu Lys Arg Tyr Asp Tyr Cys Asp Ile Leu Glu Cys
    530                 535                 540
```

<210> SEQ ID NO 95
<211> LENGTH: 1632
<212> TYPE: DNA
<213> ORGANISM: Artificial Sequence
<220> FEATURE:
<223> OTHER INFORMATION: Linker

<400> SEQUENCE: 95

```
atgcagatcc acaagcaaga ggtcctccct ccaggactga agtatggtat tgtgctggat      60
gccgggtctt cagcgacccg cgtctacgtg tatcaatggc cagcagaaaa agagaataat     120
accggagtgg tcagtcaaac cttcaaatgt agtgtgaaag ctctggaat ctccagctat      180
ggaaataacc cccaagatgt ccccagagcc tttgaggagt gtatgcaaaa agtcaagggg     240
caggttccat cccacctcca cggatccacc cccattcacc tgggagccac ggctgggatg     300
cgcttgctga ggttgcaaaa tgaaacagca gctaatgaag tccttgaaag catccaaagc     360
tacttcaagt cccagccctt tgactttagg ggtgctcaaa tcatttctgg caagaagaa      420
ggggtatatg gatggattac agccaactat ttaatgggaa atttcctgga gaagaacctg     480
tggcacatgt gggtgcaccc gcatggagtg gaaaccacgg tgccctgga cttaggtggt      540
gcctccaccc aaatatcctt cgtggcagga gagaagatgg atctgaacac cagcgacatc     600
atgcaggtgt ccctgtatgg ctacgtatac acgctctaca cacacagctt ccagtgctat     660
ggccggaatg aggctgagaa gaagtttctg gcaatgctcc tgcagaattc tcctaccaaa     720
aaccatctca ccaatccctg ttaccctcgg gattatagca tcagcttcac catgggccat     780
gtatttgata gcctgtgcac tgtggaccag aggccagaaa gttataaccc caatgatgtc     840
atcactttg aaggaactgg ggacccatct ctgtgtaagg agaaggtggc ttccatattt      900
gacttcaaag cttgccatga tcaagaaacc tgttctttg atgggttta tcagccaaag       960
attaaagggc catttgtggc ttttgcagga ttctactaca cagccagtgc tttaaatctt    1020
tcaggtagct tttccctgga caccttcaac tccagcacct ggaatttctg ctcacagaat    1080
tggagtcagc tcccactgct gctccccaaa tttgatgagg tatatgcccg ctcttactgc    1140
ttctcagcca actacatcta ccacttgttt gtgaacggtt acaaattcac agaggagact    1200
tggccccaaa tacactttga aaaagaagtg gggaatagca gcatagcctg gtctcttggc    1260
tacatgctca gcctgaccaa ccagatccca gctgaaagcc ctctgatccg tctgcccata    1320
gaaccagata tcggctcgac gagcggcggg tcgacaagtg gtggatctac tagtggctct    1380
ggatccggaa tttgcaagac tgggaatgga aagaactaca gagggacgat gtccaaaaca    1440
aaaaatggca tcacctgtca aaaatggagt tccacttctc cccacagacc tagattctca    1500
cctgctacac accccctcaga gggactggag gagaactact gcaggaatcc agacaacgat    1560
ccgcaggggc cctggtgcta ctactgtgat ccagaaaaga gatatgacta ctgcgacatt    1620
cttgagtgtt ga                                                         1632
```

<210> SEQ ID NO 96
<211> LENGTH: 543
<212> TYPE: PRT
<213> ORGANISM: Artificial Sequence
<220> FEATURE:
<223> OTHER INFORMATION: Linker

<400> SEQUENCE: 96

Met Gln Ile His Lys Gln Glu Val Leu Pro Pro Gly Leu Lys Tyr Gly
1               5                   10                  15

Ile Val Leu Asp Ala Gly Ser Ser Ala Thr Arg Val Tyr Val Tyr Gln
            20                  25                  30

Trp Pro Ala Glu Lys Glu Asn Asn Thr Gly Val Val Ser Gln Thr Phe
        35                  40                  45

Lys Cys Ser Val Lys Gly Ser Gly Ile Ser Ser Tyr Gly Asn Asn Pro
    50                  55                  60

```
Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Gly Val Tyr Gly
    130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
    210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
        275                 280                 285

Pro Ser Leu Cys Lys Glu Lys Val Ala Ser Ile Phe Asp Phe Lys Ala
    290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
        355                 360                 365

Pro Lys Phe Asp Glu Val Tyr Ala Arg Ser Tyr Cys Phe Ser Ala Asn
    370                 375                 380

Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
                405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Asp Ile Gly Ser Thr Ser
        435                 440                 445

Gly Gly Ser Thr Ser Gly Gly Ser Thr Ser Gly Ser Gly Ser Gly Ile
    450                 455                 460

Cys Lys Thr Gly Asn Gly Lys Asn Tyr Arg Gly Thr Met Ser Lys Thr
465                 470                 475                 480

Lys Asn Gly Ile Thr Cys Gln Lys Trp Ser Ser Thr Ser Pro His Arg
```

```
                485                 490                 495
Pro Arg Phe Ser Pro Ala Thr His Pro Ser Glu Gly Leu Glu Glu Asn
            500                 505                 510

Tyr Cys Arg Asn Pro Asp Asn Asp Pro Gln Gly Pro Trp Cys Tyr Thr
        515                 520                 525

Thr Asp Pro Glu Lys Arg Tyr Asp Tyr Cys Asp Ile Leu Glu Cys
        530                 535                 540

<210> SEQ ID NO 97
<211> LENGTH: 1632
<212> TYPE: DNA
<213> ORGANISM: Artificial Sequence
<220> FEATURE:
<223> OTHER INFORMATION: Linker

<400> SEQUENCE: 97
atgcagatcc acaagcaaga ggtcctccct ccaggactga agtatggtat tgtgctggat    60
gccgggtctt cagggacccg cgtctacgtg tatcaatggc cagcagaaaa agagaataat   120
accggagtgg tcagtcaaac cttcaaatgt agtgtgaaag ctctggaat ctccagctat    180 ggaaataacc cccaagatgt ccccagagcc tttgaggagt gtatgcaaaa agtcaagggg   240
caggttccat cccacctcca cggatccacc cccattcacc tgggagccac ggctgggatg   300
cgcttgctga ggttgcaaaa tgaaacagca gctaatgaag tccttgaaag catccaaagc   360
tacttcaagt cccagccctt tgactttagg ggtgctcaaa tcatttctgg caagaagaa    420 ggggtatatg gatggattac agccaactat ttaatgggaa atttcctgga agagaacctg   480
tggcacatgt gggtgcaccc gcatggagtg gaaaccacgg tgccctgga cttaggtggt    540 gcctccaccc aaatatcctt cgtggcagga gagaagatgg atctgaacac cagcgacatc   600
atgcaggtgt ccctgtatgg ctacgtatac acgctctaca cacagcttt ccagtgctat    660 ggccggaatg aggctgagaa gaagtttctg gcaatgctcc tgcagaattc tcctaccaaa   720
aaccatctca ccaatccctg ttaccctcgg gattatagca tcagcttcac catgggccat   780
gtatttgata gcctgtgcac tgtggaccag aggccagaaa gttataaccc caatgatgtc   840
atcacttttg aaggaactgg ggacccatct ctgtgtaagg agaaggtggc ttccatattt   900
gacttcaaag cttgccatga tcaagaaacc tgttcttttg atggggttta tcagccaaag   960
attaaagggc atttgtggc ttttgcagga ttctactaca cagccagtgc tttaaatctt   1020
tcaggtagct tttccctgga caccttcaac tccagcacct ggaatttctg ctcacagaat   1080
tggagtcagc tcccactgct gctccccaaa tttgatgagg tatatgcccg ctcttactgc   1140
ttctcagcca actacatcta ccacttgttt gtgaacggtt acaaattcac agaggagact   1200
tggccccaaa tacactttga aaaagaagtg gggaatagca gcatagcctg gtctcttggc   1260
tacatgctca gcctgaccaa ccagatccca gctgaaagcc ctctgatccg tctgcccata   1320
gaaccagata tcggctcgac gagcggcggg tcgacaagtg gtggatctac tagtggctct   1380
ggatccggaa tttgcaagac tgggaatgga aagaactaca gagggacgat gtccaaaaca   1440
aaaaatggca tcacctgtca aaaatggagt tccacttctc cccacagacc tagattctca   1500
cctgctacac ccctcaga gggactggag gagaactact gcaggaatcc agacaacgat   1560 ccgcagggc cctggtgcta tactactgat ccagaaaaga gatatgacta ctgcgacatt   1620
cttgagtgtt ga                                                     1632

<210> SEQ ID NO 98
```

<211> LENGTH: 543
<212> TYPE: PRT
<213> ORGANISM: Artificial Sequence
<220> FEATURE:
<223> OTHER INFORMATION: Linker

<400> SEQUENCE: 98

```
Met Gln Ile His Lys Gln Glu Val Leu Pro Gly Leu Lys Tyr Gly
 1               5                  10                  15
Ile Val Leu Asp Ala Gly Ser Ser Gly Thr Arg Val Tyr Val Tyr Gln
                20                  25                  30
Trp Pro Ala Glu Lys Glu Asn Asn Thr Gly Val Val Ser Gln Thr Phe
            35                  40                  45
Lys Cys Ser Val Lys Gly Ser Gly Ile Ser Ser Tyr Gly Asn Asn Pro
        50                  55                  60
Gln Asp Val Pro Arg Ala Phe Glu Glu Cys Met Gln Lys Val Lys Gly
65                  70                  75                  80
Gln Val Pro Ser His Leu His Gly Ser Thr Pro Ile His Leu Gly Ala
                85                  90                  95
Thr Ala Gly Met Arg Leu Leu Arg Leu Gln Asn Glu Thr Ala Ala Asn
                100                 105                 110
Glu Val Leu Glu Ser Ile Gln Ser Tyr Phe Lys Ser Gln Pro Phe Asp
            115                 120                 125
Phe Arg Gly Ala Gln Ile Ile Ser Gly Gln Glu Glu Gly Val Tyr Gly
        130                 135                 140
Trp Ile Thr Ala Asn Tyr Leu Met Gly Asn Phe Leu Glu Lys Asn Leu
145                 150                 155                 160
Trp His Met Trp Val His Pro His Gly Val Glu Thr Thr Gly Ala Leu
                165                 170                 175
Asp Leu Gly Gly Ala Ser Thr Gln Ile Ser Phe Val Ala Gly Glu Lys
                180                 185                 190
Met Asp Leu Asn Thr Ser Asp Ile Met Gln Val Ser Leu Tyr Gly Tyr
            195                 200                 205
Val Tyr Thr Leu Tyr Thr His Ser Phe Gln Cys Tyr Gly Arg Asn Glu
        210                 215                 220
Ala Glu Lys Lys Phe Leu Ala Met Leu Leu Gln Asn Ser Pro Thr Lys
225                 230                 235                 240
Asn His Leu Thr Asn Pro Cys Tyr Pro Arg Asp Tyr Ser Ile Ser Phe
                245                 250                 255
Thr Met Gly His Val Phe Asp Ser Leu Cys Thr Val Asp Gln Arg Pro
            260                 265                 270
Glu Ser Tyr Asn Pro Asn Asp Val Ile Thr Phe Glu Gly Thr Gly Asp
        275                 280                 285
Pro Ser Leu Cys Lys Glu Lys Val Ala Ser Ile Phe Asp Phe Lys Ala
290                 295                 300
Cys His Asp Gln Glu Thr Cys Ser Phe Asp Gly Val Tyr Gln Pro Lys
305                 310                 315                 320
Ile Lys Gly Pro Phe Val Ala Phe Ala Gly Phe Tyr Tyr Thr Ala Ser
                325                 330                 335
Ala Leu Asn Leu Ser Gly Ser Phe Ser Leu Asp Thr Phe Asn Ser Ser
            340                 345                 350
Thr Trp Asn Phe Cys Ser Gln Asn Trp Ser Gln Leu Pro Leu Leu Leu
        355                 360                 365
Pro Lys Phe Asp Glu Val Tyr Ala Arg Ser Tyr Cys Phe Ser Ala Asn
        370                 375                 380
```

```
Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
            405                 410                 415

Trp Ser Leu Gly Tyr Met Leu Ser Leu Thr Asn Gln Ile Pro Ala Glu
        420                 425                 430

Ser Pro Leu Ile Arg Leu Pro Ile Glu Pro Asp Ile Gly Ser Thr Ser
    435                 440                 445

Gly Gly Ser Thr Ser Gly Gly Ser Thr Ser Gly Ser Gly Ser Gly Ile
        450                 455                 460

Cys Lys Thr Gly Asn Gly Lys Asn Tyr Arg Gly Thr Met Ser Lys Thr
465                 470                 475                 480

Lys Asn Gly Ile Thr Cys Gln Lys Trp Ser Ser Thr Ser Pro His Arg
                485                 490                 495

Pro Arg Phe Ser Pro Ala Thr His Pro Ser Glu Gly Leu Glu Glu Asn
            500                 505                 510

Tyr Cys Arg Asn Pro Asp Asn Asp Pro Gln Gly Pro Trp Cys Tyr Thr
        515                 520                 525

Thr Asp Pro Glu Lys Arg Tyr Asp Tyr Cys Asp Ile Leu Glu Cys
    530                 535                 540
```

<210> SEQ ID NO 99
<211> LENGTH: 36
<212> TYPE: DNA
<213> ORGANISM: Artificial Sequence
<220> FEATURE:
<223> OTHER INFORMATION: Primer

<400> SEQUENCE: 99
aaacccgggt ccatggcccc cacccacaat gcacac        36

<210> SEQ ID NO 100
<211> LENGTH: 36
<212> TYPE: DNA
<213> ORGANISM: Artificial Sequence
<220> FEATURE:
<223> OTHER INFORMATION: Primer

<400> SEQUENCE: 100
aaaaagaatt cttattaaat gaactcgatg ccttcg        36

<210> SEQ ID NO 101
<211> LENGTH: 18
<212> TYPE: DNA
<213> ORGANISM: Artificial Sequence
<220> FEATURE:
<223> OTHER INFORMATION: Primer

<400> SEQUENCE: 101
cccacctggc ggagaagg        18

<210> SEQ ID NO 102
<211> LENGTH: 18
<212> TYPE: DNA
<213> ORGANISM: Artificial Sequence
<220> FEATURE:
<223> OTHER INFORMATION: Primer

<400> SEQUENCE: 102
ggcagcgtgg accacgag        18

<210> SEQ ID NO 103
<211> LENGTH: 18
<212> TYPE: DNA
<213> ORGANISM: Artificial Sequence
<220> FEATURE:
<223> OTHER INFORMATION: Primer

<400> SEQUENCE: 103
ccgacgacca gatcattg                                                 18

<210> SEQ ID NO 104
<211> LENGTH: 18
<212> TYPE: DNA
<213> ORGANISM: Artificial Sequence
<220> FEATURE:
<223> OTHER INFORMATION: Primer

<400> SEQUENCE: 104
caatgatctg gtcgtcgg                                                 18

<210> SEQ ID NO 105
<211> LENGTH: 18
<212> TYPE: DNA
<213> ORGANISM: Artificial Sequence
<220> FEATURE:
<223> OTHER INFORMATION: Primer

<400> SEQUENCE: 105
ctcgtggtcc acgctgcc                                                 18

<210> SEQ ID NO 106
<211> LENGTH: 18
<212> TYPE: DNA
<213> ORGANISM: Artificial Sequence
<220> FEATURE:
<223> OTHER INFORMATION: Primer

<400> SEQUENCE: 106
ccttctccgc caggtggg                                                 18

<210> SEQ ID NO 107
<211> LENGTH: 33
<212> TYPE: DNA
<213> ORGANISM: Artificial Sequence
<220> FEATURE:
<223> OTHER INFORMATION: Primer

<400> SEQUENCE: 107
gggacaaaga ccacggcgtc ctggagtccc acc                                33

<210> SEQ ID NO 108
<211> LENGTH: 33
<212> TYPE: DNA
<213> ORGANISM: Artificial Sequence
<220> FEATURE:
<223> OTHER INFORMATION: Primer

<400> SEQUENCE: 108
ggtgggactc caggacgccg tggtctttgt ccc                                33

<210> SEQ ID NO 109
<211> LENGTH: 33
<212> TYPE: DNA
<213> ORGANISM: Artificial Sequence
<220> FEATURE:
<223> OTHER INFORMATION: Primer

<400> SEQUENCE: 109
ctgtacgtgg gcggctcggg caaggagtgg acg         33

<210> SEQ ID NO 110
<211> LENGTH: 33
<212> TYPE: DNA
<213> ORGANISM: Artificial Sequence
<220> FEATURE:
<223> OTHER INFORMATION: Primer

<400> SEQUENCE: 110
cgtccactcc ttgcccgagc cgcccacgta cag         33

<210> SEQ ID NO 111
<211> LENGTH: 33
<212> TYPE: DNA
<213> ORGANISM: Artificial Sequence
<220> FEATURE:
<223> OTHER INFORMATION: Primer

<400> SEQUENCE: 111
ccgccaggct acctctggca tgagtctgcc tgc         33

<210> SEQ ID NO 112
<211> LENGTH: 33
<212> TYPE: DNA
<213> ORGANISM: Artificial Sequence
<220> FEATURE:
<223> OTHER INFORMATION: Primer

<400> SEQUENCE: 112
gcaggcagac tcatgccaga ggtagcctgg cgg         33

<210> SEQ ID NO 113
<211> LENGTH: 45
<212> TYPE: DNA
<213> ORGANISM: Artificial Sequence
<220> FEATURE:
<223> OTHER INFORMATION: Primer

<400> SEQUENCE: 113
caggagcgct acagctcgaa ggacttcgag cgcaagggcg ccaac         45

<210> SEQ ID NO 114
<211> LENGTH: 45
<212> TYPE: DNA
<213> ORGANISM: Artificial Sequence
<220> FEATURE:
<223> OTHER INFORMATION: Primer

<400> SEQUENCE: 114
gttggcgccc ttgcgctcga agctcttcga gctgtagcgc tcctg         45

<210> SEQ ID NO 115
<211> LENGTH: 58
<212> TYPE: DNA
<213> ORGANISM: Artificial Sequence
<220> FEATURE:
<223> OTHER INFORMATION: Primer

<400> SEQUENCE: 115
cattgtggcc ctcaaatccg tggaggacag cgacagagtc gcctcctaca tcatggcc         58

<210> SEQ ID NO 116

<211> LENGTH: 58
<212> TYPE: DNA
<213> ORGANISM: Artificial Sequence
<220> FEATURE:
<223> OTHER INFORMATION: Primer

<400> SEQUENCE: 116
ggccatgatg taggaggcga ctctgtcgct gtcctccacg gatttgaggg ccacaatg        58

<210> SEQ ID NO 117
<211> LENGTH: 1005
<212> TYPE: DNA
<213> ORGANISM: Homo sapiens

<400> SEQUENCE: 117
atggccccca cccacaatgc acacaactgg aggctcggcc aggcgcccgc caactggtac        60
aatgacacct accccctgtc tcccccacaa aggacaccgg ctgggattcg tatcgaatc       120
gcagttatcg cagacctgga cacagagtca agggcccaag aggaaaacac ctggttcagt       180
tacctgaaaa agggctacct gaccctgtca gacagtgggg acaaggtggc cgtggaatgg       240
gacaaagacc atggggtcct ggagtcccac ctggcggaga aggggagagg catggagcta       300
tccgacctga ttgttttcaa tgggaaactc tactccgtgg atgaccggac ggggggtcgtc      360
taccagatcg aaggcagcaa agccgtgccc tgggtgattc tgtccgacgg cgacggcacc       420
gtggagaaag gcttcaaggc cgaatggctg gcagtgaagg acgagcgtct gtacgtgggc       480
ggcctgggca aggagtggac gaccactacg ggtgatgtgg tgaacgagaa ccccgagtgg       540
gtgaaggtgg tgggctacaa gggcagcgtg gaccacgaga actgggtgtc caactacaac       600
gccctgcggc tgctgccgg catccagccg ccaggctacc tcatccatga gtctgcctgc       660
tggagtgaca cgctgcagcg ctggttcttc ctgccgcgcc gcgccagcca ggagcgctac       720
agcgagaagg acgacgagcg caagggcgcc aacctgctgc tgagcgcctc ccctgacttc       780
ggcgacatcg ctgtgagcca cgtcggggcg gtggtcccca ctcacggctt ctcgtccttc       840
aagttcatcc ccaacaccga cgaccagatc attgtggccc tcaaatccga ggaggacagc       900
ggcagagtcg cctcctacat catggccttc acgctggacg gcgcttcct gttgccggag       960
accaagatcg gaagcgtgaa atacgaaggc atcgagttca tttaa                     1005

<210> SEQ ID NO 118
<211> LENGTH: 334
<212> TYPE: PRT
<213> ORGANISM: Homo sapiens

<400> SEQUENCE: 118

Met Ala Pro Thr His Asn Ala His Asn Trp Arg Leu Gly Gln Ala Pro
  1               5                  10                  15

Ala Asn Trp Tyr Asn Asp Thr Tyr Pro Leu Ser Pro Gln Arg Thr
             20                  25                  30

Pro Ala Gly Ile Arg Tyr Arg Ile Ala Val Ile Ala Asp Leu Asp Thr
             35                  40                  45

Glu Ser Arg Ala Gln Glu Glu Asn Thr Trp Phe Ser Tyr Leu Lys Lys
     50                  55                  60

Gly Tyr Leu Thr Leu Ser Asp Ser Gly Asp Lys Val Ala Val Glu Trp
 65                  70                  75                  80

Asp Lys Asp His Gly Val Leu Glu Ser His Leu Ala Glu Lys Gly Arg
                 85                  90                  95

Gly Met Glu Leu Ser Asp Leu Ile Val Phe Asn Gly Lys Leu Tyr Ser

```
                100                 105                 110
Val Asp Asp Arg Thr Gly Val Val Tyr Gln Ile Glu Gly Ser Lys Ala
            115                 120                 125
Val Pro Trp Val Ile Leu Ser Asp Gly Asp Gly Thr Val Glu Lys Gly
            130                 135                 140
Phe Lys Ala Glu Trp Leu Ala Val Lys Asp Glu Arg Leu Tyr Val Gly
145                 150                 155                 160
Gly Leu Gly Lys Glu Trp Thr Thr Thr Gly Asp Val Val Asn Glu
                165                 170                 175
Asn Pro Glu Trp Val Lys Val Val Gly Tyr Lys Gly Ser Val Asp His
            180                 185                 190
Glu Asn Trp Val Ser Asn Tyr Asn Ala Leu Arg Ala Ala Gly Ile
            195                 200                 205
Gln Pro Pro Gly Tyr Leu Ile His Glu Ser Ala Cys Trp Ser Asp Thr
            210                 215                 220
Leu Gln Arg Trp Phe Phe Leu Pro Arg Arg Ala Ser Gln Glu Arg Tyr
225                 230                 235                 240
Ser Glu Lys Asp Asp Glu Arg Lys Gly Ala Asn Leu Leu Ser Ala
                245                 250                 255
Ser Pro Asp Phe Gly Asp Ile Ala Val Ser His Val Gly Ala Val Val
            260                 265                 270
Pro Thr His Gly Phe Ser Ser Phe Lys Phe Ile Pro Asn Thr Asp Asp
        275                 280                 285
Gln Ile Ile Val Ala Leu Lys Ser Glu Glu Asp Ser Gly Arg Val Ala
    290                 295                 300
Ser Tyr Ile Met Ala Phe Thr Leu Asp Gly Arg Phe Leu Leu Pro Glu
305                 310                 315                 320
Thr Lys Ile Gly Ser Val Lys Tyr Glu Gly Ile Glu Phe Ile
                325                 330

<210> SEQ ID NO 119
<211> LENGTH: 1005
<212> TYPE: DNA
<213> ORGANISM: Homo sapiens

<400> SEQUENCE: 119
atggccccca cccacaatgc acacaactgg aggctcggcc aggcgcccgc caactggtac      60
aatgacacct acccctgtc tccccacaa aggacaccgg ctgggattcg tatcgaatc       120 gcagttatcg cagacctgga cacagagtca agggcccaag aggaaaacac ctggttcagt      180
tacctgaaaa aggctacct gaccctgtca gacagtgggg acaaggtggc cgtggaatgg      240
gacaaagacc acggcgtcct ggagtccac ctggcggaga aggggagagg catggagcta      300
tccgacctga ttgttttcaa tgggaaactc tactccgtgg atgaccggac ggggtcgtc      360 taccagatca aaggcagcaa agccgtgccc tgggtgattc tgtccgacgg cgacggcacc      420
gtggagaaag gcttcaaggc cgaatggctg gcagtgaagg acgagcgtct gtacgtgggc      480
ggcctgggca aggagtggac gaccactacg ggtgatgtgg tgaacgagaa ccccgagtgg      540
gtgaaggtgg tgggctacaa gggcagcgtg gaccacgaga actgggtgtc caactacaac      600
gccctgcggg ctgctgccgg catccagccg ccaggctacc tcatccatga gtctgcctgc      660
tggagtgaca cgctgcagcg ctggttcttc ctgccgcgcc gcgccagcca ggagcgctac      720
agcgagaagg acgacgagcg caagggcgcc aacctgctgc tgagcgcctc ccctgacttc      780
ggcgacatcg ctgtgagcca cgtcggggcg gtggtcccca ctcacggctt ctcgtccttc      840
```

```
aagttcatcc ccaacaccga cgaccagatc attgtggccc tcaaatccga ggaggacagc      900
ggcagagtcg cctcctacat catggccttc acgctggacg gcgcttcct gttgccggag      960 accaagatcg aagcgtgaa atacgaaggc atcgagttca tttaa                     1005
```

<210> SEQ ID NO 120
<211> LENGTH: 334
<212> TYPE: PRT
<213> ORGANISM: Homo sapiens

<400> SEQUENCE: 120

```
Met Ala Pro Thr His Asn Ala His Asn Trp Arg Leu Gly Gln Ala Pro
1               5                   10                  15

Ala Asn Trp Tyr Asn Asp Thr Tyr Pro Leu Ser Pro Pro Gln Arg Thr
            20                  25                  30

Pro Ala Gly Ile Arg Tyr Arg Ile Ala Val Ile Ala Asp Leu Asp Thr
        35                  40                  45

Glu Ser Arg Ala Gln Glu Glu Asn Thr Trp Phe Ser Tyr Leu Lys Lys
    50                  55                  60

Gly Tyr Leu Thr Leu Ser Asp Ser Gly Asp Lys Val Ala Val Glu Trp
65                  70                  75                  80

Asp Lys Asp His Gly Val Leu Glu Ser His Leu Ala Glu Lys Gly Arg
                85                  90                  95

Gly Met Glu Leu Ser Asp Leu Ile Val Phe Asn Gly Lys Leu Tyr Ser
            100                 105                 110

Val Asp Asp Arg Thr Gly Val Val Tyr Gln Ile Glu Gly Ser Lys Ala
        115                 120                 125

Val Pro Trp Val Ile Leu Ser Asp Gly Asp Gly Thr Val Glu Lys Gly
    130                 135                 140

Phe Lys Ala Glu Trp Leu Ala Val Lys Asp Glu Arg Leu Tyr Val Gly
145                 150                 155                 160

Gly Leu Gly Lys Glu Trp Thr Thr Thr Gly Asp Val Val Asn Glu
                165                 170                 175

Asn Pro Glu Trp Val Lys Val Val Gly Tyr Lys Gly Ser Val Asp His
            180                 185                 190

Glu Asn Trp Val Ser Asn Tyr Asn Ala Leu Arg Ala Ala Gly Ile
        195                 200                 205

Gln Pro Pro Gly Tyr Leu Ile His Glu Ser Ala Cys Trp Ser Asp Thr
    210                 215                 220

Leu Gln Arg Trp Phe Phe Leu Pro Arg Arg Ala Ser Gln Glu Arg Tyr
225                 230                 235                 240

Ser Glu Lys Asp Asp Glu Arg Lys Gly Ala Asn Leu Leu Leu Ser Ala
                245                 250                 255

Ser Pro Asp Phe Gly Asp Ile Ala Val Ser His Val Gly Ala Val Val
            260                 265                 270

Pro Thr His Gly Phe Ser Ser Phe Lys Phe Ile Pro Asn Thr Asp Asp
        275                 280                 285

Gln Ile Ile Val Ala Leu Lys Ser Glu Glu Asp Ser Gly Arg Val Ala
    290                 295                 300

Ser Tyr Ile Met Ala Phe Thr Leu Asp Gly Arg Phe Leu Leu Pro Glu
305                 310                 315                 320

Thr Lys Ile Gly Ser Val Lys Tyr Glu Gly Ile Glu Phe Ile
                325                 330
```

<210> SEQ ID NO 121
<211> LENGTH: 1005
<212> TYPE: DNA
<213> ORGANISM: Homo sapiens

<400> SEQUENCE: 121

```
atggccccca cccacaatgc acacaactgg aggctcggcc aggcgcccgc caactggtac      60
aatgacacct acccctgtc tccccacaa aggacaccgg ctgggattcg gtatcgaatc      120
gcagttatcg cagacctgga cacagagtca agggcccaag aggaaaacac ctggttcagt    180
tacctgaaaa agggctacct gaccctgtca gacagtgggg acaaggtggc cgtggaatgg    240
gacaaagacc acggcgtcct ggagtcccac ctggcggaga aggggagagg catggagcta    300
tccgacctga ttgttttcaa tgggaaactc tactccgtgg atgaccggac ggggctcgtc    360
taccagatcg aaggcagcaa agccgtgccc tgggtgattc tgtccgacgg cgacggcacc    420
gtggagaaag gcttcaaggc cgaatggctg cagtgaagg acgagcgtct gtacgtgggc    480
ggctcgggca aggagtggac gaccactacg ggtgatgtgg tgaacgagaa ccccgagtgg    540
gtgaaggtgg tgggctacaa gggcagcgtg accacgagaa actgggtgtc caactacaac    600
gccctgcggg ctgctgccgg catccagccg ccaggctacc tcatccatga gtctgcctgc    660
tggagtgaca cgctgcagcg ctggttcttc ctgccgcgcc gcgccagcca ggagcgctac    720
agcgagaagg acgacgagcg caagggcgcc aacctgctgc tgagcgcctc ccctgacttc    780
ggcgacatcg ctgtgagcca cgtcggggcg gtggtcccca ctcacggctt ctcgtccttc    840
aagttcatcc ccaacaccga cgaccagatc attgtggccc tcaaatccga ggaggacagc    900
ggcagagtcg cctcctacat catggccttc acgctggacg ggcgcttcct gttgccggag    960
accaagatcg gaagcgtgaa atacgaaggc atcgagttca tttaa                    1005
```

<210> SEQ ID NO 122
<211> LENGTH: 334
<212> TYPE: PRT
<213> ORGANISM: Homo sapiens

<400> SEQUENCE: 122

Met Ala Pro Thr His Asn Ala His Asn Trp Arg Leu Gly Gln Ala Pro
1               5                   10                  15

Ala Asn Trp Tyr Asn Asp Thr Tyr Pro Leu Ser Pro Gln Arg Thr
            20                  25                  30

Pro Ala Gly Ile Arg Tyr Arg Ile Ala Val Ile Ala Asp Leu Asp Thr
        35                  40                  45

Glu Ser Arg Ala Gln Glu Glu Asn Thr Trp Phe Ser Tyr Leu Lys Lys
    50                  55                  60

Gly Tyr Leu Thr Leu Ser Asp Ser Gly Asp Lys Val Ala Val Glu Trp
65                  70                  75                  80

Asp Lys Asp His Gly Val Leu Glu Ser His Leu Ala Glu Lys Gly Arg
                85                  90                  95

Gly Met Glu Leu Ser Asp Leu Ile Val Phe Asn Gly Lys Leu Tyr Ser
            100                 105                 110

Val Asp Asp Arg Thr Gly Val Val Tyr Gln Ile Glu Gly Ser Lys Ala
        115                 120                 125

Val Pro Trp Val Ile Leu Ser Asp Gly Asp Gly Thr Val Glu Lys Gly
    130                 135                 140

Phe Lys Ala Glu Trp Leu Ala Val Lys Asp Glu Arg Leu Tyr Val Gly
145                 150                 155                 160

```
Gly Ser Gly Lys Glu Trp Thr Thr Thr Gly Asp Val Val Asn Glu
            165                 170                 175

Asn Pro Glu Trp Val Lys Val Val Gly Tyr Lys Gly Ser Val Asp His
        180                 185                 190

Glu Asn Trp Val Ser Asn Tyr Asn Ala Leu Arg Ala Ala Ala Gly Ile
    195                 200                 205

Gln Pro Pro Gly Tyr Leu Ile His Glu Ser Ala Cys Trp Ser Asp Thr
210                 215                 220

Leu Gln Arg Trp Phe Phe Leu Pro Arg Arg Ala Ser Gln Glu Arg Tyr
225                 230                 235                 240

Ser Glu Lys Asp Asp Glu Arg Lys Gly Ala Asn Leu Leu Leu Ser Ala
                245                 250                 255

Ser Pro Asp Phe Gly Asp Ile Ala Val Ser His Val Gly Ala Val Val
            260                 265                 270

Pro Thr His Gly Phe Ser Ser Phe Lys Phe Ile Pro Asn Thr Asp Asp
        275                 280                 285

Gln Ile Ile Val Ala Leu Lys Ser Glu Glu Asp Ser Gly Arg Val Ala
    290                 295                 300

Ser Tyr Ile Met Ala Phe Thr Leu Asp Gly Arg Phe Leu Leu Pro Glu
305                 310                 315                 320

Thr Lys Ile Gly Ser Val Lys Tyr Glu Gly Ile Glu Phe Ile
                325                 330

<210> SEQ ID NO 123
<211> LENGTH: 1005
<212> TYPE: DNA
<213> ORGANISM: Homo sapiens

<400> SEQUENCE: 123
atggccccca cccacaatgc acacaactgg aggctcggcc aggcgcccgc caactggtac      60
aatgacacct accccctgtc tcccccacaa aggacaccgg ctgggattcg gtatcgaatc     120
gcagttatcg cagacctgga cacagagtca agggcccaag aggaaaacac ctggttcagt     180
tacctgaaaa agggctacct gaccctgtca gacagtgggg acaaggtggc cgtggaatgg     240
gacaaagacc atggggtcct ggagtcccac ctggcggaga aggggagagg catggagcta     300
tccgacctga ttgttttcaa tgggaaactc tactccgtgg atgaccggac ggggtcgtc      360
taccagatcg aaggcagcaa agccgtgccc tgggtgattc tgtccgacgg cgacggcacc     420
gtggagaaag gcttcaaggc cgaatggctg cagtgaagg acgagcgtct gtacgtgggc     480
ggcctgggca aggagtggac gaccactacg ggtgatgtgg tgaacgagaa ccccgagtgg     540
gtgaaggtgg tgggctacaa gggcagcgtg gaccacgaga ctgggtgtc caactacaac     600
gccctgcggg ctgctgccgg catccagccg ccaggctacc tctggcatga gtctgcctgc     660
tggagtgaca cgctgcagcg ctggttcttc ctgccgcgcc cgccagcca ggagcgctac      720
agcgagaagg acgacgagcg caagggcgcc aacctgctgc tgagcgcctc ccctgacttc     780
ggcgacatcg ctgtgagcca cgtcggggcg gtggtcccca ctcacggctt ctcgtccttc     840
aagttcatcc ccaacaccga cgaccagatc attgtggccc tcaaatccga ggaggacagc     900
ggcagagtcg cctcctacat catggccttc acgctggacg gcgcttcct gttgccggag     960
accaagatcg gaagcgtgaa atacgaaggc atcgagttca tttaa                    1005

<210> SEQ ID NO 124
<211> LENGTH: 334
<212> TYPE: PRT
```

<213> ORGANISM: Homo sapiens

<400> SEQUENCE: 124

| Met | Ala | Pro | Thr | His | Asn | Ala | His | Asn | Trp | Arg | Leu | Gly | Gln | Ala | Pro |
|---|---|---|---|---|---|---|---|---|---|---|---|---|---|---|---|
| 1 | | | | 5 | | | | | 10 | | | | | 15 | |

| Ala | Asn | Trp | Tyr | Asn | Asp | Thr | Tyr | Pro | Leu | Ser | Pro | Pro | Gln | Arg | Thr |
|---|---|---|---|---|---|---|---|---|---|---|---|---|---|---|---|
| | | | 20 | | | | | 25 | | | | | 30 | | |

| Pro | Ala | Gly | Ile | Arg | Tyr | Arg | Ile | Ala | Val | Ile | Ala | Asp | Leu | Asp | Thr |
|---|---|---|---|---|---|---|---|---|---|---|---|---|---|---|---|
| | | | 35 | | | | | 40 | | | | | 45 | | |

| Glu | Ser | Arg | Ala | Gln | Glu | Glu | Asn | Thr | Trp | Phe | Ser | Tyr | Leu | Lys | Lys |
|---|---|---|---|---|---|---|---|---|---|---|---|---|---|---|---|
| | 50 | | | | | 55 | | | | | 60 | | | | |

| Gly | Tyr | Leu | Thr | Leu | Ser | Asp | Ser | Gly | Asp | Lys | Val | Ala | Val | Glu | Trp |
|---|---|---|---|---|---|---|---|---|---|---|---|---|---|---|---|
| 65 | | | | | 70 | | | | | 75 | | | | | 80 |

| Asp | Lys | Asp | His | Gly | Val | Leu | Glu | Ser | His | Leu | Ala | Glu | Lys | Gly | Arg |
|---|---|---|---|---|---|---|---|---|---|---|---|---|---|---|---|
| | | | | 85 | | | | | 90 | | | | | 95 | |

| Gly | Met | Glu | Leu | Ser | Asp | Leu | Ile | Val | Phe | Asn | Gly | Lys | Leu | Tyr | Ser |
|---|---|---|---|---|---|---|---|---|---|---|---|---|---|---|---|
| | | | 100 | | | | | 105 | | | | | 110 | | |

| Val | Asp | Asp | Arg | Thr | Gly | Val | Val | Tyr | Gln | Ile | Glu | Gly | Ser | Lys | Ala |
|---|---|---|---|---|---|---|---|---|---|---|---|---|---|---|---|
| | | 115 | | | | | 120 | | | | | 125 | | | |

| Val | Pro | Trp | Val | Ile | Leu | Ser | Asp | Gly | Asp | Gly | Thr | Val | Glu | Lys | Gly |
|---|---|---|---|---|---|---|---|---|---|---|---|---|---|---|---|
| | 130 | | | | | 135 | | | | | 140 | | | | |

| Phe | Lys | Ala | Glu | Trp | Leu | Ala | Val | Lys | Asp | Glu | Arg | Leu | Tyr | Val | Gly |
|---|---|---|---|---|---|---|---|---|---|---|---|---|---|---|---|
| 145 | | | | | 150 | | | | | 155 | | | | | 160 |

| Gly | Leu | Gly | Lys | Glu | Trp | Thr | Thr | Thr | Gly | Asp | Val | Val | Asn | Glu |
|---|---|---|---|---|---|---|---|---|---|---|---|---|---|---|
| | | | | 165 | | | | | 170 | | | | | 175 |

| Asn | Pro | Glu | Trp | Val | Lys | Val | Gly | Tyr | Lys | Gly | Ser | Val | Asp | His |
|---|---|---|---|---|---|---|---|---|---|---|---|---|---|---|
| | | | 180 | | | | | 185 | | | | | 190 | |

| Glu | Asn | Trp | Val | Ser | Asn | Tyr | Asn | Ala | Leu | Arg | Ala | Ala | Ala | Gly | Ile |
|---|---|---|---|---|---|---|---|---|---|---|---|---|---|---|---|
| | | 195 | | | | | 200 | | | | | 205 | | | |

| Gln | Pro | Pro | Gly | Tyr | Leu | Trp | His | Glu | Ser | Ala | Cys | Trp | Ser | Asp | Thr |
|---|---|---|---|---|---|---|---|---|---|---|---|---|---|---|---|
| | 210 | | | | | 215 | | | | | 220 | | | | |

| Leu | Gln | Arg | Trp | Phe | Phe | Leu | Pro | Arg | Arg | Ala | Ser | Gln | Glu | Arg | Tyr |
|---|---|---|---|---|---|---|---|---|---|---|---|---|---|---|---|
| 225 | | | | | 230 | | | | | 235 | | | | | 240 |

| Ser | Glu | Lys | Asp | Asp | Glu | Arg | Lys | Gly | Ala | Asn | Leu | Leu | Leu | Ser | Ala |
|---|---|---|---|---|---|---|---|---|---|---|---|---|---|---|---|
| | | | 245 | | | | | 250 | | | | | 255 | | |

| Ser | Pro | Asp | Phe | Gly | Asp | Ile | Ala | Val | Ser | His | Val | Gly | Ala | Val | Val |
|---|---|---|---|---|---|---|---|---|---|---|---|---|---|---|---|
| | | | 260 | | | | | 265 | | | | | 270 | | |

| Pro | Thr | His | Gly | Phe | Ser | Ser | Phe | Lys | Phe | Ile | Pro | Asn | Thr | Asp | Asp |
|---|---|---|---|---|---|---|---|---|---|---|---|---|---|---|---|
| | | 275 | | | | | 280 | | | | | 285 | | | |

| Gln | Ile | Ile | Val | Ala | Leu | Lys | Ser | Glu | Glu | Asp | Ser | Gly | Arg | Val | Ala |
|---|---|---|---|---|---|---|---|---|---|---|---|---|---|---|---|
| | 290 | | | | | 295 | | | | | 300 | | | | |

| Ser | Tyr | Ile | Met | Ala | Phe | Thr | Leu | Asp | Gly | Arg | Phe | Leu | Leu | Pro | Glu |
|---|---|---|---|---|---|---|---|---|---|---|---|---|---|---|---|
| 305 | | | | | 310 | | | | | 315 | | | | | 320 |

| Thr | Lys | Ile | Gly | Ser | Val | Lys | Tyr | Glu | Gly | Ile | Glu | Phe | Ile |
|---|---|---|---|---|---|---|---|---|---|---|---|---|---|
| | | | | 325 | | | | | 330 | | | | |

<210> SEQ ID NO 125
<211> LENGTH: 1005
<212> TYPE: DNA
<213> ORGANISM: Homo sapiens

<400> SEQUENCE: 125
atggccccca cccacaatgc acacaactgg aggctcggcc aggcgcccgc caactggtac    60
aatgacacct accccctgtc tccccacaa aggacaccgg ctgggattcg gtatcgaatc   120

-continued

```
gcagttatcg cagacctgga cacagagtca agggcccaag aggaaaacac ctggttcagt      180
tacctgaaaa agggctacct gaccctgtca gacagtgggg acaaggtggc cgtggaatgg      240
gacaaagacc atggggtcct ggagtcccac ctggcggaga aggggagagg catggagcta      300
tccgacctga ttgttttcaa tgggaaactc tactccgtgg atgaccggac ggggtcgtc       360 taccagatcg aaggcagcaa agccgtgccc tgggtgattc tgtccgacgg cgacggcacc      420
gtggagaaag gcttcaaggc cgaatggctg gcagtgaagg acgagcgtct gtacgtgggc      480
ggcctgggca aggagtggac gaccactacg ggtgatgtgg tgaacgagaa ccccgagtgg      540
gtgaaggtgg tgggctacaa gggcagcgtg gaccacgaga ctgggtgtc caactacaac       600 gccctgcggg ctgctgccgg catccagccg ccaggctacc tcatccatga gtctgcctgc      660
tggagtgaca cgctgcagcg ctggttcttc ctgccgcgcc gcgccagcca ggagcgctac      720
agctcgaagg acttcgagcg caagggcgcc aacctgctgc tgagcgcctc ccctgacttc      780
ggcgacatcg ctgtgagcca cgtcggggcg gtggtcccca ctcacggctt ctcgtccttc      840
aagttcatcc ccaacaccga cgaccagatc attgtggccc tcaaatccga ggaggacagc      900
ggcagagtcg cctcctacat catggccttc acgctggacg gcgcttcct gttgccggag      960 accaagatcg gaagcgtgaa atacgaaggc atcgagttca tttaa                    1005
```

<210> SEQ ID NO 126
<211> LENGTH: 334
<212> TYPE: PRT
<213> ORGANISM: Homo sapiens

<400> SEQUENCE: 126

```
Met Ala Pro Thr His Asn Ala His Asn Trp Arg Leu Gly Gln Ala Pro
 1               5                  10                  15

Ala Asn Trp Tyr Asn Asp Thr Tyr Pro Leu Ser Pro Pro Gln Arg Thr
            20                  25                  30

Pro Ala Gly Ile Arg Tyr Arg Ile Ala Val Ile Ala Asp Leu Asp Thr
        35                  40                  45

Glu Ser Arg Ala Gln Glu Glu Asn Thr Trp Phe Ser Tyr Leu Lys Lys
    50                  55                  60

Gly Tyr Leu Thr Leu Ser Asp Ser Gly Asp Lys Val Ala Val Glu Trp
65                  70                  75                  80

Asp Lys Asp His Gly Val Leu Glu Ser His Leu Ala Glu Lys Gly Arg
                85                  90                  95

Gly Met Glu Leu Ser Asp Leu Ile Val Phe Asn Gly Lys Leu Tyr Ser
            100                 105                 110

Val Asp Asp Arg Thr Gly Val Val Tyr Gln Ile Glu Gly Ser Lys Ala
        115                 120                 125

Val Pro Trp Val Ile Leu Ser Asp Gly Asp Gly Thr Val Glu Lys Gly
    130                 135                 140

Phe Lys Ala Glu Trp Leu Ala Val Lys Asp Glu Arg Leu Tyr Val Gly
145                 150                 155                 160

Gly Leu Gly Lys Glu Trp Thr Thr Thr Thr Gly Asp Val Val Asn Glu
                165                 170                 175

Asn Pro Glu Trp Val Lys Val Val Gly Tyr Lys Gly Ser Val Asp His
            180                 185                 190

Glu Asn Trp Val Ser Asn Tyr Asn Ala Leu Arg Ala Ala Ala Gly Ile
        195                 200                 205

Gln Pro Pro Gly Tyr Leu Ile His Glu Ser Ala Cys Trp Ser Asp Thr
    210                 215                 220
```

```
Leu Gln Arg Trp Phe Phe Leu Pro Arg Arg Ala Ser Gln Glu Arg Tyr
225                 230                 235                 240

Ser Ser Lys Asp Phe Glu Arg Lys Gly Ala Asn Leu Leu Ser Ala
            245                 250                 255

Ser Pro Asp Phe Gly Asp Ile Ala Val Ser His Val Gly Ala Val Val
            260                 265                 270

Pro Thr His Gly Phe Ser Ser Phe Lys Phe Ile Pro Asn Thr Asp Asp
            275                 280                 285

Gln Ile Ile Val Ala Leu Lys Ser Glu Glu Asp Ser Gly Arg Val Ala
            290                 295                 300

Ser Tyr Ile Met Ala Phe Thr Leu Asp Gly Arg Phe Leu Leu Pro Glu
305                 310                 315                 320

Thr Lys Ile Gly Ser Val Lys Tyr Glu Gly Ile Glu Phe Ile
                325                 330

<210> SEQ ID NO 127
<211> LENGTH: 1005
<212> TYPE: DNA
<213> ORGANISM: Homo sapiens

<400> SEQUENCE: 127
atggccccca cccacaatgc acacaactgg aggctcggcc aggcgcccgc caactggtac      60
aatgacacct accccctgtc tccccacaa aggacaccgg ctgggattcg gtatcgaatc     120
gcagttatcg cagacctgga cacagagtca agggcccaag aggaaaacac ctggttcagt     180
tacctgaaaa agggctacct gaccctgtca gacagtgggg acaaggtggc cgtggaatgg     240
gacaaagacc atggggtcct ggagtccac ctggcggaga aggggagagg catggagcta     300
tccgacctga ttgttttcaa tgggaaactc tactccgtgg atgaccggac ggggtcgtc     360
taccagatcg aaggcagcaa agccgtgccc tgggtgattc tgtccgacgg cgacggcacc     420
gtggagaaag gcttcaaggc cgaatggctg gcagtgaagg acgagcgtct gtacgtgggc     480
ggcctgggca aggagtggac gaccactacg ggtgatgtgg tgaacgagaa ccccgagtgg     540
gtgaaggtgg tgggctacaa gggcagcgtg gaccacgaga actgggtgtc caactacaac     600
gccctgcggg ctgctgccgg catccagccg ccaggctacc tcatccatga gtctgcctgc     660
tggagtgaca cgctgcagcg ctggttcttc ctgccgcgcc gcgccagcca ggagcgctac     720
agcgagaagg acgacgagcg caagggcgcc aacctgctgc tgagcgcctc ccctgacttc     780
ggcgacatcg ctgtgagcca cgtcggggcg gtggtcccca ctcacggctt ctcgtccttc     840
aagttcatcc ccaacaccga cgaccagatc attgtggccc tcaaatccgt ggaggacagc     900
gacagagtcg cctcctacat catggccttc acgctggacg gcgcttcct gttgccggag     960
accaagatcg aagcgtgaa atacgaaggc atcgagttca tttaa                    1005

<210> SEQ ID NO 128
<211> LENGTH: 334
<212> TYPE: PRT
<213> ORGANISM: Homo sapiens

<400> SEQUENCE: 128

Met Ala Pro Thr His Asn Ala His Asn Trp Arg Leu Gly Gln Ala Pro
1               5                   10                  15

Ala Asn Trp Tyr Asn Asp Thr Tyr Pro Leu Ser Pro Pro Gln Arg Thr
            20                  25                  30

Pro Ala Gly Ile Arg Tyr Arg Ile Ala Val Ile Ala Asp Leu Asp Thr
```

-continued

```
                35                  40                  45
Glu Ser Arg Ala Gln Glu Glu Asn Thr Trp Phe Ser Tyr Leu Lys Lys
 50                  55                  60

Gly Tyr Leu Thr Leu Ser Asp Ser Gly Asp Lys Val Ala Val Glu Trp
 65                  70                  75                  80

Asp Lys Asp His Gly Val Leu Glu Ser His Leu Ala Glu Lys Gly Arg
                 85                  90                  95

Gly Met Glu Leu Ser Asp Leu Ile Val Phe Asn Gly Lys Leu Tyr Ser
            100                 105                 110

Val Asp Asp Arg Thr Gly Val Val Tyr Gln Ile Glu Gly Ser Lys Ala
            115                 120                 125

Val Pro Trp Val Ile Leu Ser Asp Gly Asp Thr Val Glu Lys Gly
130                 135                 140

Phe Lys Ala Glu Trp Leu Ala Val Lys Asp Glu Arg Leu Tyr Val Gly
145                 150                 155                 160

Gly Leu Gly Lys Glu Trp Thr Thr Thr Gly Asp Val Val Asn Glu
                165                 170                 175

Asn Pro Glu Trp Val Lys Val Gly Tyr Lys Gly Ser Val Asp His
            180                 185                 190

Glu Asn Trp Val Ser Asn Tyr Asn Ala Leu Arg Ala Ala Gly Ile
            195                 200                 205

Gln Pro Pro Gly Tyr Leu Ile His Glu Ser Ala Cys Trp Ser Asp Thr
            210                 215                 220

Leu Gln Arg Trp Phe Phe Leu Pro Arg Arg Ala Ser Gln Glu Arg Tyr
225                 230                 235                 240

Ser Glu Lys Asp Asp Glu Arg Lys Gly Ala Asn Leu Leu Ser Ala
                245                 250                 255

Ser Pro Asp Phe Gly Asp Ile Ala Val Ser His Val Gly Ala Val Val
                260                 265                 270

Pro Thr His Gly Phe Ser Ser Phe Lys Phe Ile Pro Asn Thr Asp Asp
            275                 280                 285

Gln Ile Ile Val Ala Leu Lys Ser Val Glu Asp Ser Asp Arg Val Ala
290                 295                 300

Ser Tyr Ile Met Ala Phe Thr Leu Asp Gly Arg Phe Leu Leu Pro Glu
305                 310                 315                 320

Thr Lys Ile Gly Ser Val Lys Tyr Glu Gly Ile Glu Phe Ile
                325                 330
```

<210> SEQ ID NO 129
<211> LENGTH: 37
<212> TYPE: DNA
<213> ORGANISM: Artificial Sequence
<220> FEATURE:
<223> OTHER INFORMATION: Primer

<400> SEQUENCE: 129
aaaacccggg atggctgtct cccacaggaa ccagcag    37

<210> SEQ ID NO 130
<211> LENGTH: 35
<212> TYPE: DNA
<213> ORGANISM: Artificial Sequence
<220> FEATURE:
<223> OTHER INFORMATION: Primer

<400> SEQUENCE: 130
aaaacccggg ctatcaatgg gagatgccca gagac    35

<210> SEQ ID NO 131
<211> LENGTH: 17
<212> TYPE: DNA
<213> ORGANISM: Artificial Sequence
<220> FEATURE:
<223> OTHER INFORMATION: Primer

<400> SEQUENCE: 131
gatgcaggga gcactgg                                              17

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
gcaggactac gcttactgcc                                           20

<210> SEQ ID NO 133
<211> LENGTH: 18
<212> TYPE: DNA
<213> ORGANISM: Artificial Sequence
<220> FEATURE:
<223> OTHER INFORMATION: Primer

<400> SEQUENCE: 133
cccaaatcac gttcctgc                                             18

<210> SEQ ID NO 134
<211> LENGTH: 18
<212> TYPE: DNA
<213> ORGANISM: Artificial Sequence
<220> FEATURE:
<223> OTHER INFORMATION: Primer

<400> SEQUENCE: 134
ctgatgggca cactttcc                                             18

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
ctcttactat tatgaccgag                                           20

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
ctcggtcata atagtaagag                                           20

<210> SEQ ID NO 137
<211> LENGTH: 18
<212> TYPE: DNA
<213> ORGANISM: Artificial Sequence
<220> FEATURE:

```
<223> OTHER INFORMATION: Primer

<400> SEQUENCE: 137
ggaaagtgtg cccatcag                                                   18

<210> SEQ ID NO 138
<211> LENGTH: 19
<212> TYPE: DNA
<213> ORGANISM: Artificial Sequence
<220> FEATURE:
<223> OTHER INFORMATION: Primer

<400> SEQUENCE: 138
ggaggctccc cctaggtcc                                                  19

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
ggcagtaagc gtagtcctgc                                                 20

<210> SEQ ID NO 140
<211> LENGTH: 17
<212> TYPE: DNA
<213> ORGANISM: Artificial Sequence
<220> FEATURE:
<223> OTHER INFORMATION: Primer

<400> SEQUENCE: 140
ccagtgctcc ctgcatc                                                    17

<210> SEQ ID NO 141
<211> LENGTH: 1233
<212> TYPE: DNA
<213> ORGANISM: Homo sapiens

<400> SEQUENCE: 141
atggctgtct cccacaggaa ccagcagact tggtttgagg gtatcttcct gtcttccatg      60
tgccccatca atgtcagcgc cagcaccttg tatggaatta tgtttgatgc agggagcact     120
ggaactcgaa ttcatgttta caccttttgt cagaaaatgc caggacagct tccaattcta     180
gaaggggaag ttttttgattc tgtgaagcca ggactttctg cttttgtaga tcaacctaag     240
cagggtgctg agaccgttca agggctctta gaggtggcca aagactcaat ccccgaagt      300
cactggaaaa agaccccagt ggtcctaaag gcaacagcag gactacgctt actgccagaa     360
cacaaagcca aggctctgct ctttgaggta aggagatct tcaggaagtc acctttcctg      420
gtaccaaagg gcagtgttag catcatggat ggatccgacg aaggcatatt agcttgggtt     480
actgtgaatt ttctgacagg tcagctgcat ggccacagac aggagactgt ggggaccttg     540
gacctagggg gagcctccac ccaaatcacg ttcctgcccc agtttgagaa aactctggaa     600
caaactccta gggctacct cacttccttt gagatgttta acagcactta taagctctat     660
acacatagtt acttgggatt tggattgaaa gctgcaagac tagcaaccct gggagccctg     720
gagacagaag ggactgatgg gcacactttc cggagtgcct gtttaccgag atggttggaa     780
gcagagtgga tctttggggg tgtgaaatac cagtatggtg caaccaaga aggggaggtg     840
ggctttgagc cctgctatgc cgaagtgctg aggtggtac gaggaaaact tcaccagcca     900
```

```
gaggaggtcc agagaggttc cttctatgct ttctcttact attatgaccg agctgttgac      960
acagacatga ttgattatga aaaggggggt attttaaaag ttgaagattt tgaaagaaaa     1020 gccaggggaag tgtgtgataa cttggaaaac ttcacctcag gcagtccttt cctgtgcatg    1080
gatctcagct acatcacagc cctgttaaag gatggctttg gctttgcaga cagcacagtc    1140
ttacagctca caaagaaagt gaacaacata gagacgggct gggccttggg ggccacctt    1200 cacctgttgc agtctctggg catctcccat tga                                  1233
```

<210> SEQ ID NO 142
<211> LENGTH: 410
<212> TYPE: PRT
<213> ORGANISM: Homo sapiens

<400> SEQUENCE: 142

```
Met Ala Val Ser His Arg Asn Gln Gln Thr Trp Phe Glu Gly Ile Phe
  1               5                  10                  15

Leu Ser Ser Met Cys Pro Ile Asn Val Ser Ala Ser Thr Leu Tyr Gly
                 20                  25                  30

Ile Met Phe Asp Ala Gly Ser Thr Gly Thr Arg Ile His Val Tyr Thr
             35                  40                  45

Phe Val Gln Lys Met Pro Gly Gln Leu Pro Ile Leu Glu Gly Glu Val
         50                  55                  60

Phe Asp Ser Val Lys Pro Gly Leu Ser Ala Phe Val Asp Gln Pro Lys
     65                  70                  75                  80

Gln Gly Ala Glu Thr Val Gln Gly Leu Leu Val Ala Lys Asp Ser
                 85                  90                  95

Ile Pro Arg Ser His Trp Lys Lys Thr Pro Val Val Leu Lys Ala Thr
            100                 105                 110

Ala Gly Leu Arg Leu Leu Pro Glu His Lys Ala Lys Ala Leu Leu Phe
        115                 120                 125

Glu Val Lys Glu Ile Phe Arg Lys Ser Pro Phe Leu Val Pro Lys Gly
    130                 135                 140

Ser Val Ser Ile Met Asp Gly Ser Asp Glu Gly Ile Leu Ala Trp Val
145                 150                 155                 160

Thr Val Asn Phe Leu Thr Gly Gln Leu His Gly His Arg Gln Glu Thr
                165                 170                 175

Val Gly Thr Leu Asp Leu Gly Gly Ala Ser Thr Gln Ile Thr Phe Leu
            180                 185                 190

Pro Gln Phe Glu Lys Thr Leu Glu Gln Thr Pro Arg Gly Tyr Leu Thr
        195                 200                 205

Ser Phe Glu Met Phe Asn Ser Thr Tyr Lys Leu Tyr Thr His Ser Tyr
    210                 215                 220

Leu Gly Phe Gly Leu Lys Ala Ala Arg Leu Ala Thr Leu Gly Ala Leu
225                 230                 235                 240

Glu Thr Glu Gly Thr Asp Gly His Thr Phe Arg Ser Ala Cys Leu Pro
                245                 250                 255

Arg Trp Leu Glu Ala Glu Trp Ile Phe Gly Gly Val Lys Tyr Gln Tyr
            260                 265                 270

Gly Gly Asn Gln Glu Gly Glu Val Gly Phe Glu Pro Cys Tyr Ala Glu
        275                 280                 285

Val Leu Arg Val Val Arg Gly Lys Leu His Gln Pro Glu Glu Val Gln
    290                 295                 300

Arg Gly Ser Phe Tyr Ala Phe Ser Tyr Tyr Tyr Asp Arg Ala Val Asp
```

```
                305                 310                 315                 320
Thr Asp Met Ile Asp Tyr Glu Lys Gly Gly Ile Leu Lys Val Glu Asp
                    325                 330                 335

Phe Glu Arg Lys Ala Arg Glu Val Cys Asp Asn Leu Glu Asn Phe Thr
                340                 345                 350

Ser Gly Ser Pro Phe Leu Cys Met Asp Leu Ser Tyr Ile Thr Ala Leu
            355                 360                 365

Leu Lys Asp Gly Phe Gly Phe Ala Asp Ser Thr Val Leu Gln Leu Thr
        370                 375                 380

Lys Lys Val Asn Asn Ile Glu Thr Gly Trp Ala Leu Gly Ala Thr Phe
385                 390                 395                 400

His Leu Leu Gln Ser Leu Gly Ile Ser His
                405                 410

<210> SEQ ID NO 143
<211> LENGTH: 15
<212> TYPE: PRT
<213> ORGANISM: Oryctolagus cuniculus

<400> SEQUENCE: 143

Leu Val Cys Asp Asn Gly Ser Gly Leu Val Lys Ala Gly Phe Ala
1               5                   10                  15

<210> SEQ ID NO 144
<211> LENGTH: 15
<212> TYPE: PRT
<213> ORGANISM: Homo sapiens

<400> SEQUENCE: 144

Gly Ile Val Leu Asp Ser Gly Asp Gly Val Thr His Asn Val Pro
1               5                   10                  15

<210> SEQ ID NO 145
<211> LENGTH: 15
<212> TYPE: PRT
<213> ORGANISM: Homo sapiens

<400> SEQUENCE: 145

Leu Val Cys Asp Asn Gly Ser Gly Leu Val Lys Ala Gly Phe Ala
1               5                   10                  15

<210> SEQ ID NO 146
<211> LENGTH: 15
<212> TYPE: PRT
<213> ORGANISM: Homo sapiens

<400> SEQUENCE: 146

Gly Ile Val Leu Asp Ser Gly Asp Gly Val Thr His Asn Val Pro
1               5                   10                  15

<210> SEQ ID NO 147
<211> LENGTH: 15
<212> TYPE: PRT
<213> ORGANISM: Homo sapiens

<400> SEQUENCE: 147

Val Gly Ile Asp Leu Gly Thr Thr Tyr Ser Cys Val Gly Val Phe
1               5                   10                  15

<210> SEQ ID NO 148
<211> LENGTH: 15
<212> TYPE: PRT
```

-continued

<213> ORGANISM: Homo sapiens

<400> SEQUENCE: 148

Val Leu Ile Phe Asp Leu Gly Gly Thr Phe Asp Val Ser Ile
1               5                   10                  15

<210> SEQ ID NO 149
<211> LENGTH: 15
<212> TYPE: PRT
<213> ORGANISM: Homo sapiens

<400> SEQUENCE: 149

Ile Val Leu Asp Ala Gly Ser Ser His Thr Ser Leu Tyr Ile Tyr
1               5                   10                  15

<210> SEQ ID NO 150
<211> LENGTH: 15
<212> TYPE: PRT
<213> ORGANISM: Homo sapiens

<400> SEQUENCE: 150

Phe Gly Ala Leu Asp Leu Gly Gly Ala Ser Thr Gln Val Thr Phe
1               5                   10                  15

<210> SEQ ID NO 151
<211> LENGTH: 15
<212> TYPE: PRT
<213> ORGANISM: Homo sapiens

<400> SEQUENCE: 151

Ile Val Leu Asp Ala Gly Ser Ser His Thr Ser Met Phe Ile Tyr
1               5                   10                  15

<210> SEQ ID NO 152
<211> LENGTH: 15
<212> TYPE: PRT
<213> ORGANISM: Homo sapiens

<400> SEQUENCE: 152

Leu Gly Ala Met Asp Leu Gly Gly Ala Ser Thr Gln Ile Thr Phe
1               5                   10                  15

<210> SEQ ID NO 153
<211> LENGTH: 15
<212> TYPE: PRT
<213> ORGANISM: Homo sapiens

<400> SEQUENCE: 153

Ile Val Leu Asp Ala Gly Ser Ser Arg Thr Thr Val Tyr Val Tyr
1               5                   10                  15

<210> SEQ ID NO 154
<211> LENGTH: 15
<212> TYPE: PRT
<213> ORGANISM: Homo sapiens

<400> SEQUENCE: 154

Thr Gly Ala Leu Asp Leu Gly Gly Ala Ser Thr Gln Ile Ser Phe
1               5                   10                  15

<210> SEQ ID NO 155
<211> LENGTH: 15
<212> TYPE: PRT
<213> ORGANISM: Homo sapiens -continued

```
<400> SEQUENCE: 155

Ile Val Val Asp Cys Gly Ser Ser Gly Ser Arg Val Phe Val Tyr
1               5                   10                  15

<210> SEQ ID NO 156
<211> LENGTH: 15
<212> TYPE: PRT
<213> ORGANISM: Homo sapiens

<400> SEQUENCE: 156

Ala Gly Ile Leu Asp Met Gly Gly Val Ser Thr Gln Ile Ala Tyr
1               5                   10                  15

<210> SEQ ID NO 157
<211> LENGTH: 15
<212> TYPE: PRT
<213> ORGANISM: Homo sapiens

<400> SEQUENCE: 157

Ile Met Phe Asp Ala Gly Ser Thr Gly Thr Arg Ile His Val Tyr
1               5                   10                  15

<210> SEQ ID NO 158
<211> LENGTH: 15
<212> TYPE: PRT
<213> ORGANISM: Homo sapiens

<400> SEQUENCE: 158

Val Gly Thr Leu Asp Leu Gly Gly Ala Ser Thr Gln Ile Thr Phe
1               5                   10                  15

<210> SEQ ID NO 159
<211> LENGTH: 15
<212> TYPE: PRT
<213> ORGANISM: Homo sapiens

<400> SEQUENCE: 159

Ile Met Phe Asp Ala Gly Ser Thr Gly Thr Arg Val His Val Phe
1               5                   10                  15

<210> SEQ ID NO 160
<211> LENGTH: 15
<212> TYPE: PRT
<213> ORGANISM: Homo sapiens

<400> SEQUENCE: 160

Val Gly Met Leu Asp Leu Gly Gly Gly Ser Thr Gln Ile Ala Phe
1               5                   10                  15

<210> SEQ ID NO 161
<211> LENGTH: 15
<212> TYPE: PRT
<213> ORGANISM: Homo sapiens

<400> SEQUENCE: 161

Ile Val Leu Asp Ala Gly Ser Ser His Thr Ser Leu Tyr Ile Tyr
1               5                   10                  15

<210> SEQ ID NO 162
<211> LENGTH: 15
<212> TYPE: PRT
<213> ORGANISM: Homo sapiens

<400> SEQUENCE: 162
```

```
Ile Val Leu Asp Ala Gly Ser Ser Gly Thr Ser Leu Tyr Ile Tyr
1               5                   10                  15

<210> SEQ ID NO 163
<211> LENGTH: 15
<212> TYPE: PRT
<213> ORGANISM: Homo sapiens

<400> SEQUENCE: 163

Ile Val Leu Asp Ala Gly Ser Ser Ala Thr Ser Leu Tyr Ile Tyr
1               5                   10                  15

<210> SEQ ID NO 164
<211> LENGTH: 15
<212> TYPE: PRT
<213> ORGANISM: Homo sapiens

<400> SEQUENCE: 164

Ile Val Leu Asp Ala Gly Ser Ser Gly Thr Arg Leu Tyr Ile Tyr
1               5                   10                  15

<210> SEQ ID NO 165
<211> LENGTH: 15
<212> TYPE: PRT
<213> ORGANISM: Homo sapiens

<400> SEQUENCE: 165

Ile Val Leu Asp Ala Gly Ser Ser Ala Thr Arg Leu Tyr Ile Tyr
1               5                   10                  15

<210> SEQ ID NO 166
<211> LENGTH: 15
<212> TYPE: PRT
<213> ORGANISM: Homo sapiens

<400> SEQUENCE: 166

Ile Val Leu Asp Ala Gly Ser Ser Arg Thr Thr Val Tyr Val Tyr
1               5                   10                  15

<210> SEQ ID NO 167
<211> LENGTH: 15
<212> TYPE: PRT
<213> ORGANISM: Homo sapiens

<400> SEQUENCE: 167

Ile Val Leu Asp Ala Gly Ser Ser Gly Thr Thr Val Tyr Val Tyr
1               5                   10                  15

<210> SEQ ID NO 168
<211> LENGTH: 15
<212> TYPE: PRT
<213> ORGANISM: Homo sapiens

<400> SEQUENCE: 168

Ile Val Leu Asp Ala Gly Ser Ser Ala Thr Thr Val Tyr Val Tyr
1               5                   10                  15

<210> SEQ ID NO 169
<211> LENGTH: 15
<212> TYPE: PRT
<213> ORGANISM: Homo sapiens

<400> SEQUENCE: 169

Ile Val Leu Asp Ala Gly Ser Ser Gly Thr Arg Val Tyr Val Tyr
1               5                   10                  15
```

<210> SEQ ID NO 170
<211> LENGTH: 15
<212> TYPE: PRT
<213> ORGANISM: Homo sapiens

<400> SEQUENCE: 170

Ile Val Leu Asp Ala Gly Ser Ser Ala Thr Arg Val Tyr Val Tyr
 1               5                   10                  15

<210> SEQ ID NO 171
<211> LENGTH: 517
<212> TYPE: PRT
<213> ORGANISM: Homo sapiens

<400> SEQUENCE: 171

Met Lys Gly Thr Lys Asp Leu Thr Ser Gln Gln Lys Glu Ser Asn Val
 1               5                   10                  15

Lys Thr Phe Cys Ser Lys Asn Ile Leu Ala Ile Leu Gly Phe Ser Ser
                20                  25                  30

Ile Ile Ala Val Ile Ala Leu Leu Ala Val Gly Leu Thr Gln Asn Lys
            35                  40                  45

Ala Leu Pro Glu Asn Val Lys Tyr Gly Ile Val Leu Asp Ala Gly Ser
        50                  55                  60

Ser His Thr Ser Leu Tyr Ile Tyr Lys Trp Pro Ala Glu Lys Glu Asn
65                  70                  75                  80

Asp Thr Gly Val Val His Gln Val Glu Glu Cys Arg Val Lys Gly Pro
                85                  90                  95

Gly Ile Ser Lys Phe Val Gln Lys Val Asn Glu Ile Gly Ile Tyr Leu
            100                 105                 110

Thr Asp Cys Met Glu Arg Ala Arg Glu Val Ile Pro Arg Ser Gln His
        115                 120                 125

Gln Glu Thr Pro Val Tyr Leu Gly Ala Thr Ala Gly Met Arg Leu Leu
    130                 135                 140

Arg Met Glu Ser Glu Glu Leu Ala Asp Arg Val Leu Asp Val Val Glu
145                 150                 155                 160

Arg Ser Leu Ser Asn Tyr Pro Phe Asp Phe Gln Gly Ala Arg Ile Ile
                165                 170                 175

Thr Gly Gln Glu Glu Gly Ala Tyr Gly Trp Ile Thr Ile Asn Tyr Leu
            180                 185                 190

Leu Gly Lys Phe Ser Gln Lys Thr Arg Trp Phe Ser Ile Val Pro Tyr
        195                 200                 205

Glu Thr Asn Asn Gln Glu Thr Phe Gly Ala Leu Asp Leu Gly Gly Ala
    210                 215                 220

Ser Thr Gln Val Thr Phe Val Pro Gln Asn Gln Thr Ile Glu Ser Pro
225                 230                 235                 240

Asp Asn Ala Leu Gln Phe Arg Leu Tyr Gly Lys Asp Tyr Asn Val Tyr
                245                 250                 255

Thr His Ser Phe Leu Cys Tyr Gly Lys Asp Gln Ala Leu Trp Gln Lys
            260                 265                 270

Leu Ala Lys Asp Ile Gln Val Ala Ser Asn Glu Ile Leu Arg Asp Pro
        275                 280                 285

Cys Phe His Pro Gly Tyr Lys Lys Val Val Asn Val Ser Asp Leu Tyr
    290                 295                 300

Lys Thr Pro Cys Thr Lys Arg Phe Glu Met Thr Leu Pro Phe Gln Gln
305                 310                 315                 320

```
Phe Glu Ile Gln Gly Ile Gly Asn Tyr Gln Gln Cys His Gln Ser Ile
                325                 330                 335

Leu Glu Leu Phe Asn Thr Ser Tyr Cys Pro Tyr Ser Gln Cys Ala Phe
            340                 345                 350

Asn Gly Ile Phe Leu Pro Pro Leu Gln Gly Asp Phe Gly Ala Phe Ser
        355                 360                 365

Ala Phe Tyr Phe Val Met Lys Phe Leu Asn Leu Thr Ser Glu Lys Val
    370                 375                 380

Ser Gln Glu Lys Val Thr Glu Met Met Lys Lys Phe Cys Ala Gln Pro
385                 390                 395                 400

Trp Glu Glu Ile Lys Thr Ser Tyr Ala Gly Val Lys Glu Lys Tyr Leu
                405                 410                 415

Ser Glu Tyr Cys Phe Ser Gly Thr Tyr Ile Leu Ser Leu Leu Leu Gln
            420                 425                 430

Gly Tyr His Phe Thr Ala Asp Ser Trp Glu His Ile His Phe Ile Gly
        435                 440                 445

Lys Ile Gln Gly Ser Asp Ala Gly Trp Thr Leu Gly Tyr Met Leu Asn
    450                 455                 460

Leu Thr Asn Met Ile Pro Ala Glu Gln Pro Leu Ser Thr Pro Leu Ser
465                 470                 475                 480

His Ser Thr Tyr Val Phe Leu Met Val Leu Phe Ser Leu Val Leu Phe
                485                 490                 495

Thr Val Ala Ile Ile Gly Leu Leu Ile Phe His Lys Pro Ser Tyr Phe
            500                 505                 510

Trp Lys Asp Met Val
        515

<210> SEQ ID NO 172
<211> LENGTH: 495
<212> TYPE: PRT
<213> ORGANISM: Homo sapiens

<400> SEQUENCE: 172

Met Ala Gly Lys Val Arg Ser Leu Leu Pro Leu Leu Leu Ala Ala
1               5                   10                  15

Ala Gly Leu Ala Gly Leu Leu Leu Cys Val Pro Thr Arg Asp Val
                20                  25                  30

Arg Glu Pro Pro Ala Leu Lys Tyr Gly Ile Val Leu Asp Ala Gly Ser
            35                  40                  45

Ser His Thr Ser Met Phe Ile Tyr Lys Trp Pro Ala Asp Lys Glu Asn
    50                  55                  60

Asp Thr Gly Ile Val Gly Gln His Ser Ser Cys Asp Val Pro Gly Gly
65                  70                  75                  80

Gly Ile Ser Ser Tyr Ala Asp Asn Pro Ser Gly Ala Ser Gln Ser Leu
                85                  90                  95

Val Gly Cys Leu Glu Gln Ala Leu Gln Asp Val Pro Lys Glu Arg His
            100                 105                 110

Ala Gly Thr Pro Leu Tyr Leu Gly Ala Thr Ala Gly Met Arg Leu Leu
        115                 120                 125

Asn Leu Thr Asn Pro Glu Ala Ser Thr Ser Val Leu Met Ala Val Thr
    130                 135                 140

His Thr Leu Thr Gln Tyr Pro Phe Asp Phe Arg Gly Ala Arg Ile Leu
145                 150                 155                 160

Ser Gly Gln Glu Glu Gly Val Phe Gly Trp Val Thr Ala Asn Tyr Leu
```

-continued

```
                165                 170                 175
Leu Glu Asn Phe Ile Lys Tyr Gly Trp Val Gly Arg Trp Phe Arg Pro
                180                 185                 190

Arg Lys Gly Thr Leu Gly Ala Met Asp Leu Gly Gly Ala Ser Thr Gln
                195                 200                 205

Ile Thr Phe Glu Thr Thr Ser Pro Ala Glu Asp Arg Ala Ser Glu Val
            210                 215                 220

Gln Leu His Leu Tyr Gly Gln His Tyr Arg Val Tyr Thr His Ser Phe
225                 230                 235                 240

Leu Cys Tyr Gly Arg Asp Gln Val Leu Gln Arg Leu Leu Ala Ser Ala
                245                 250                 255

Leu Gln Thr His Gly Phe His Pro Cys Trp Pro Arg Gly Phe Ser Thr
                260                 265                 270

Gln Val Leu Leu Gly Asp Val Tyr Gln Ser Pro Cys Thr Met Ala Gln
            275                 280                 285

Arg Pro Gln Asn Phe Asn Ser Ser Ala Arg Val Ser Leu Ser Gly Ser
290                 295                 300

Ser Asp Pro His Leu Cys Arg Asp Leu Val Ser Gly Leu Phe Ser Phe
305                 310                 315                 320

Ser Ser Cys Pro Phe Ser Arg Cys Ser Phe Asn Gly Val Phe Gln Pro
                325                 330                 335

Pro Val Ala Gly Asn Phe Val Ala Phe Ser Ala Phe Phe Tyr Thr Val
            340                 345                 350

Asp Phe Leu Arg Thr Ser Met Gly Leu Pro Val Ala Thr Leu Gln Gln
                355                 360                 365

Leu Glu Ala Ala Val Asn Val Cys Asn Gln Thr Trp Ala Gln Leu
            370                 375                 380

Gln Ala Arg Val Pro Gly Gln Arg Ala Arg Leu Ala Asp Tyr Cys Ala
385                 390                 395                 400

Gly Ala Met Phe Val Gln Gln Leu Leu Ser Arg Gly Tyr Gly Phe Asp
                405                 410                 415

Glu Arg Ala Phe Gly Gly Val Ile Phe Gln Lys Lys Ala Ala Asp Thr
            420                 425                 430

Ala Val Gly Trp Ala Leu Gly Tyr Met Leu Asn Leu Thr Asn Leu Ile
            435                 440                 445

Pro Ala Asp Pro Pro Gly Leu Arg Lys Gly Thr Asp Phe Ser Ser Trp
            450                 455                 460

Val Val Leu Leu Leu Leu Phe Ala Ser Ala Leu Leu Ala Ala Leu Val
465                 470                 475                 480

Leu Leu Leu Arg Gln Val His Ser Ala Lys Leu Pro Ser Thr Ile
                485                 490                 495
```

<210> SEQ ID NO 173
<211> LENGTH: 484
<212> TYPE: PRT
<213> ORGANISM: Homo sapiens

<400> SEQUENCE: 173

```
Met Lys Lys Gly Ile Arg Tyr Glu Thr Ser Arg Lys Thr Ser Tyr Ile
1               5                   10                  15

Phe Gln Gln Pro Gln His Gly Pro Trp Gln Thr Arg Met Arg Lys Ile
                20                  25                  30

Ser Asn His Gly Ser Leu Arg Val Ala Lys Val Ala Tyr Pro Leu Gly
            35                  40                  45
```

-continued

```
Leu Cys Val Gly Val Phe Ile Tyr Val Ala Tyr Ile Lys Trp His Arg
 50                  55                  60

Ala Thr Ala Thr Gln Ala Phe Phe Ser Ile Thr Arg Ala Ala Pro Gly
 65                  70                  75                  80

Ala Arg Trp Gly Gln Gln Ala His Ser Pro Leu Gly Thr Ala Ala Asp
                 85                  90                  95

Gly His Glu Val Phe Tyr Gly Ile Met Phe Asp Ala Gly Ser Thr Gly
                100                 105                 110

Thr Arg Val His Val Phe Gln Phe Thr Arg Pro Pro Arg Glu Thr Pro
            115                 120                 125

Thr Leu Thr His Glu Thr Phe Lys Ala Val Lys Pro Gly Leu Ser Ala
130                 135                 140

Tyr Ala Asp Asp Val Glu Lys Ser Ala Gln Gly Ile Arg Glu Leu Leu
145                 150                 155                 160

Asp Val Ala Lys Gln Asp Ile Pro Phe Asp Phe Trp Lys Ala Thr Pro
                165                 170                 175

Leu Val Leu Lys Ala Thr Ala Gly Leu Arg Leu Leu Pro Gly Glu Lys
                180                 185                 190

Ala Gln Lys Leu Leu Gln Lys Val Lys Glu Val Phe Lys Ala Ser Pro
                195                 200                 205

Phe Leu Val Gly Asp Asp Cys Val Ser Ile Met Asn Gly Thr Asp Glu
210                 215                 220

Gly Val Ser Ala Trp Ile Thr Ile Asn Phe Leu Thr Gly Ser Leu Lys
225                 230                 235                 240

Thr Pro Gly Gly Ser Ser Val Gly Met Leu Asp Leu Gly Gly Gly Ser
                245                 250                 255

Thr Gln Ile Ala Phe Leu Pro Arg Val Glu Gly Thr Leu Gln Ala Ser
                260                 265                 270

Pro Pro Gly Tyr Leu Thr Ala Leu Arg Met Phe Asn Arg Thr Tyr Lys
                275                 280                 285

Leu Tyr Ser Tyr Ser Tyr Leu Gly Leu Gly Leu Met Ser Ala Arg Leu
                290                 295                 300

Ala Ile Leu Gly Gly Val Glu Gly Gln Pro Ala Lys Asp Gly Lys Glu
305                 310                 315                 320

Leu Val Ser Pro Cys Leu Ser Pro Ser Phe Lys Gly Glu Trp Glu His
                325                 330                 335

Ala Glu Val Thr Tyr Arg Val Ser Gly Gln Lys Ala Ala Ser Leu
                340                 345                 350

His Glu Leu Cys Ala Ala Arg Val Ser Glu Val Leu Gln Asn Arg Val
                355                 360                 365

His Arg Thr Glu Glu Val Lys His Val Asp Phe Tyr Ala Phe Ser Tyr
                370                 375                 380

Tyr Tyr Asp Leu Ala Ala Gly Val Gly Leu Ile Asp Ala Glu Lys Gly
385                 390                 395                 400

Gly Ser Leu Val Val Gly Asp Phe Glu Ile Ala Ala Lys Tyr Val Cys
                405                 410                 415

Arg Thr Leu Glu Thr Gln Pro Gln Ser Ser Pro Phe Ser Cys Met Asp
                420                 425                 430

Leu Thr Tyr Val Ser Leu Leu Gln Glu Phe Gly Phe Pro Arg Ser
                435                 440                 445

Lys Val Leu Lys Leu Thr Arg Lys Ile Asp Asn Val Glu Thr Ser Trp
450                 455                 460

Ala Leu Gly Ala Ile Phe His Tyr Ile Asp Ser Leu Asn Arg Gln Lys
```

```
            465                 470                 475                 480
Ser Pro Ala Ser

<210> SEQ ID NO 174
<211> LENGTH: 529
<212> TYPE: PRT
<213> ORGANISM: Homo sapiens

<400> SEQUENCE: 174

Met Phe Thr Val Leu Thr Arg Gln Pro Cys Glu Gln Ala Gly Leu Lys
  1               5                  10                  15

Ala Leu Tyr Arg Thr Pro Thr Ile Ile Ala Leu Val Val Leu Leu Val
                 20                  25                  30

Ser Ile Val Val Leu Val Ser Ile Thr Val Ile Gln Ile His Lys Gln
             35                  40                  45

Glu Val Leu Pro Pro Gly Leu Lys Tyr Gly Ile Val Leu Asp Ala Gly
         50                  55                  60

Ser Ser Arg Thr Thr Val Tyr Val Tyr Gln Trp Pro Ala Glu Lys Glu
 65                  70                  75                  80

Asn Asn Thr Gly Val Val Ser Gln Thr Phe Lys Cys Ser Val Lys Gly
                 85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
            180                 185                 190

Leu Met Gly Asn Phe Leu Glu Lys Asn Leu Trp His Met Trp Val His
        195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
        275                 280                 285

Cys Tyr Pro Arg Asp Tyr Ser Ile Ser Phe Thr Met Gly His Val Phe
    290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
            340                 345                 350

Cys Ser Phe Asp Gly Val Tyr Gln Pro Lys Ile Lys Gly Pro Phe Val
```

-continued

```
            355                 360                 365
Ala Phe Ala Gly Phe Tyr Tyr Thr Ala Ser Ala Leu Asn Leu Ser Gly
    370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Leu Pro Lys Phe Asp Glu Val
                405                 410                 415

Tyr Ala Arg Ser Tyr Cys Phe Ser Ala Asn Tyr Ile Tyr His Leu Phe
            420                 425                 430

Val Asn Gly Tyr Lys Phe Thr Glu Glu Thr Trp Pro Gln Ile His Phe
        435                 440                 445

Glu Lys Glu Val Gly Asn Ser Ser Ile Ala Trp Ser Leu Gly Tyr Met
    450                 455                 460

Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Val
                485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
        515                 520                 525

Asp

<210> SEQ ID NO 175
<211> LENGTH: 428
<212> TYPE: PRT
<213> ORGANISM: Homo sapiens

<400> SEQUENCE: 175

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr Gly Thr Arg Ile His Val
    50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
```

```
                    195                 200                 205
Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Val Lys Tyr
        275                 280                 285

Gln Tyr Gly Gly Asn Gln Glu Gly Glu Val Gly Phe Glu Pro Cys Tyr
    290                 295                 300

Ala Glu Val Leu Arg Val Val Arg Gly Lys Leu His Gln Pro Glu Glu
305                 310                 315                 320

Val Gln Arg Gly Ser Phe Tyr Ala Phe Ser Tyr Tyr Tyr Asp Arg Ala
                325                 330                 335

Val Asp Thr Asp Met Ile Asp Tyr Glu Lys Gly Gly Ile Leu Lys Val
            340                 345                 350

Glu Asp Phe Glu Arg Lys Ala Arg Glu Val Cys Asp Asn Leu Glu Asn
        355                 360                 365

Phe Thr Ser Gly Ser Pro Phe Leu Cys Met Asp Leu Ser Tyr Ile Thr
    370                 375                 380

Ala Leu Leu Lys Asp Gly Phe Gly Phe Ala Asp Ser Thr Val Leu Gln
385                 390                 395                 400

Leu Thr Lys Lys Val Asn Asn Ile Glu Thr Gly Trp Ala Leu Gly Ala
                405                 410                 415

Thr Phe His Leu Leu Gln Ser Leu Gly Ile Ser His
            420                 425

<210> SEQ ID NO 176
<211> LENGTH: 613
<212> TYPE: PRT
<213> ORGANISM: Homo sapiens

<400> SEQUENCE: 176

Ile Gly Ile Ser Cys Leu Phe Pro Ala Ser Trp His Phe Ser Ile Ser
1               5                   10                  15

Pro Val Gly Cys Pro Arg Ile Leu Asn Thr Asn Leu Arg Gln Ile Met
            20                  25                  30

Val Ile Ser Val Leu Ala Ala Ala Val Ser Leu Leu Tyr Phe Ser Val
        35                  40                  45

Val Ile Ile Arg Asn Lys Tyr Gly Arg Leu Thr Arg Asp Lys Lys Phe
    50                  55                  60

Gln Arg Tyr Leu Ala Arg Val Thr Asp Ile Glu Ala Thr Asp Thr Asn
65                  70                  75                  80

Asn Pro Asn Val Asn Tyr Gly Ile Val Val Asp Cys Gly Ser Ser Gly
                85                  90                  95

Ser Arg Val Phe Val Tyr Cys Trp Pro Arg His Asn Gly Asn Pro His
            100                 105                 110

Asp Leu Leu Asp Ile Arg Gln Met Arg Asp Lys Asn Arg Lys Pro Val
        115                 120                 125

Val Met Lys Ile Lys Pro Gly Ile Ser Glu Phe Ala Thr Ser Pro Glu
    130                 135                 140
```

-continued

```
Lys Val Ser Asp Tyr Ile Ser Pro Leu Leu Asn Phe Ala Ala Glu His
145                 150                 155                 160

Val Pro Arg Ala Lys His Lys Glu Thr Pro Leu Tyr Ile Leu Cys Thr
                165                 170                 175

Ala Gly Met Arg Ile Leu Pro Glu Ser Gln Gln Lys Ala Ile Leu Glu
            180                 185                 190

Asp Leu Leu Thr Asp Ile Pro Val His Phe Asp Phe Leu Phe Ser Asp
        195                 200                 205

Ser His Ala Glu Val Ile Ser Gly Lys Gln Glu Gly Val Tyr Ala Trp
    210                 215                 220

Ile Gly Ile Asn Phe Val Leu Gly Arg Phe Glu His Ile Glu Asp Asp
225                 230                 235                 240

Asp Glu Ala Val Val Glu Val Asn Ile Pro Gly Ser Glu Ser Ser Glu
                245                 250                 255

Ala Ile Val Arg Lys Arg Thr Ala Gly Ile Leu Asp Met Gly Gly Val
            260                 265                 270

Ser Thr Gln Ile Ala Tyr Glu Val Pro Lys Thr Val Ser Phe Ala Ser
        275                 280                 285

Ser Gln Gln Glu Glu Val Ala Lys Asn Leu Leu Ala Glu Phe Asn Leu
    290                 295                 300

Gly Cys Asp Val His Gln Thr Glu His Val Tyr Arg Val Tyr Val Ala
305                 310                 315                 320

Thr Phe Leu Gly Phe Gly Gly Asn Ala Ala Arg Gln Arg Tyr Glu Asp
                325                 330                 335

Arg Ile Phe Ala Asn Thr Ile Gln Lys Asn Arg Leu Leu Gly Lys Gln
            340                 345                 350

Thr Gly Leu Thr Pro Asp Met Pro Tyr Leu Asp Pro Cys Leu Pro Leu
        355                 360                 365

Asp Ile Lys Asp Glu Ile Gln Gln Asn Gly Gln Thr Ile Tyr Leu Arg
    370                 375                 380

Gly Thr Gly Asp Phe Asp Leu Cys Arg Glu Thr Ile Gln Pro Phe Met
385                 390                 395                 400

Asn Lys Thr Asn Glu Thr Gln Thr Ser Leu Asn Gly Val Tyr Gln Pro
                405                 410                 415

Pro Ile His Phe Gln Asn Ser Glu Phe Tyr Gly Phe Ser Glu Phe Tyr
            420                 425                 430

Tyr Cys Thr Glu Asp Val Leu Arg Met Gly Gly Asp Tyr Asn Ala Ala
        435                 440                 445

Lys Phe Thr Lys Ala Ala Lys Asp Tyr Cys Ala Thr Lys Trp Ser Ile
    450                 455                 460

Leu Arg Glu Arg Phe Asp Arg Gly Leu Tyr Ala Ser His Ala Asp Leu
465                 470                 475                 480

His Arg Leu Lys Tyr Gln Cys Phe Lys Ser Ala Trp Met Phe Glu Val
                485                 490                 495

Phe His Arg Gly Phe Ser Phe Pro Val Asn Tyr Lys Ser Leu Lys Thr
            500                 505                 510

Ala Leu Gln Val Tyr Asp Lys Glu Val Gln Trp Thr Leu Gly Ala Ile
        515                 520                 525

Leu Tyr Arg Thr Arg Phe Leu Pro Leu Arg Asp Ile Gln Gln Glu Ala
    530                 535                 540

Phe Arg Ala Ser His Thr His Trp Arg Gly Val Ser Phe Val Tyr Asn
545                 550                 555                 560

His Tyr Leu Phe Ser Gly Cys Phe Leu Val Val Leu Leu Ala Ile Leu
```

```
                565                 570                 575
Leu Tyr Leu Leu Arg Leu Arg Arg Ile His Arg Arg Thr Pro Arg Ser
            580                 585                 590

Ser Ser Ala Ala Ala Leu Trp Met Glu Glu Gly Leu Pro Ala Gln Asn
        595                 600                 605

Ala Pro Gly Thr Leu
    610

<210> SEQ ID NO 177
<211> LENGTH: 75
<212> TYPE: DNA
<213> ORGANISM: Homo sapiens

<400> SEQUENCE: 177
atggagacag acacactcct gctatgggta ctgctgctct gggttccagg ttccactggt      60
gacgcgcccg ggccg                                                      75

<210> SEQ ID NO 178
<211> LENGTH: 23
<212> TYPE: PRT
<213> ORGANISM: Homo sapiens

<400> SEQUENCE: 178

Met Glu Thr Asp Thr Leu Leu Trp Val Leu Leu Leu Trp Val Pro Gly
 1               5                  10                  15

Ser Thr Gly Asp Ala Pro Gly
            20

<210> SEQ ID NO 179
<211> LENGTH: 336
<212> TYPE: PRT
<213> ORGANISM: Phlebotomus papatasii

<400> SEQUENCE: 179

Met Phe Leu Lys Phe Cys Ile Val Ala Phe Ala Ile Cys Leu Ser Ile
 1               5                  10                  15

Asn Leu Ser Glu Gly Ala Pro Arg Ser Gly Thr Ile Tyr Asn Phe Ala
            20                  25                  30

Ile Ile Ala Asp Leu Asp Lys Lys Ser Ile Ser Pro Lys Asn Asp Asn
        35                  40                  45

Asn Tyr Lys Ser Ile Val Lys Val Gly Glu Leu Ile Glu Val Gly Asp
    50                  55                  60

Lys Tyr Ser Val Lys Met Lys Lys Glu Asp His Glu Ile Phe Thr Lys
 65                  70                  75                  80

Tyr Ala Tyr Lys Gly Arg Gly Ala Glu Leu Ser Glu Phe Leu Ile Tyr
                85                  90                  95

Lys Trp Lys Leu Tyr Thr Phe Asp Asp Lys Ser Gly Ile Val Phe Arg
            100                 105                 110

Leu Lys Thr Asn Ala Asp Leu Ile Pro Trp Val Thr Leu Ala Asn Gly
        115                 120                 125

Asn Gly Asp Gln Thr Asp Gly Phe Lys Ala Glu Trp Ala Thr Thr Lys
    130                 135                 140

Gly Asp Lys Met Tyr Val Gly Ser Thr Gly Ile Ser Phe Thr Asp Lys
145                 150                 155                 160

Thr Gly Lys Leu Asn Ser Asn Ser Leu Trp Ile Lys Glu Ile Asp Gln
                165                 170                 175

Asp Gly Lys Val Gln Ser Leu Asp Trp Lys Glu Gln Tyr Asp Lys Ile
```

-continued

```
                180                 185                 190
Lys Ser Ala Met Lys Ile Pro Asn Gly Phe Ile Trp His Glu Ala Val
            195                 200                 205
Asn Trp Ser Lys Leu Lys Asn Gln Trp Val Phe Leu Pro Arg Lys Cys
        210                 215                 220
Ser Glu Arg Pro Phe Asp Thr Lys Thr Glu Thr Ile Gly Cys Asn
225                 230                 235                 240
Lys Ile Ile Ile Ala Ser Glu Asn Phe Glu Ile Ile Lys Ser Ile Gln
                245                 250                 255
Ile Lys Gly Lys Ser Ile Asn Arg Ala Ala Gly Phe Ser Ser Phe Lys
            260                 265                 270
Phe Leu Pro Asp Ser Asp Gln Ile Leu Leu Ala Leu Lys Thr Ile
        275                 280                 285
Glu Lys Asp Asp Lys Thr Ala Thr Tyr Ile Thr Val Ile Asp Ile Thr
            290                 295                 300
Gly Arg Val Leu Met Pro Glu Met Gln Ile Asn Ser Asp Lys Tyr Glu
305                 310                 315                 320
Gly Ile Val Leu Leu Lys Ser Thr Glu Gly Phe Leu Lys Arg Ser Gln
                325                 330                 335

<210> SEQ ID NO 180
<211> LENGTH: 364
<212> TYPE: PRT
<213> ORGANISM: Cimex lectularius

<400> SEQUENCE: 180

Met Arg Ser Ser Tyr Arg Val Gly Asn Pro Ile Arg Phe Gln Pro Thr
1               5                   10                  15
Asn Val Val Gly Leu Leu Leu Ser Leu Val Leu Ser Phe Met Leu
            20                  25                  30
Val Gln Ser Tyr Glu Leu Gly His Ala Ser Gly Glu Thr Asn Ala Asn
        35                  40                  45
Ser Lys Tyr Pro Leu Thr Thr Pro Val Glu Glu Asn Leu Lys Val Arg
    50                  55                  60
Phe Lys Ile Gly Val Ile Ser Asp Asp Lys Asn Ala Val Ser Lys
65                  70                  75                  80
Asp Glu Ser Asn Thr Trp Val Ser Thr Tyr Leu Thr Gly Thr Leu Glu
                85                  90                  95
Trp Glu Lys Ser Thr Asp Lys Ile Thr Val Gln Trp Asp Lys Gly Asn
            100                 105                 110
Glu Lys Lys Val Lys Ser Lys Tyr Ser Tyr Gly Gly Arg Gly Met Glu
        115                 120                 125
Leu Ser Glu Leu Val Thr Phe Asn Gly Asn Leu Leu Thr Phe Asp Asp
    130                 135                 140
Arg Thr Gly Leu Val Tyr Ile Leu Lys Asp Asp Lys Val Tyr Pro Trp
145                 150                 155                 160
Val Val Leu Ala Asp Gly Asp Gly Lys Asn Ser Lys Gly Phe Lys Ser
                165                 170                 175
Glu Trp Ala Thr Glu Lys Ala Gly Asn Leu Tyr Val Gly Ser Ser Gly
            180                 185                 190
Lys Glu Trp Thr Thr Lys Glu Gly Thr Ile Glu Asn Tyr Asn Pro Met
        195                 200                 205
Trp Val Lys Met Ile Asn Lys Asn Gly Glu Val Thr Ser Leu Asn Trp
    210                 215                 220
```

```
Gln Thr Asn Tyr Glu Lys Ile Arg Ser Ser Met Asn Ile Thr Phe Pro
225                 230                 235                 240

Gly Tyr Met Trp His Glu Ala Ala Cys Trp Ser Asp Lys Tyr Asn Lys
                245                 250                 255

Trp Phe Phe Leu Pro Arg Ala Leu Ser Gln Glu Ala Tyr Asp Ser Lys
            260                 265                 270

Lys Phe Glu Thr Gln Gly Ala Asn Val Ile Ile Ser Cys Asp Asp Lys
        275                 280                 285

Phe Glu Lys Cys Glu Pro Thr Gln Ile Gln Gly Lys Thr Glu Asp Lys
    290                 295                 300

Arg Gly Phe Ser Asn Phe Lys Phe Val Pro Thr Ser Glu Asp Lys Ile
305                 310                 315                 320

Ile Val Gly Leu Lys Thr Val Glu Ala Asp Asp Thr Thr Glu Thr Tyr
                325                 330                 335

Phe Thr Ala Phe Asp Leu Glu Gly Lys Val Leu Leu Glu Glu Thr Lys
            340                 345                 350

Ile Asp Asp His Lys Tyr Glu Gly Val Asp Phe Val
        355                 360

<210> SEQ ID NO 181
<211> LENGTH: 371
<212> TYPE: PRT
<213> ORGANISM: Homo sapiens

<400> SEQUENCE: 181

Met Thr Lys Ala Ala Asp Pro Arg Phe Arg Pro Arg Trp Lys Val Ile
1               5                   10                  15

Leu Thr Phe Phe Val Gly Ala Ile Leu Trp Leu Leu Cys Ser His
                20                  25                  30

Arg Pro Ala Pro Gly Arg Pro Pro Thr His Asn Ala His Asn Trp Arg
                35                  40                  45

Leu Gly Gln Ala Pro Ala Asn Trp Tyr Asn Asp Thr Tyr Pro Leu Ser
    50                  55                  60

Pro Pro Gln Arg Thr Pro Ala Gly Ile Arg Tyr Arg Ile Ala Val Ile
65                  70                  75                  80

Ala Asp Leu Asp Thr Glu Ser Arg Ala Gln Glu Glu Asn Thr Trp Phe
                85                  90                  95

Ser Tyr Leu Lys Lys Gly Tyr Leu Thr Leu Ser Asp Ser Gly Asp Lys
                100                 105                 110

Val Ala Val Glu Trp Asp Lys Asp His Gly Val Leu Glu Ser His Leu
            115                 120                 125

Ala Glu Lys Gly Arg Gly Met Glu Leu Ser Asp Leu Ile Val Phe Asn
    130                 135                 140

Gly Lys Leu Tyr Ser Val Asp Asp Arg Thr Gly Val Val Tyr Gln Ile
145                 150                 155                 160

Glu Gly Ser Lys Ala Val Pro Trp Val Ile Leu Ser Asp Gly Asp Gly
                165                 170                 175

Thr Val Glu Lys Gly Phe Lys Ala Glu Trp Leu Ala Val Lys Asp Glu
            180                 185                 190

Arg Leu Tyr Val Gly Gly Leu Gly Lys Glu Trp Thr Thr Thr Thr Gly
        195                 200                 205

Asp Val Val Asn Glu Asn Pro Glu Trp Val Lys Val Val Gly Tyr Lys
    210                 215                 220

Gly Ser Val Asp His Glu Asn Trp Val Ser Asn Tyr Asn Ala Leu Arg
225                 230                 235                 240
```

```
Ala Ala Ala Gly Ile Gln Pro Pro Gly Tyr Leu Ile His Glu Ser Ala
            245                 250                 255

Cys Trp Ser Asp Thr Leu Gln Arg Trp Phe Leu Pro Arg Arg Ala
            260                 265                 270

Ser Gln Glu Arg Tyr Ser Glu Lys Asp Asp Glu Arg Lys Gly Ala Asn
            275                 280                 285

Leu Leu Leu Ser Ala Ser Pro Asp Phe Gly Asp Ile Ala Val Ser His
            290                 295                 300

Val Gly Ala Val Val Pro Thr His Gly Phe Ser Ser Phe Lys Phe Ile
305                 310                 315                 320

Pro Asn Thr Asp Asp Gln Ile Ile Val Ala Leu Lys Ser Glu Glu Asp
            325                 330                 335

Ser Gly Arg Val Ala Ser Tyr Ile Met Ala Phe Thr Leu Asp Gly Arg
            340                 345                 350

Phe Leu Leu Pro Glu Thr Lys Ile Gly Ser Val Lys Tyr Glu Gly Ile
            355                 360                 365

Glu Phe Ile
    370

<210> SEQ ID NO 182
<211> LENGTH: 403
<212> TYPE: PRT
<213> ORGANISM: Rattus rattus

<400> SEQUENCE: 182

Met Pro Ile Gln Pro Phe Asp Gln Arg Glu Trp Asn Glu Pro Met His
1               5                   10                  15

Ser Leu Arg Ile Ser Val Gly Gly Leu Pro Val Leu Ala Ser Met Thr
            20                  25                  30

Lys Ala Thr Asp Pro Arg Phe Arg Pro Arg Trp Arg Val Ile Leu Thr
            35                  40                  45

Ser Phe Val Gly Ala Ala Leu Leu Trp Leu Leu Tyr Ser His His Gln
    50                  55                  60

Thr Pro Val Ser Gly Arg Pro Pro Ile His Asn Ala His Asn Trp Arg
65                  70                  75                  80

Leu Arg Gln Glu Arg Ile Ser Gln Tyr Asn Asp Thr Tyr Pro Leu Ser
            85                  90                  95

Pro Pro Gln Arg Thr Pro Gly Gly Ile Arg Tyr Arg Ile Ala Val Ile
            100                 105                 110

Ala Asp Leu Asp Thr Gly Ser Lys Ala Gln Glu Glu Asn Thr Trp Phe
            115                 120                 125

Ser Tyr Leu Lys Lys Gly Tyr Leu Thr Leu Ser Asp Ser Gly Asp Arg
            130                 135                 140

Val Ser Val Glu Trp Asp Lys Asp Arg Gly Val Leu Glu Ser His Leu
145                 150                 155                 160

Ala Glu Lys Gly Arg Gly Met Glu Leu Ser Asp Leu Ile Val Phe Asn
            165                 170                 175

Gly Lys Leu Tyr Ser Val Asp Asp Arg Thr Gly Val Ile Tyr Gln Ile
            180                 185                 190

Glu Gly Thr Lys Ala Val Pro Trp Val Ile Leu Ser Asp Gly Asp Gly
            195                 200                 205

Ala Val Glu Lys Gly Phe Lys Ala Glu Trp Leu Ala Val Lys Asp Glu
            210                 215                 220

His Leu Tyr Val Gly Gly Leu Gly Lys Glu Trp Thr Thr Thr Thr Gly
```

```
            225                 230                 235                 240
Glu Val Val Asn Glu Asn Pro Glu Trp Val Lys Val Val Gly His Arg
                245                 250                 255
Gly Ser Val Glu His Glu Asn Trp Val Ser Ser Tyr Asn Ala Leu Arg
                260                 265                 270
Ala Ala Ala Gly Ile Gln Pro Gly Tyr Leu Ile His Glu Ser Ala
            275                 280                 285
Cys Trp Ser Asp Thr Leu Gln Arg Trp Phe Phe Leu Pro Arg Arg Ala
        290                 295                 300
Ser His Glu Arg Tyr Ser Glu Arg Glu Asp Arg Lys Gly Ser Asn
305                 310                 315                 320
Leu Leu Leu Ser Ala Ala Gln Asp Phe Arg Asp Ile Ser Val Arg Gln
                325                 330                 335
Val Gly Ala Leu Val Pro Thr His Gly Phe Ser Ser Phe Lys Phe Ile
            340                 345                 350
Pro Asn Thr Asp Asp Gln Ile Ile Val Ala Leu Lys Ser Glu Glu Asp
                355                 360                 365
Asn Gly Arg Ile Ala Thr Tyr Val Met Ala Phe Thr Leu Asp Gly Arg
    370                 375                 380
Phe Leu Leu Pro Glu Thr Lys Ile Gly Ser Val Lys Tyr Glu Gly Ile
385                 390                 395                 400
Glu Phe Ile

<210> SEQ ID NO 183
<211> LENGTH: 363
<212> TYPE: PRT
<213> ORGANISM: Cimex lectularius

<400> SEQUENCE: 183

Met Arg Ser Ser Tyr Arg Val Gly Asn Pro Ile Arg Phe Gln Pro Thr
1               5                   10                  15
Asn Val Val Gly Leu Leu Leu Ser Leu Val Leu Ser Phe Met Leu
            20                  25                  30
Val Gln Ser Tyr Glu Leu Gly His Ala Ser Gly Glu Thr Asn Ala Asn
        35                  40                  45
Ser Lys Pro Leu Thr Thr Pro Val Glu Glu Asn Leu Lys Val Arg Phe
    50                  55                  60
Lys Ile Gly Val Ile Ser Asp Asp Lys Asn Ala Val Ser Lys Asp
65                  70                  75                  80
Glu Ser Asn Thr Trp Val Ser Thr Tyr Leu Thr Gly Thr Leu Glu Trp
                85                  90                  95
Glu Lys Ser Thr Asp Lys Ile Thr Val Gln Trp Asp Lys Gly Asn Glu
            100                 105                 110
Lys Lys Val Lys Ser Lys Tyr Ser Tyr Gly Gly Arg Gly Met Glu Leu
        115                 120                 125
Ser Glu Leu Val Thr Phe Asn Gly Asn Leu Leu Thr Phe Asp Asp Arg
    130                 135                 140
Thr Gly Leu Val Tyr Ile Leu Lys Asp Asp Lys Val Tyr Pro Trp Val
145                 150                 155                 160
Val Leu Ala Asp Gly Asp Gly Lys Asn Ser Lys Gly Phe Lys Ser Glu
                165                 170                 175
Trp Ala Thr Glu Lys Ala Gly Asn Leu Tyr Val Gly Ser Ser Gly Lys
            180                 185                 190
Glu Trp Thr Thr Lys Glu Gly Thr Ile Glu Asn Tyr Asn Pro Met Trp
```

```
                   195                 200                 205
Val Lys Met Ile Asn Lys Asn Gly Glu Val Thr Ser Leu Asn Trp Gln
    210                 215                 220

Thr Asn Tyr Glu Lys Ile Arg Ser Ser Met Asn Ile Thr Phe Pro Gly
225                 230                 235                 240

Tyr Met Trp His Glu Ala Ala Cys Trp Ser Asp Lys Tyr Asn Lys Trp
                245                 250                 255

Phe Phe Leu Pro Arg Ala Leu Ser Gln Glu Ala Tyr Asp Ser Lys Lys
                260                 265                 270

Phe Glu Thr Gln Gly Ala Asn Val Ile Ile Ser Cys Asp Asp Lys Phe
            275                 280                 285

Glu Lys Cys Glu Pro Thr Gln Ile Gln Gly Lys Thr Glu Asp Lys Arg
        290                 295                 300

Gly Phe Ser Asn Phe Lys Phe Val Pro Thr Ser Glu Asp Lys Ile Ile
305                 310                 315                 320

Val Gly Leu Lys Thr Val Glu Ala Asp Asp Thr Thr Glu Thr Tyr Phe
                325                 330                 335

Thr Ala Phe Asp Leu Glu Gly Lys Val Leu Leu Glu Gly Thr Lys Ile
                340                 345                 350

Asp Asp His Lys Tyr Glu Gly Val Asp Phe Val
                355                 360

<210> SEQ ID NO 184
<211> LENGTH: 371
<212> TYPE: PRT
<213> ORGANISM: Homo sapiens

<400> SEQUENCE: 184

Met Thr Lys Ala Ala Asp Pro Arg Phe Arg Pro Arg Trp Lys Val Ile
1               5                   10                  15

Leu Thr Phe Phe Val Gly Ala Ala Ile Leu Trp Leu Leu Cys Ser His
                20                  25                  30

Arg Pro Ala Pro Gly Arg Pro Pro Thr His Asn Ala His Asn Trp Arg
            35                  40                  45

Leu Gly Gln Ala Pro Ala Asn Trp Tyr Asn Asp Thr Tyr Pro Leu Ser
    50                  55                  60

Pro Pro Gln Arg Thr Pro Ala Gly Ile Arg Tyr Arg Ile Ala Val Ile
65                  70                  75                  80

Ala Asp Leu Asp Thr Glu Ser Arg Ala Gln Glu Glu Asn Thr Trp Phe
                85                  90                  95

Ser Tyr Leu Lys Lys Gly Tyr Leu Thr Leu Ser Asp Ser Gly Asp Lys
                100                 105                 110

Val Ala Val Glu Trp Asp Lys Asp His Gly Val Leu Glu Ser His Leu
            115                 120                 125

Ala Glu Lys Gly Arg Gly Met Glu Leu Ser Asp Leu Ile Val Phe Asn
    130                 135                 140

Gly Lys Leu Tyr Ser Val Asp Asp Arg Thr Gly Val Val Tyr Gln Ile
145                 150                 155                 160

Glu Gly Ser Lys Ala Val Pro Trp Val Ile Leu Ser Asp Gly Asp Gly
                165                 170                 175

Thr Val Glu Lys Gly Phe Lys Ala Glu Trp Leu Ala Val Lys Asp Glu
                180                 185                 190

Arg Leu Tyr Val Gly Gly Leu Gly Lys Glu Trp Thr Thr Thr Thr Gly
            195                 200                 205
```

-continued

```
Asp Val Val Asn Glu Asn Pro Glu Trp Val Lys Val Val Gly Tyr Lys
    210             215             220

Gly Ser Val Asp His Glu Asn Trp Val Ser Asn Tyr Asn Ala Leu Arg
225             230             235             240

Ala Ala Ala Gly Ile Gln Pro Pro Gly Tyr Leu Ile His Glu Ser Ala
            245             250             255

Cys Trp Ser Asp Thr Leu Gln Arg Trp Phe Phe Leu Pro Arg Arg Ala
            260             265             270

Ser Gln Glu Arg Tyr Ser Glu Lys Asp Asp Glu Arg Lys Gly Ala Asn
        275             280             285

Leu Leu Leu Ser Ala Ser Pro Asp Phe Gly Asp Ile Ala Val Ser His
    290             295             300

Val Gly Ala Val Val Pro Thr His Gly Phe Ser Ser Phe Lys Phe Ile
305             310             315             320

Pro Asn Thr Asp Asp Gln Ile Ile Val Ala Leu Lys Ser Glu Glu Asp
            325             330             335

Ser Gly Arg Val Ala Ser Tyr Ile Met Ala Phe Thr Leu Asp Gly Arg
            340             345             350

Phe Leu Leu Pro Glu Thr Lys Ile Gly Ser Val Lys Tyr Glu Gly Ile
        355             360             365

Glu Phe Ile
    370
```